United States Patent
Schoenfisch et al.

(10) Patent No.: US 11,186,681 B2
(45) Date of Patent: Nov. 30, 2021

(54) S-NITROSOTHIOL-MEDIATED HYPERBRANCHED POLYESTERS

(71) Applicant: The University of North Carolina at Chapel Hill, Chapel Hill, NC (US)

(72) Inventors: Mark Schoenfisch, Chapel Hill, NC (US); Lei Yang, Carrboro, NC (US); Yuan Lu, Troy, MI (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/339,299

(22) PCT Filed: Oct. 5, 2017

(86) PCT No.: PCT/US2017/055371
§ 371 (c)(1),
(2) Date: Apr. 3, 2019

(87) PCT Pub. No.: WO2018/067838
PCT Pub. Date: Apr. 12, 2018

(65) Prior Publication Data
US 2019/0225747 A1    Jul. 25, 2019

Related U.S. Application Data

(60) Provisional application No. 62/405,655, filed on Oct. 7, 2016.

(51) Int. Cl.
| | |
|---|---|
| *C08G 63/91* | (2006.01) |
| *C08G 83/00* | (2006.01) |
| *A61K 33/00* | (2006.01) |
| *A61K 47/59* | (2017.01) |

(52) U.S. Cl.
CPC ............ *C08G 63/916* (2013.01); *A61K 33/00* (2013.01); *A61K 47/593* (2017.08); *C08G 83/006* (2013.01); *C08G 2230/00* (2013.01); *Y02P 20/55* (2015.11)

(58) Field of Classification Search
CPC ...... A01N 43/16; A01N 63/30; A61K 8/9728; A61K 8/37; A61K 8/365; A61K 8/33; C12P 19/44; A23B 4/20; A23B 9/26; A23B 5/14; A23B 7/154; A61Q 17/005; A61Q 5/02; A23L 2/44; C07H 15/04; A61P 31/10; A61P 31/04
See application file for complete search history.

(56) References Cited

U.S. PATENT DOCUMENTS

| | | | |
|---|---|---|---|
| 5,525,357 A | 6/1996 | Keefer et al. | |
| 5,632,981 A | 5/1997 | Saavedra et al. | |
| 5,650,442 A | 7/1997 | Mitchell et al. | |
| 5,650,447 A | 7/1997 | Keefer et al. | |
| 5,714,511 A | 2/1998 | Saavedra et al. | |
| 5,814,666 A | 9/1998 | Green et al. | |
| 5,840,759 A | 11/1998 | Mitchell et al. | |
| 5,910,316 A | 6/1999 | Keefer et al. | |
| 6,110,453 A | 8/2000 | Keefer et al. | |
| 6,200,558 B1 | 3/2001 | Saavedra et al. | |
| 6,261,594 B1 | 7/2001 | Smith et al. | |
| 6,451,337 B1 | 9/2002 | Smith et al. | |
| 6,911,433 B2 | 6/2005 | Saavedra et al. | |
| 7,928,079 B2 | 4/2011 | Hrabie et al. | |
| 9,238,038 B2 | 1/2016 | Schoenfisch et al. | |
| 9,850,322 B2 | 12/2017 | Schoenfisch et al. | |
| 2001/0000039 A1 | 3/2001 | Toone et al. | |
| 2003/0078365 A1 | 4/2003 | Stamler et al. | |
| 2003/0093143 A1 | 5/2003 | Zhao et al. | |
| 2004/0038947 A1 | 2/2004 | Wink et al. | |
| 2005/0009789 A1 | 1/2005 | Wink et al. | |
| 2005/0228184 A1 | 10/2005 | Haj-Yehia | |
| 2005/0265956 A1 | 12/2005 | Liu et al. | |
| 2007/0243131 A1 | 10/2007 | Chen et al. | |
| 2009/0214618 A1* | 8/2009 | Schoenfisch ............ B82Y 30/00 424/426 |
| 2009/0222088 A1 | 9/2009 | Chen et al. | |
| 2009/0232863 A1 | 9/2009 | Cheng et al. | |
| 2010/0305489 A1 | 12/2010 | Liu et al. | |
| 2011/0002999 A1 | 1/2011 | Chen et al. | |
| 2011/0150999 A1 | 6/2011 | Chu et al. | |
| 2012/0034169 A1 | 2/2012 | Schoenfisch et al. | |
| 2013/0196951 A1 | 8/2013 | Schoenfisch et al. | |

(Continued)

FOREIGN PATENT DOCUMENTS

| | | |
|---|---|---|
| CA | 2205564 C | 7/2006 |
| CN | 106046382 A | 10/2016 |

(Continued)

OTHER PUBLICATIONS

Liang Future Sci. NO generating-releasing materials p. 1-10 August(Year: 2015).*
Luo Cell p. 823 March (Year: 2009).*
U.S. Appl. No. 62/405,655, filed Oct. 7, 2016, Mark Schoenfisch.
Bogdan, C., Nitric Oxide and the Immue Response. Nat Immunol. 2001; 2(10):907-16.
Carlmark, A. et al., Dendritic Architechtures Based on bis-MPA: Functional Polymeric Scaffolds for Application-Driven Research. Chem Soc Rev. 2013; 42:5858-79.
Carpenter, A.W. and Schoenfisch, M.H., Nitric Oxide Release: Part II. Therapeutic Applications. Chem Soc Rev. 2012; 41(10):3742-52.
Cleland, W.W., Diothiothreitol, A New Protective Reagent for SH Groups. Biochemical. 1964; 3(4):480-2.

(Continued)

*Primary Examiner* — Matthew P Coughlin
*Assistant Examiner* — Thurman Wheeler
(74) *Attorney, Agent, or Firm* — Ballard Spahr LLP

(57) ABSTRACT

The invention generally relates to compositions comprising degradable polymers and methods of making degradable polymers. Specifically, the disclosed degradable polymers comprise a biodegradable polymer backbone, a nitric oxide linker moiety, and a nitric oxide molecule. This abstract is intended as a scanning tool for purposes of searching in the particular art and is not intended to be limiting of the present invention.

12 Claims, 9 Drawing Sheets

(56) References Cited

U.S. PATENT DOCUMENTS

| | | |
|---|---|---|
| 2013/0337033 A1 | 12/2013 | Balkus, Jr. et al. |
| 2015/0225488 A1 | 8/2015 | Schoenfisch et al. |
| 2017/0333456 A1 | 11/2017 | Miranda et al. |
| 2019/0322770 A1 | 10/2019 | Schoenfisch et al. |
| 2020/0021657 A1 | 7/2020 | Brinkmann et al. |

FOREIGN PATENT DOCUMENTS

| | | |
|---|---|---|
| CN | 2017800700937 | 10/2017 |
| EP | 0726768 B1 | 5/2000 |
| EP | 2547660 B1 | 1/2015 |
| EP | 17859196.2 | 10/2017 |
| JP | 2005047979 A | 2/2005 |
| JP | 4285775 B2 | 6/2009 |
| WO | WO 93/25521 A1 | 12/1993 |
| WO | WO 1996/015797 A1 | 5/1996 |
| WO | WO 1996/032136 | 10/1996 |
| WO | WO 1998/005689 A1 | 2/1998 |
| WO | WO 1998/013358 A1 | 4/1998 |
| WO | WO 0030658 A1 | 6/2000 |
| WO | WO-2007/085254 A1 | 8/2007 |
| WO | WO 2009/049208 A1 | 4/2009 |
| WO | WO 2010/096320 A2 | 8/2010 |
| WO | WO-2010/096320 A2 | 8/2010 |
| WO | WO-2011/003172 A1 | 1/2011 |
| WO | WO 2012/046994 A2 | 4/2012 |
| WO | WO-2012/116177 A2 | 8/2012 |
| WO | WO 2014/028847 A1 | 2/2014 |
| WO | PCT/US2017/0553 | 10/2017 |
| WO | WO-2018/067838 A1 | 4/2018 |
| WO | WO 2018/127819 A1 | 7/2018 |
| WO | WO 2018/178902 A1 | 10/2018 |
| WO | WO 2019/099525 A1 | 5/2019 |
| WO | WO 2019/173539 A1 | 9/2019 |
| WO | WO 2020/139857 | 7/2020 |

OTHER PUBLICATIONS

Coneski, P.N. and Schoenfisch, M.H., Nitric Oxide Release: Part III. Measurement and Reporting. Chem Soc Rev. 2012; 41(10):3753-8.

Coneski, P.N. and Schoenfisch, M.H., Synthesis of Nitric Oxide-Releasing Polyurethanes with S-Nitrosothiol-Containing Hard and Soft Segments. Polym Chem. 2011; 2(4):906-13.

Coneski, P.N. et al., Degradable Nitric Oxide-Releasing Biomaterials via Post-Polymerization Functionalization of Cross-Linked Polyesters. Biomacromolecules. 2010; 11(11):3208-15.

Cooke, J.P., NO and Angiogenesis. Atheroscler Suppl. 2003; 4(4):53-60.

Damodaran, V.B. and Reynolds, M.M., Biodegradable S-Nitrosothiol Tethered Multiblock Polymer for Nitric Oxide Delivery. J Mater Chem. 2011; 21:5870-2.

Feliu, N. et al., Stability and Biocompatibility of a Library of Polyester Dendrimers in Comparison to Polyamidoamine Dendrimers. Biomaterials. 2012; 33(7):1970-81.

Frost, M.C. and Meyerhoff, M.E., Synthesis, Characterization, and Controlled Nitric Oxide Release from S-Nitrosothiol-Derivatized Fumed Silica Polyme Filler Particles. J Biomed Mater Res Part A. 2005; 72A(4):409-19.

Gabor, G. and Vincze, A., Determination of Thiols in Non-Aqueous Solutions. Anal Chim Acta. 1977; 92(2):429-31.

Hetrick, E.M. and Schoenfisch, Analytical Chemistry of Nitric Oxide. Annu Rev Anal Chem (Palo Alto Calif). 2009; 2:409-33.

Hetrick, E.M. et al., Bactericidal Efficacy of Nitric Oxide-Releasing Silica Nanonparticles. ACS Nano. 2008; 2(2):235-46.

Karatasos, K., Self-Association and Complexation of the Anti-Cancer Drug Doxorubicin with PEGylated Hyperbranched Polyesters in an Aqueous Environment. J Phys Chem B. 2013; 117(8):2564-75.

Liu, T. et al., Hollow Polymer Nanoparticles with S-Nitrosothiols as Scaffolds for Nitric Oxide Release. J Colloid Interface Sci. 2015; 459:115-22.

Lu, Y. et al., S-Nitrosothiol-Modified Nitric Oxide-Releasing Chitosan Oligosacccarides as Antibacterial Agents. Acta Biomater. 2015; 12:62-9.

Lu, Y. et al., Nitric Oxide-Releasing Amphiphilic Poly(Amidoamine) (PAMAM) Dendrimers as Antibacterial Agents. Biomacromolecules. 2013; 14(10):3589-98.

Lu, Y. et al., Structurally Diverse Nitric Oxide-releasing Poly(propylene imine) Dendrimers. Chem Mater. 2011; 23(18):4227-33.

Lu, Y. et al., Shape- and Nitric Oxide Flux-Dependent Bactericidal Activity of Nitric Oxide-Releasing Silica Nanorods. Small. 2013; 9(12):2189-98.

Luo, J.-d. and Chen, A.F., Nitric Oxide: a Newly Discovered Function on Wound Healing. Acta Pharmacol Sin. 2005; 26(3):259-64.

Lutzke, A. et al., Nitric Oxide-Releasing S-Nitrosated Derivatives of chitin and Chitosan for Biomedical Applications. J Mater Chem B. 2014; 2:7449-58.

MacMicking, J. et al., Nitric Oxide and Macrophage Function. Annu Rev Immunol. 1997; 15: 323-50.

Malmström, E. et al., Hyperbranched Aliphatic Polyesters. Macromolecules. 1995; 28(5):1698-703.

Nakamoto, H. and Bardwell, J.C.A., Catalysis of Disulfide Bond Formation and Isomerization in the *Escherichia coli* Periplasm. Biochim Biophys Acta. 2004; 1694(1-3):111-9.

Nichols, S.P. et al., Local Delivery of Nitric Oxide: Targeted Delivery of Therapeutics to Bone and Connective Tissues. Adv Drug Deliv Rev. 2012; 64(12):1177-88.

O'Halloran, T.V. and Culotta, V.C., Metallochaperones, an Intercellular Shuttle Service for Metal Ions. J Biol Chem. 2000; 275(33):25057-60.

Prabaharan, M. et al., Amphiphilic Multi-Arm-Block Copolymer Conjugated with Doxorubicin via pH-Sensitive Hydrazone Bond for Tumor-Targeted Drug Delivery. Biomaterials. 2009; 30(29):5757-66.

Rees, D.D. et al., Role of Endothelium-Derived Nitric Oxide in the Regulation of Blood Pressure. Proc Natl Acad Sci USA. 1989; 86(9):3375-8.

Riccio, D.A. and Schoenfisch, M.H., Nitric Oxide Release: Part I. Macromolecular Scaffolds. Chem Soc Rev. 2012; 41 (10):3731-41.

Riccio, D.A. et al., Photoinitiated Nitric Oxide-Releasing Tertiary S-Nitrosothiol-Modified Xerogels. ACS Appl Mater Interfaces. 2012; 4(2):796-804.

Riccio, D.A et al., Stöber Synthesis of Nitric Oxide-Releasing S-Nitrosothiol-Modified Silica Particles. Chem Mater. 2011; 23(7):1727-35.

Roy, B. et al., New Thionitrates: Synthesis, Stability, and Nitric Oxide Generation. J Org Chem. 1994; 59(23):7019-26.

Schäffer, M.R. et al., Nitric Oxide regulates Wound Healing. J Surg Res. 1996; 63(1):237-40.

Seabra, A.B. et al., Antibacterial Nitric Oxide-Releasing Polyester for the Coating of Blood-Contacting Artificial Materials. Artif Organs. 2010; 34(7):E204-14.

Shishido, S.M. amnd Oliveira, M.G., Polyethylene Glycol Matrix Reduces the Rates of Photochemical and Thermal Release of Nitric Oxide from S-Nitroso-N-Acetylcysteine. Photochem Photobiol. 2000; 71(3):273-80.

Slomberg, D.L. et al., Role of Size and Shape on Biofilm Eradication for Nitric Oxide-releasing Silica. ACS Appl Mater Interfaces. 2013; 5(19):9322-9.

Soto, R.J. et al., Functionalize Mesoporous Silica via an Aminosilane Surfactant Ion Exchange Reaction: Controlled Scaffold Design and Nitric Oxide Release. ACS Appl mater Interfaces. 2016; 8(3):2220-31.

Stasko, N.A. et al., S-Nitrosothiol-Modified Dendrimers as Nitric Oxide Delivery Vehicles. Biomacromolecules. 2008; 9(3):834-41.

Sun, B. et a., Nitric Oxide-Releasing Dendrimers as Antibacterial Agents. Biomacromolecules. 2012; 13(10):3343-54.

Valko, M. et al., Metals, Toxicity and Oxidative Stress. Curr Med Chem. 2005; 12(10):1161-208.

Voit, B.I. and Lederer, A., Hyperbranched and Highly Branched Polymer Architectures—Synthetic Strategies and Major Characterization Aspects. Chem Rev. 2009; 109(11):5924-73.

(56) References Cited

OTHER PUBLICATIONS

Wang, J. and Xu, Tongwen, Facile Construction of Multivalent Targeted Drug Delivery System from Boltorn® Series Hyperbranched Aliphatic Polyester an Folic Acid. Poly Adv Technol. 2009; 22:763-7.
Williams, D.L.H., The Chemistry of S-Nitrosothiols. Acc Chem Res. 1999; 32(10):869-76.
Williams, D.L.H., Nitrosation Reactions and the Chemistry of Nitric Oxide. Elsevier. 2004.
Williams, D.L.H., S-Nitrosation and the Reactions of S-Nitroso Compounds. Chem Soc Rev. 1985; 14(2):171-96.
Worley, B.V. et al., Nitric Oxide-Releasing Quarternary Ammonium-Modified Poly(amidoamine) Dendrimers as Dual Action Antibacterial Agents. Bioconjug Chem. 2014; 25(5):918-27.
Xiao, Y.L. et al., Multifunctional Unimolecular Micelles for cancer-Targeted Drug Delivery and Positron Emission Tomography Imaging. Biomaterials. 2012; 33(11):3071-82.
Yapor, J.P. et al., Biodegradable Citrate-Based Polyesters with S-Nitrosothiol Functional Groups for Nitric Oxide Release. J Mater Chem B. 2015; 3(48):9233-41.
Žagar, E. and Žigon, M., Aliphatic Hyperbranched Polyesters Based on 2,2-bis(methylol)propionic Acid—Determination of Structure, Solution and Bulk Properties. Prog Polymer Sci. 2011; 36(1):53-88.
Zeng, X.H. et al., Endocytic Uptake and Intracellular Trafficking of Bis-MPA-Based Hyperbranched Copolymer Micelles in Breast Cancer Cells. Biomacromolecules. 2012; 13(11):3814-22.
Zhai, X. et al., Amphiphilic Dendritic Molecules: Hyperbranched Polyesters with Alkyl-Terminated Branches. Macromolecules. 2003; 36(9):3101-10.
Zhang, H. et al., Hyperbranched Polyester Hydrogels with Controlled Drug Release and Cell Adhesion Properties. Biomacromolecules. 2013; 14(5):1299-310.
Zhang, H. et al., Nitric Oxide-Releasing Fumed Silica Particles: Synthesis, Characterization, and Biomedical Application. J Am Chem Soc. 2003; 125(17):5015-24.
Zhang, X.F. et al., Nitric Oxide Delivery by Core/Shell Superparamagnetic Nanoparticle Vehicles with Enhanced Biocompatibility. Langmuir. 2012; 28(35):12879-85.
Zhou, Z.R. et al., Water-Soluble Poly(ethylenimine)-Based Nitric Oxide Donors: Preparation, Characterization, and Potential Application in Hemodialysis. Biomacromolecules. 2006; 7(9):2565-74.
International Search Report and Written Opinion dated Dec. 28, 2017 by the International Searching Authority for Patent Application No. PCT/US2017/055371, which was filed on Oct. 5, 2017 and published as WO 2018/067838 on Apr. 12, 2018 (Applicant—The University of North Carolina at Chapel Hill; (7 pages).
Coneski: "Design and Synthesis of Nitric Oxide Releasing Polymers for Biomedical Applications", (2010), pp. 122-127, Retrieved from the Internet: URL:https://cdr.lib.unc.edu/indexablecontent/uuid:d84bce49-d4dd-4026-96a5-3ea9e82dee9c [retrieved on Oct. 9, 2015].
Fu et al: "Preparation and reversible photo crosslinking/photocleavage behavior of 4-methylcoumarin functionalized hyperbranched polyester", polymer, , vol. 49, No. 23, (2008), pp. 4981-4988.
Zamboulis et al: "Polyglycerol Hyperbranched Polyesters: Synthesis, Properties and Pharmaceutical and Biomedical Applications", International Journal of Molecular Sciences, vol. 20, No. 24, (2019), p. 6210.
Fu, et al. (2008) "Preparation and reversible photo-crosslinking/photocleavage behavior o 4-methylcoumarin functionalized hyperbranched polyester" *Polymer* 49(23): 4981-4988.
European Search Report dated May 4, 2020 by the European Search Authority for EP Application No. 17859196.2, filed on Oct. 5, 2017 and published as EP 3523367 on Aug. 14, 2019 (Applicant—The University of North Carolina at Chapel Hill) (32 pages).
Ahonen Mona et al., "Nitric oxide-releasing alginate as a biodegradable antibacterial scaffold," 253rd National Meeting of the American-Chemical-Society (ACS) on Advanced Materials, Technologies, Systems, and Processes; San Francisco, CA, USA; Apr. 2-6, 2017—Abstracts of Papers (Apr. 2, 2017), p. 600, XP009521645.
Ahonen, M. J. R., Hill, D. B. & Schoenfisch, M. H. Nitric oxide-releasing alginates as mucolytic agents. *ACS Biomater. Sci. Eng.* 5, 3409-3418 (2019).
Backlund et al., "Antibacterial Efficacy of Exogenous Nitric Oxide on Periodontal Pathogens," J Dent Res, 93(11):1089-1094, (2014).
Backlund et al., "Anti-biofilm action of nitric oxide-releasing alkyl-modified poly(amidoamine) dendrimers against *Streptococcus* mutans," Acta Biomaterialia, 29:198-205, (2016).
Backlund et al., "Kinetic-dependent Killing of Oral Pathogens with Nitric Oxide," J Dent Res, 94(8):1092-1098, (2015).
Barraud, N., Kelso, M., Rice, S. & Kjelleberg, S. Nitric Oxide: A Key Mediator of Biofilm Dispersal with Applications in Infectious Diseases. *Curr. Pharm. Des.* 21,31-42 (2014).
Benkovics et al., "A multifunctional β-cyclodextrin-conjugate photodelivering nitric oxide with fluorescence reporting," International Journal of Pharmaceutics, 531: 614-620 (2017).
Bhardwaj, Atul, et al., "A diazen-1-ium-1,2-diolate analog of 7-azabenzobicyclo [2.2. 1] heptane: Synthesis, nitric oxide and nitroxyl release, in vitro hemodynamic, and anti-hypertensive studies," Bioorganic & Medicinal Chemistry Letters, (2013), vol. 23, No. 9: 2769-2774.
Boas and Heegaard, "Dendrimers in drug research," Chem. Soc. Rev., 33(1):43-63, (2004).
Calabretta et al., "Antibacterial activities of poly (amidoamine) dendrimers terminated with amino and poly (ethylene glycol) groups," Biomacromolecules, 8(6):1807-1811, (2007).
Caminade et al., "Dendrimers and hyperbranched polymers," Chem. Soc. Rev, 44(12):3870-3873, (2015).
Cao et al., "Synthesis and striking fluorescence properties of hyperbranched poly (amido amine)," J. Macromol. Sci. Pure Appl. Chem., 44(4):417-424, (2007).
Carlmark et al., "New methodologies in the construction of dendritic materials," Chem. Soc. Rev., 38(2):352-362, (2009).
Carpenter et al., "Dual action antimicrobials: nitric oxide release from quaternary ammonium-functionalized silica nanoparticles," Biomacromolecules, 13(10):3334-3342, (2012).
Chakrapani, Harinath, et al., "Nitric oxide prodrugs: diazeniumdiolate anions of hindered secondary amines," Organic Letters, (2007), vol. 9, No. 22: 4551-4554.
Chen et al., "Cytotoxicity, hemolysis, and acute in vivo toxicity of dendrimers based on melamine, candidate vehicles for drug delivery," J. Am. Chem. Soc., 126(32):10044-10048, (2004).
Chen et al., "Hyperbranched glycoconjugated polymer from natural small molecule kanamycin as a safe and efficient gene vector," Polym. Chem., 2:2674-2682, (2011).
Chen et al., "Hyperbranched polymers from $A_2$ +$B_3$ strategy: recent advances in description and control of fine topology," Polym. Chem., 7(22):3643-3663, (2016).
Chen et al., "Multifunctional Hyperbranched Glycoconjugated Polymers Based on Natural Aminoglycosides," Bioconjugate Chemistry, 23(6):1189-1199, (2012).
Cheng et al., "Michael Addition Polymerization of Trifunctional Amine and Acrylic Monomer: A Versatile Platform for Development of Biomaterials ," Biomacromolecules, 17(10):3115-3126, (2016).
Cooke et al., "Nitric Oxide and Angiogenesis," Circulation, 105:2133-2135, (2002).
Da Silva et al., "Antimicrobial peptide control of pathogenic microorganisms of the oral cavity: A review of the literature," Peptides, 36(2):315-321, (2012).
Davies et al., "Chemistry of the Diazeniumdiolates. 2. Kinetics and Mechanism of Dissociation to Nitric Oxide in Aqueous Solution," J. Am. Chem. Soc., 123(23):5473-5481, (2001).
Deupree, S. M. & Schoenfisch, M. H. Morphological analysis of the antimicrobial action of nitric oxide on Gram-negative pathogens using atomic force microscopy. *Acta Biomater.* 5, 1405-1415 (2009).
Duncan and Izzo, "Dendrimer biocompatibility and toxicity," Adv. Drug Deliv. Rev., 57(14):2215-2237, (2005).

(56) References Cited

OTHER PUBLICATIONS

Duong et al., "Functional gold nanoparticles for the storage and controlled release of nitric oxide: applications in biofilm dispersal and intracellular delivery," J. Mater. Chem. B-2, 2(31):5003-5011, (2014).

Duong et al., "Nanoparticle (Star Polymer) Delivery of Nitric Oxide Effectively Negates *Pseudomonas aeruginosa* Biofilm Formation," Biomacromolecules, 15(7):2583-2589, (2014).

European Search Report and Search Opinion dated Aug. 3, 2020 by the European Search Authority for EP Application No. 18736471.6, filed on Jan. 3, 2018 and published as EP 3565848 on Nov. 13, 2019 (Applicant—The University of North Carolina at Chapel Hill) (8 pages).

European Search Report and Written Opinion were dated May 4, 2020 by the European Patent Office for EP Application No. 17859196. 2, filed on Oct. 5, 2017 and published as 3523367 on Aug. 14, 2019 (Applicant—The University of North Carolina At Chapel Hill) (32 Pages).

Fang, Ferric C., "Antimicrobial reactive oxygen and nitrogen species: concepts and controversies," Nat. Rev. Micro., 2(10):820-832, (2004).

Gao and Koo, "Do catalytic nanoparticles offer an improved therapeutic strategy to combat dental biofilms?," Nanomed. Nanotech. Biol. Med., 12(4):275-279, (2017).

Gao and Yan, "Hyperbranched polymers: from synthesis to applications," Prog. Polym. Sci., 29(3):183-275, (2004).

Gao, Q, et al., "Synthesis and Characterization of Chitosan-Based Diazeniumdiolates," Polymer Materials Science and Engineering, Dec. 2008, pp. 42-45, vol. 24(12). (Abstract).

Gibney et al., "Poly(ethylene imine)s as antimicrobial agents with selective activity," Macromol. Biosci., 12(9):1279-1289, (2012).

Hall, J. R. et al. Mode of nitric oxide delivery affects antibacterial action. *ACS Biomater. Sci. Eng.* acsbiomaterials.9b01384 (2019). doi:10.1021/acsbiomaterials.9b01384.

Hopkins, Sean, "Development of high capacity hyperbranched nitric oxide donors for controlling ubcutaneous inflammation," Open Access Dissertation, Michigan Technological University, 154 pages, (2015).

Hossain et al., "Discovery of Two Bacterial Nitric Oxide-Responsive Proteins and Their Roles in Bacterial Biofilm Regulation," Acc. Chem. Res., 50(7):1633-1639, (2017).

Hrabie, Joseph A., et al., "New nitric oxide-releasing zwitterions derived from polyamines," *The Journal of Organic Chemistry*, (1993), vol. 58, No. 6: 1472-1476.

Huang et al., "Nitric oxide-loaded echogenic liposomes for nitric oxide delivery and inhibition of intimal hyperplasia," J. Am. Coll. Cardiol., 54(7):652-659, (2009).

Huang et al., "Reduction-responsive multifunctional hyperbranched polyaminoglycosides with excellent antibacterial activity, biocompatibility and gene transfection capability," Biomaterials, 106:134-143, (2016).

International Preliminary Report on Patentability dated Apr. 9, 2019 by the International Searching Authority for Patent Application No. PCT/US2017/055371, which was filed on Oct. 5, 2017 and published as WO 2018/067838 on Apr. 12, 2018 (Applicant—The University of North Carolina at Chapel Hill; (6 pages).

International Search Report and Written Opinion dated Dec. 23, 2013 in International Application No. PCT/US2013/055360.

International Search Report and Written Opinion dated Dec. 28, 2017 by the International Searching Authority for Patent Application No. PCT/US2017/055371, which was filed on Oct. 5, 2017 and published as WO 2018/067838 on Apr. 12, 2018 (Applicant—The University of North of Carolina at Chapel Hill; (7 pages).

Jin et al., "Nitric Oxide-Releasing Cyclodextrins," Journal of the American Chemical Society, 140:14178-14184 (2018).

Jin et al., "Biocompatible or biodegradable hyperbranched polymers: from self-assembly to cytomimetic applications," Chem. Soc. Rev., 41(18):5986-5997, (2012).

Jones et al., "Antimicrobial properties of nitric oxide and its application in antimicrobial formulations and medical devices," Appl. Microbiol. Biotechnol., 88(2):401-407, (2010).

Jones, C.G., "Chlorhexidine: is it still the gold standard?" Periodontology 2000, 15:55-62, (1997).

Kailasan et al., "Synthesis and characterization of thermoresponsive polyamidoamine-polyethylene glycol-poly (d, l-lactide) core-shell nanoparticles," Acta Biomater. 6(3): 1131-1139, (2010).

Keefer et al., "Chemistry of the Diazeniumdiolates I. Structural and Spectral Characteristics of the [N(O)NO]—Functional Group," Nitric Oxide, 5(4):377-394, (2001).

Keefer et al., "'NONOates' (1-Substituted Diazen- 1-ium-1,2-diolates) as Nitric Oxide Donors: Convenient Nitric Oxide Dosage Forms," Methods in Enzymology, 268:281-293, (1996).

Keefer, Larry K., "Fifty Years of Diazeniumdiolate Research. From Laboratory Curiosity to Broad-Spectrum Biomedical Advances," ACS Chemical Biology, (2011), vol. 6, No. 11, 1147-1155.

Keefer, Larry K., "Nitric Oxide (NO)—and Nitroxyl (HNO)-Generating Diazeniumdiolates (NONOates): Emerging Commercial Opportunities," Current Topics in Medicinal Chemistry, 5(7):625-636, (2005).

Kim et al., "NONOates-polyethylenimine hydrogel for controlled nitric oxide release and cell proliferation modulation," Bioconjugate Chem., 22(6):1031-1038, (2011).

Knop et al., "Poly(ethylene glycol) in drug delivery: pros and cons as well as potential alternatives," Angew. Chem. Int. Ed., 49(36):6288-6308, (2010).

Konter, Joerg, et al., "Synthesis of Diazen-1-ium-1, 2-diolates Monitored by the "NOtizer" Apparatus: Relationship between Formation Rates, Molecular Structure and the Release of Nitric Oxide," European Journal of Organic Chemistry, (2007), vol. 2007, No. 4 : 616-624.

Kurniasih et al., "Dendritic nanocarriers based on hyperbranched polymers," Chem. Soc. Rev., 44(12):4145-4164, (2015).

Labena et al., "One-pot synthesize of dendritic hyperbranched PAMAM and assessment as a broad spectrum antimicrobial agent and anti-biofilm," Mater. Sci. Eng. C Mater. Biol. Appl., 58:1150-1159, (2016).

Lenoir et al., "Polyolefin matrixes with permanent antibacterial activity: preparation, antibacterial activity, and action mode of the active species," Biomacromolecules, 7(8):2291-2296, (2006).

Liu et al., "Hollow double-layered polymer microspheres with pH and thermo-responsive properties as nitric oxide-releasing reservoirs," Polym. Chem., 6(17):3305-3314, (2015).

Liu et al., "Synergistic supramolecular encapsulation of amphiphilic hyperbranched polymer to dyes," Macromolecules, 39(23):8102-8111, (2006).

Lowe et al., "Storage and delivery of nitric oxide via diazeniumdiolated metal organic framework," Micropor. Mesopor. Mat., 181:17-22, (2013).

Lu, Y., Slomberg, D. L. & Schoenfisch, M. H. Nitric Oxide-Releasing Chitosan Oligosaccharides as Antibacterial Agents. *Biomaterials* 35, 1716-1724 (2014).

Luo et al., "Poly (ethylene glycol)-conjugated PAMAM dendrimer for biocompatible, high-efficiency DNA delivery," Macromolecules, 35(9):356-3462, (2002).

Lutzke, et al. (2016) "Nitric oxide release from a biodegradable cysteine-based polyphosphazene" Journal of Materials Chemistry B 4(11): 1987-1988.

Maragos, Chris M., et al., "Complexes of. NO with nucleophiles as agents for the controlled biological release of nitric oxide. Vasorelaxant effects," Journal of Medicinal Chemistry, (1991), vol. 34, No. 11:3242-3247.

Matai et al., "Chemically Cross-Linked Hybrid Nanogels of Alginate and PAMAM Dendrimers as Efficient Anticancer Drug Delivery Vehicles," ACS Biomater. Sci. Eng., 2(2):213-223, (2016).

Mather et al., "Michael addition reactions in macromolecular design for emerging technologies," Prog. Polym. Sci., 31(5):487-531, (2006).

Miller et al., "Gaseous nitric oxide bactericidal activity retained during intermittent high-dose short duration exposure," Nitric Oxide, 20:16-23, (2009).

(56) References Cited

OTHER PUBLICATIONS

Miller MR, Megson IL. Recent developments in nitric oxide donor drugs. Br J Pharmacol. 2007;151(3):305-321. doi:10.1038/sj.bjp. 0707224.
Moreno-Sastre et al., "Pulmonary delivery of tobramycin-loaded nanostructured lipid carriers for *Pseudomonas aeruginosa* infections associated with cystic fibrosis," International Journal of Pharmaceutics, 498:263-273, (2016).
Mourtzis et al., "Synthesis, characterization, and remarkable biological properties of cyclodextrins bearing guanidinoalkylamino and aminoalkylamino groups on their primary side," Chem. Eur. J., 14: 4188-4200 (2008).
Nair et al., "Biodegradable polymers as biomaterials," Prog. Polym. Sci., 32(8-9):762-798, (2007).
Nguyen et al., "Co-delivery of nitric oxide and antibiotic using polymeric nanoparticles," Chem Sci., 7(2):1016-1027, (2016).
Nordgard et al., "Alterations in Mucus Barrier Function and Matrix Structure Induced by Guluronate Oligomers," Biomacromolecules, 15:2294-2300, (2014).
Park et al., "Nitric oxide integrated polyethylenimine-based triblock copolymer for efficient antibacterial activity," Biomaterials, 34(34):8766-8775, (2013).
Park et al., "Polydopamine Hollow Nanoparticle Functionalized with N-diazeniumdiolates as a Nitric Oxide Delivery Carrier for Antibacterial Therapy," Adv. Healthcare Mater., 5(16):2019-2024, (2016).
Parzuchowski et al., "Synthesis and characterization of polymethacrylate-based nitric oxide donors," J. Am. Chem. Soc 124(41):12182-12191, (2002).
Paula and Koo, "Nanosized building blocks for customizing novel antibiofilm approaches," J. Dent. Res., 96(2):128-136, (2017).
Piras et al., "S-Nitroso-Beta-Cyclodextrins as New Bimodal Carriers: Preparation, Detailed Characterization, Nitric-Oxide Release, and Molecular Encapsulation," Chemistry—An Asian Journal, 8:2768-2778 (2013).
Polizzi et al., "Water-Soluble Nitric Oxide-Releasing Gold Nanoparticles," Langmuir, 23:4938-4943, (2007).
Privett, B. J. et al. Synergy of nitric oxide and silver sulfadiazine against gram—negative, gram-positive, and antibiotic-resistant pathogens. *Mol. Pharm.* 7, 2289-2296 (2010).
Privett, B. J., Broadnax, A. D., Bauman, S. J., Riccio, D. A. & Schoenfisch, M. H. Examination of Bacterial Resistance to Exogenous Nitric Oxide. *Nitric Oxide* 26, 126-173 (2012).
Reighard, K. P., Hill, D. B., Dixon, G. A., Worley, B. V. & Schoenfisch, M. H. Disruption and eradication of P. aeruginosa biofilms using nitric oxide-releasing chitosan oligosaccharides. *Biofouling* 31, 775-87 (2015).
Safdar et al., "Targeted diazeniumdiolates: Localized nitric oxide release from glioma-specific peptides and proteins," Int. J. Pharm., 422(1-2):264-270, (2012).
Schairer, D. O., Chouake, J. S., Nosanchuk, J. D. & Friedman, A. J. The potential of nitric oxide releasing therapies as antimicrobial agents. Virulence 3, 271-279 (2012).
Shah Su, Socha M, Fries I, Gibaud S. Synthesis of S-nitrosoglutathione-alginate for prolonged delivery of nitric oxide in intestines. Drug Deliv. 2016;23(8):2927-2935. doi:10.3109/10717544.2015. 1122676.
Shin et al., "Inorganic/Organic Hybrid Silica Nanoparticles as a Nitric Oxide Delivery Scaffold," Chem. Mater., 20:239-249, (2008).
Soto et al., "Design Considerations for Silica-Particle-Doped Nitric-Oxide-Releasing Polyurethane Glucose Biosensor Membranes," ACS Sensors, 2(1):140-150, (2017).
Stasko and Schoenfisch, "Dendrimers as a Scaffold for Nitric Oxide Release," J. Am. Chem. Soc., 128(25):8265-8271, (2006).
Stasko et al., "Cytotoxicity of polypropylenimine dendrimer conjugates on cultured endothelial cells," Biomacromolecules, 8(12):3853-3859, (2007).
Suchyta and Schoenfisch, "Controlled release of nitric oxide from liposomes," ACS Biomater. Sci. Eng., 3(9):2136-2143, (2017).

Supplementary European Search Report dated Feb. 5, 2016 from related EP Application No. 13829755.1.
Tomalia et al., "A New Class of Polymers: Starburst-Dendritic," Polym. J, 17:117-132, (1985).
Voit and Lederer, "Hyperbranched and highly branched polymer architectures-synthetic strategies and major characterization aspects," Chem. Rev., 109(11):5924-5973, (2009).
Wan, A., et al., "Characterization of folate-graft-chitosan as a scaffold for nitric oxide release," International Journal of Biological Macromolecules, 2008, pp. 415-421, vol. 43, Elsevier B.V.
Wan, A., et al., "Effects of Molecular Weight and Degree of Acetylation on the Release of Nitric Oxide from Chitosan—Nitric Oxide Adducts," Journal of Applied Polymer Science, 2010, pp. 2183-2188, vol. 117, Wiley Periodicals, Inc.
Wang et al., "Synthesis and applications of stimuli-responsive hyperbranched polymers," Prog. Polym. Sci., 64:114-153, (2017).
Wang et al., "Synthesis and gene delivery of poly(amido amine)s with different branched architecture," Biomacromolecules, 11(2):489-495, (2010).
Wang et al., "Bioapplications of hyperbranched polymers," Chemical Society Reviews, 44(12):4023-4071, (2015).
Wang et al., "Synthesis and evaluation of phenylalanine-modified hyperbranched poly (amido amine) s as promising gene carriers," Biomacromolecules, 11(1):241-251, (2009).
Wang et al., "The effect of a branched architecture on the antimicrobial activity of poly(sulfone amines) and poly(sulfone amine)/silver nanocomposites" J. Mater. Chem., 22:15227-15234, (2012).
Wink et al., "DNA deaminating ability and genotoxicity of nitric oxide and its progenitors," Science, 254(5034):1001-1003, (1991).
WIPO Application No. PCT/IB2018/050051, PCT International Search Report and Written Opinion of the International Searching Authority dated Jun. 8, 2018.
WIPO Application No. PCT/IB2018/052144, PCT International Search Report and Written Opinion of the International Searching Authority dated Aug. 8, 2018.
WIPO Application No. PCT/US2018/061061, PCT International Search Report and Written Opinion of the International Searching Authority dated Apr. 5, 2019.
WIPO Application No. PCT/US2019/021051, PCT International Search Report and Written Opinion of the International Searching Authority dated Jun. 21, 2019.
WIPO Application No. PCT/US2019/068412, PCT International Search Report and Written Opinion of the International Searching Authority dated May 21, 2020.
Wo et al., "Recent advances in thromboresistant and antimicrobial polymers for biomedical applications: just say yes to nitric oxide (NO)," Biomater. Sci., 4(8):1161-1183, (2016).
Wold et al., "Fabrication of Biodegradable Polymeric Nanofibers with Covalently Attached NO Donors," ACS Appl. Mater. Interfaces, 4(6):3022-3030, (2012).
Worley et al., "Anti-Biofilm Efficacy of Dual-Action Nitric Oxide-Releasing Alkyl Chain Modified Poly(amidoamine) Dendrimers," Mol. Pharmaceutics, 12:1573-1583, (2015).
Wu et al., "'Living' controlled in situ gelling systems: thiol-disulfide exchange method toward tailor-made biodegradable hydrogels," J. Am. Chem. Soc., 132(43):15140-15143, (2010).
Xu et al., "Well-defined poly (2-hydroxyl-3-(2-hydroxyethylamino) propyl methacrylate) vectors with low toxicity and high gene transfection efficiency," Biomacromolecules, 11 (6): 1437-1442, (2010).
Yang et al., "S-Nitrosothiol-modified hyperbranched polyesters," Polym. Chem., 7(46):7161-7169, (2016).
Zhang et al., "A physical gel made from hyperbranched polymer gelator," Chem. Commun., 25:2587-2589, (2007).
Zhang et al., "Antibacterial cotton fabric grafted with silver nanoparticles and its excellent laundering durability," Carbohydr. Polym., 92(2):2088-2094, (2013).
Zhang et al., "Synthesis of an amino-terminated hyperbranched polymer and its application in reactive dyeing on cotton as a salt-free dyeing auxiliary," Color. Technol., 123(6):351-357, (2007).
Zhang et al., "The antimicrobial activity of the cotton fabric grafted with an amino-terminated hyperbranched polymer," Cellulose, 16:281-288, (2009).

(56) References Cited

OTHER PUBLICATIONS

Zheng et al., "Hyperbranched polymers: Advances from synthesis to applications," Chemical Society Reviews, 44(12):4091-4130, (2015).
Zhu et al., "Influence of Branching Architecture on Polymer Properties," Journal of Polymer Science Part B: Polymer Physics, 49(18):1277-1286, (2011).

* cited by examiner

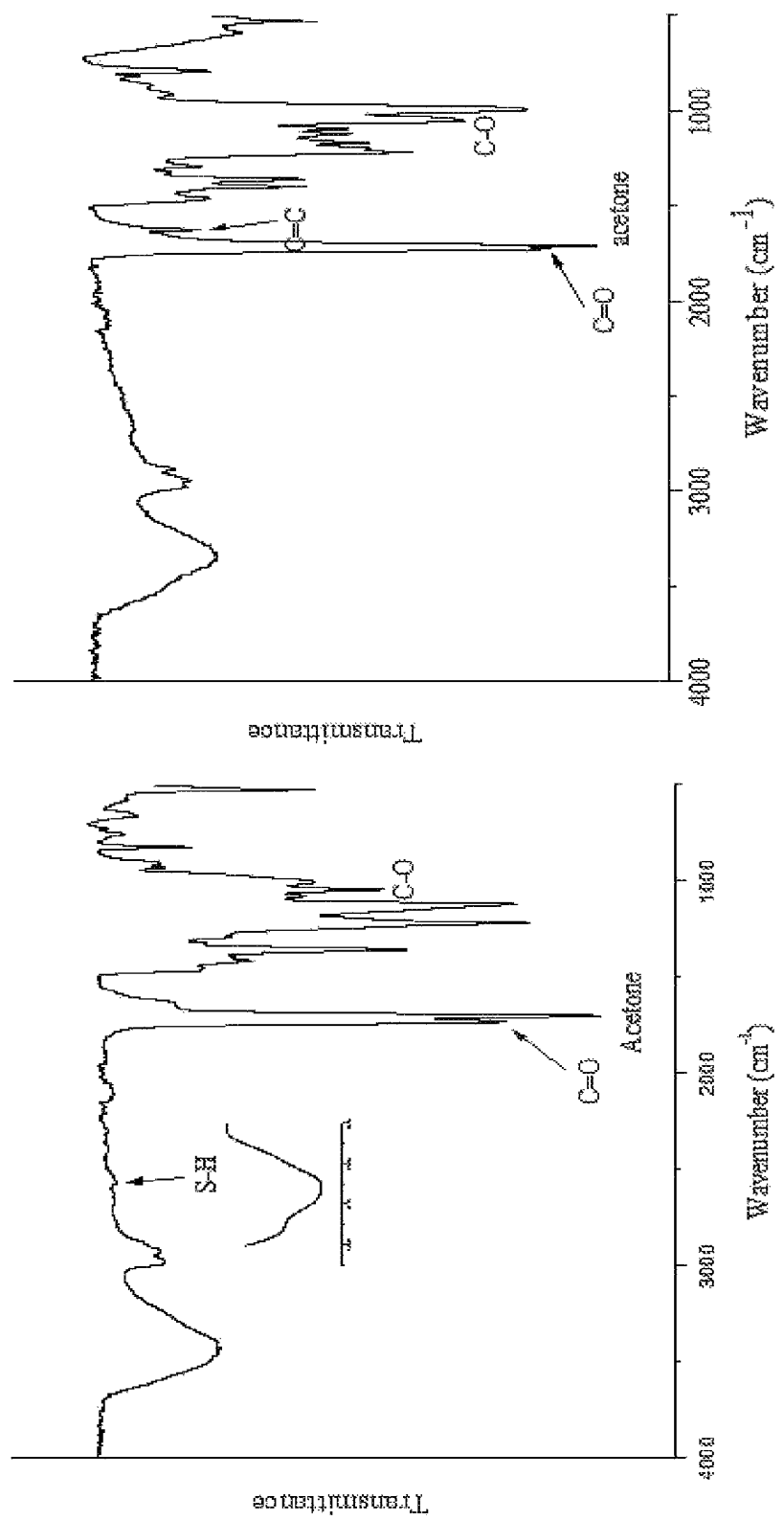

S-NITROSOTHIOL-MEDIATED HYPERBRANCHED POLYESTERS

CROSS-REFERENCE TO RELATED APPLICATIONS

This Application claims the benefit of U.S. Provisional Application No. 62/405,655, filed on Oct. 7, 2016, which is incorporated herein by reference in its entirety.

STATEMENT REGARDING FEDERALLY SPONSORED RESEARCH

This invention was made with government support under Grant No. DE025207 awarded by the National Institutes of Health (NIH). The government has certain rights in the invention.

BACKGROUND

Nitric oxide (NO) is an endogenously produced diatomic free radical that mediates angiogenesis (J. P. Cooke, *Atherosclerosis Suppl.*, 2003, 4, 53-600, blood pressure regulation (D. D. Rees, R. M. Palmer and S. Moncada, *Proc. Natl. Acad. Sci.*, 1989, 86, 3375-3378), wound healing (J.-d. Luo and A. F. Chen, *Acta Pharmacol. Sin.*, 2005, 26, 259-264; M. R. Schäffer, U. Tantry, S. S. Gross, H. L. Wasserkrug and A. Barbul, *J. Surg. Res.*, 1996, 63, 237-240), and the immune response (C. Bogdan, *Nat. Immunol.*, 2001, 2, 907-916; J. MacMicking, Q.-w. Xie and C. Nathan, *Annu. Rev. Immunol.*, 1997, 15, 323-350). Due to its relatively short biological half-life (seconds) and reactive nature, the synthesis of scaffolds capable of controlled NO storage and release is important for helping further understand NO's role in physiology and developing NO-based therapeutics (A. W. Carpenter and M. H. Schoenfisch, *Chem. Soc. Rev.*, 2012, 41, 3742-3752; P. N. Coneski and M. H. Schoenfisch, *Chem. Soc. Rev.*, 2012, 41, 3753-3758; S. P. Nichols, W. L. Storm, A. Koh and M. H. Schoenfisch, *Adv. Drug Delivery Rev.*, 2012, 64, 1177-1188; D. A. Riccio and M. H. Schoenfisch, *Chem. Soc. Rev.*, 2012, 41, 3731-3741). To date, N-diazeniumdiolates and S-nitrosothiols (RSNOs) represent the most widely employed NO donors because of their spontaneous NO-release characteristics under physiological conditions (pH 7.4, 37° C.) (D. A. Riccio and M. H. Schoenfisch, *Chem. Soc. Rev.*, 2012, 41, 3731-3741). S-Nitrosothiol-based NO donors are attractive as potential therapeutics due to their low toxicity and endogenous nature (P. N. Coneski and M. H. Schoenfisch, Poly. Chem., 2011, 2, 906-913). S-Nitrosothiols are readily synthesized via the reaction of free thiols with nitrosating agents (e.g., $NaNO_2$/HCl). The ensuing NO release is tunable and triggered via several decomposition pathways, including exposure to light, heat, and copper ions (D. Lyn H Williams, *Chem. Soc. Rev.*, 1985, 14, 171-196).

Recent research has focused on the synthesis of macromolecular NO-release scaffolds to enhance NO payloads and enable greater tunability of the NO-release kinetics relative to that achieved using small molecule NO donors (H. P. Zhang, G. M. Annich, J. Miskulin, K. Stankiewicz, K. Osterholzer, S. I. Merz, R. H. Bartlett and M. E. Meyerhoff, *J. Am. Chem. Soc.*, 2003, 125, 5015-5024; Y. Lu, D. L. Slomberg, B. Sun and M. H. Schoenfisch, *Small*, 2013, 9, 2189-2198.; D. L. Slomberg, Y. Lu, A. D. Broadnax, R. A. Hunter, A. W. Carpenter and M. H. Schoenfisch, *ACS Appl. Mater. Interfaces*, 2013, 5, 9322-9329; Y. Lu, D. L. Slomberg, A. Shah and M. H. Schoenfisch, *Biomacromolecules*, 2013, 14, 3589-3598; B. Sun, D. L. Slomberg, S. L. Chudasama, Y. Lu and M. H. Schoenfisch, *Biomacromolecules*, 2012, 13, 3343-3354; Y. Lu, B. Sun, C. Li and M. H. Schoenfisch, *Chem. Mater.*, 2011, 23, 4227-4233; E. M. Hetrick, J. H. Shin, N. A. Stasko, C. B. Johnson, D. A. Wespe, E. Holmuhamedov and M. H. Schoenfisch, *ACS Nano*, 2008, 2, 235-246; Z. R. Zhou, G. M. Annich, Y. D. Wu and M. E. Meyerhoff, *Biomacromolecules*, 2006, 7, 2565-2574; M. C. Frost and M. E. Meyerhoff, *J. Biomed. Mater. Res., Part A*, 2005, 72A, 409-419; N. A. Stasko, T. H. Fischer and M. H. Schoenfisch, *Biomacromolecules*, 2008, 9, 834-841; R. J. Soto, L. Yang and M. H. Schoenfisch, *ACS Appl. Mater. Interfaces*, 2016, 8, 2220-2231; B. V. Worley, D. L. Slomberg and M. H. Schoenfisch, *Bioconjugate Chem.*, 2014, 25, 918-927; T. Liu, W. Zhang, X. Yang and C. Li, *J. Colloid Interface Sci.*, 2015, 459, 115-122). Dendritic polymeric scaffolds exhibit attractive characteristics as macromolecular scaffolds due to their high density of exterior functional groups available for further modifications (Y. Lu, D. L. Slomberg, A. Shah and M. H. Schoenfisch, *Biomacromolecules*, 2013, 14, 3589-3598; B. Sun, D. L. Slomberg, S. L. Chudasama, Y. Lu and M. H. Schoenfisch, *Biomacromolecules*, 2012, 13, 3343-3354; N. A. Stasko, T. H. Fischer and M. H. Schoenfisch, *Biomacromolecules*, 2008, 9, 834-841; B. V. Worley, D. L. Slomberg and M. H. Schoenfisch, *Bioconjugate Chem.*, 2014, 25, 918-927). For example, polyamidoamine (PAMAM) dendrimers functionalized with RSNOs demonstrated large NO storage and tunable NO release kinetics by simply varying the steric structure of the thiol modification. Thiols with a compact structure exhibited extended NO-release kinetics compared to branched thiol structures (N. A. Stasko, T. H. Fischer and M. H. Schoenfisch, *Biomacromolecules*, 2008, 9, 834-841). While these NO-releasing dendrimers displayed antiplatelet activity, the scaffold toxicity against mammalian cells and poor biodegradability may hinder their utility for certain biomedical applications (N. A. Stasko, T. H. Fischer and M. H. Schoenfisch, *Biomacromolecules*, 2008, 9, 834-841).

Polyesters represent an alternative polymeric NO-release scaffold with potentially useful biodegradation properties (T. Liu, W. Zhang, X. Yang and C. Li, *J. Colloid Interface Sci.*, 2015, 459, 115-122; P. N. Coneski, K. S. Rao and M. H. Schoenfisch, *Biomacromolecules*, 2010, 11, 3208-3215; V. B. Damodaran and M. M. Reynolds, *J. Mater. Chem.*, 2011, 21, 5870-5872; A. B. Seabra, D. Martins, M. M. S. G. Simoes, R. da Silva, M. Brocchi and M. G. de Oliveira, *Artif. Organs*, 2010, 34, E204-E214). Seabra et al. reported the synthesis of S-nitrosothiol-modified polyesters via the condensation of 3-mercapto-1,2-propanediol and mercaptosuccinic acid, followed by a nitrosation reaction (A. B. Seabra, D. Martins, M. M. S. G. Simoes, R. da Silva, M. Brocchi and M. G. de Oliveira, *Artif. Organs*, 2010, 34, E204-E214). The resulting NO donor-modified polyesters were blended with poly(methyl methacrylate) to yield coatings that released ~40 nmol NO $cm^{-2}$ over 72 h. Yapor et al. subsequently developed citrate-based S-nitrosothiol-modified polyesters capable of storing ~0.45 µmol NO $mg^{-1}$ polymer (J. P. Yapor, A. Lutzke, A. Pegalajar-Jurado, B. H. Neufeld, V. B. Damodaran and M. M. Reynolds, *J. Mater. Chem. B*, 2015, 3, 9233-9241). Of practical relevance, the tedious material preparation and relatively low NO storage capacities of these scaffolds limit their utility.

Hyperbranched polyesters are a family of polymers with multivalent structures and diverse exterior functionalities (B. I. Voit and A. Lederer, *Chem. Rev.*, 2009, 109, 5924-5973). In contrast to their dendrimer counterparts, the synthesis of hyperbranched polyesters is more straightforward as they proceed via one-pot reactions (B. I. Voit and A.

Lederer, *Chem. Rev.*, 2009, 109, 5924-5973). Bis(hydroxymethyl)propionic acid (bis-MPA) has been widely utilized as a building unit in creating hyperbranched polyesters with a high density of modifiable exterior hydroxyl groups and good solubility in organic solvents for subsequent chemical functionalization steps (Y. L. Xiao, H. Hong, A. Javadi, J. W. Engle, W. J. Xu, Y. A. Yang, Y. Zhang, T. E. Barnhart, W. B. Cai and S. Q. Gong, *Biomaterials*, 2012, 33, 3071-3082; N. Feliu, M. V. Walter, M. I. Montanez, A. Kunzmann, A. Hult, A. Nystrom, M. Malkoch and B. Fadeel, *Biomaterials*, 2012, 33, 1970-1981; A. Carlmark, E. Malmstrom and M. Malkoch, *Chem. Soc. Rev.*, 2013, 42, 5858-5879; E. Malmström, M. Johansson and A. Hult, *Macromolecules*, 1995, 28, 1698-1703). Easy synthesis, biodegradability, and solubility in organic solvents have led many research groups to evaluate the potential of these polymers for biomedical application (Y. L. Xiao, H. Hong, A. Javadi, J. W. Engle, W. J. Xu, Y. A. Yang, Y. Zhang, T. E. Barnhart, W. B. Cai and S. Q. Gong, *Biomaterials*, 2012, 33, 3071-3082; N. Feliu, M. V. Walter, M. I. Montanez, A. Kunzmann, A. Hult, A. Nystrom, M. Malkoch and B. Fadeel, *Biomaterials*, 2012, 33, 1970-1981; M. Prabaharan, J. J. Grailer, S. Pilla, D. A. Steeber and S. Q. Gong, *Biomaterials*, 2009, 30, 5757-5766; X. H. Zeng, Y. N. Zhang and A. M. Nystrom, *Biomacromolecules*, 2012, 13, 3814-3822; K. Karatasos, *J. Phys. Chem. B*, 2013, 117, 2564-2575). For example, Feliu et al. demonstrated that bis-MPA-based polyesters exhibited excellent biodegradability and were non-toxic compared to PAMAM dendrimers (N. Feliu, M. V. Walter, M. I. Montanez, A. Kunzmann, A. Hult, A. Nystrom, M. Malkoch and B. Fadeel, *Biomaterials*, 2012, 33, 1970-1981). Based on these two characteristics, bis-MPA-based hyperbranched polyesters are now being utilized for cancer-targeted drug delivery and non-invasive positron emission tomography (PET) imaging applications (Y. L. Xiao, H. Hong, A. Javadi, J. W. Engle, W. J. Xu, Y. A. Yang, Y. Zhang, T. E. Barnhart, W. B. Cai and S. Q. Gong, *Biomaterials*, 2012, 33, 3071-3082). The facile chemical modification and excellent biocompatibility of bis-MPA-based hyperbranched polyesters suggest that they may be useful for NO-release applications.

Despite the interest in hyperbranched polyesters for biomedical applications due to the ease of synthesis, biodegradability, and solubility of these polymers, the development and use of hyperbranched polyesters for NO-release applications has remained elusive. Accordingly, there remains a need for NO-donor modified hyperbranched polymers and methods of making and using same.

SUMMARY

In accordance with the purpose(s) of the invention, as embodied and broadly described herein, the invention, in one aspect, relates to degradable polymers useful in, for example, delivering nitric oxide to a target and/or treating a disorder in a subject.

Disclosed are degradable polymers comprising: (a) a biodegradable polymer backbone; (b) at least one nitric oxide linker moiety pendant from the polymer backbone; and (c) at least one nitric oxide molecule covalently bonded to the nitric oxide linker moiety.

Also disclosed are polymers comprising: (a) a biodegradable polymer backbone; and (b) at least one nitric oxide linker moiety pendant from the polymer backbone.

Also disclosed are methods of making a polymer, the method comprising: (a) reacting a polymer comprising at least one hydroxyl group and acryloyl halide to form a vinyl-functionalized polymer; and (b) reacting the vinyl-functionalized polymer with a dinucleophile to form a polymer scaffold, thereby making the polymer.

Also disclosed are methods of making a degradable polymer, the method comprising the step of functionalizing a polymer scaffold with a nitric oxide donor, wherein the polymer scaffold comprises: (a) a biodegradable polymer backbone; and (b) at least one nitric oxide linker moiety pendant from the polymer backbone, thereby making the degradable polymer.

Also disclosed are methods of delivering nitric oxide to a target, the method comprising: (a) administering to the target an effective amount of a degradable polymer comprising: (i) a biodegradable polymer backbone; (ii) at least one nitric oxide linker moiety pendant from the polymer backbone; and (iii) at least one nitric oxide molecule covalently bonded to the nitric oxide linker moiety; and (b) exposing the degradable polymer to at least one of heat, light, copper, a free thiol, and/or a proton source, thereby delivering nitric oxide to the target.

Also disclosed are methods for the treatment of a disorder in a subject, the method comprising the step of administering to the subject an effective amount of a degradable polymer comprising: (a) a biodegradable polymer backbone; (b) at least one nitric oxide linker moiety pendant from the polymer backbone; and (c) at least one nitric oxide molecule covalently bonded to the nitric oxide linker moiety.

Also disclosed are medical devices comprising a nitric oxide-releasing polymeric film, wherein the polymer film comprises an effective amount of at least one polymer comprising: (a) a polymer backbone; (b) at least one nitric oxide linker moiety pendant from the polymer backbone; and (c) at least one nitric oxide molecule covalently bonded to the nitric oxide linker moiety.

Also disclosed are pharmaceutical compositions comprising a therapeutically effective amount of at least one degradable polymer comprising: (a) a biodegradable polymer backbone; (b) at least one nitric oxide linker moiety pendant from the polymer backbone; and (c) at least one nitric oxide molecule covalently bonded to the nitric oxide linker moiety, or a pharmaceutically acceptable salt thereof, and a pharmaceutically acceptable carrier.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 8A-D show representative FTIR spectra for G3-HP-DTT (8A), G3-HP-AC (8B), G3-HP-DTT/NO (8C), and nitrosated G3-HP-AC (8D).

Figure 1:
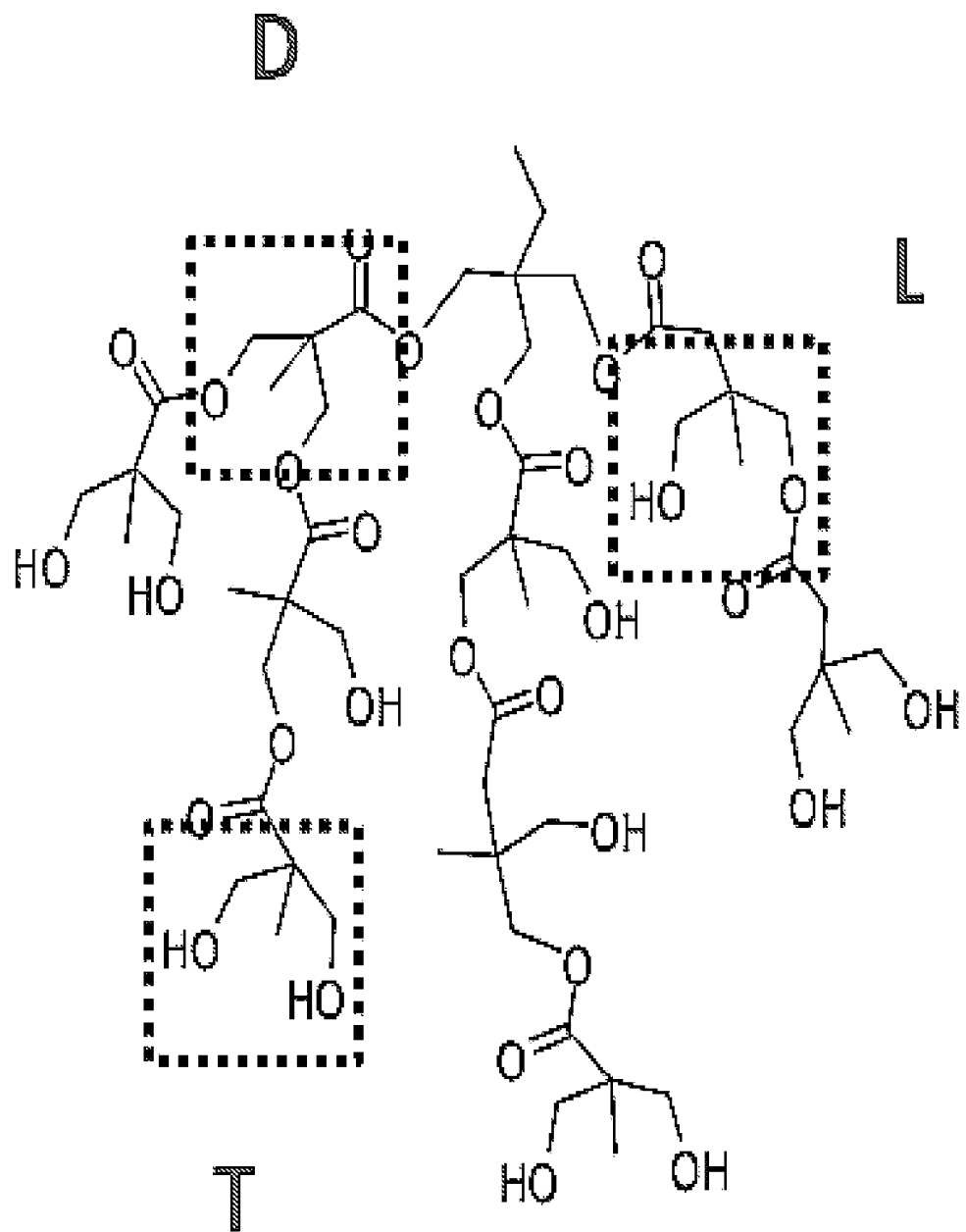
FIG. 1 shows a representative image illustrating the structure of a hyperbranched polymer consisting of three different structural units—dendritic (D), linear (L), and terminal (T).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "catalytically effective" refers to the amount of a catalyst that is sufficient to facilitate a reaction (e.g., atom-transfer radical polymerization as disclosed herein).

As used herein, the term "polymer" refers to a relatively high molecular weight organic compound, natural or synthetic, whose structure can be represented by a repeated small unit, the monomer (e.g., monomethacryloxypropyl terminated polydimethylsiloxane.). Synthetic polymers are typically formed by addition or condensation polymerization of monomers.

As used herein, the term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers.

As used herein, the term "molecular weight" (MW) refers to the mass of one molecule of that substance, relative to the unified atomic mass unit u (equal to $1/12$ the mass of one atom of carbon-12).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA'$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A' or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide", as used herein can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, indolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The term "heterocycle," as used herein refers to single and multi-cyclic aromatic or non-aromatic ring systems in which at least one of the ring members is other than carbon. Heterocycle includes pyridinde, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula A$^1$C(O)A$^2$, where A$^1$ and A$^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —N$_3$.

The term "nitro" as used herein is represented by the formula —NO$_2$.

The term "nitrile" or "cyano" as used herein is represented by the formula —CN.

The term "thiol" as used herein is represented by the formula —S— or —SH.

"R$^1$," "R$^2$," "R$^3$," "R$^n$," where n is an integer, as used herein can, independently, possess one or more of the groups listed above. For example, if R$^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group is independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-1}Ph$, which may be substituted with $R^\circ$; —$(CH_2)_{0-4}O(CH_2)_{0-4}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, $SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched)alkylene)O—$N(R^\circ_2$; or —$(C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), is independently halogen, —$(CH_2)_{0-2}R^\bullet$, -(halo$R^\bullet$), —$(CH_2)_{0-2}OH$, —$(CH_2)_{0-2}OR^\bullet$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{02}NH_2$, —$(CH_2)_{0-2}NHR^\bullet$, —$(CH_2)_{0-2}NR^\bullet_2$, —$NO_2$, —$C(O)SR^\bullet$, —$(C_{1-4}$ straight or branched alkylene)C(O)OR$^\bullet$, or —$SSR^\bullet$ wherein each $R^\bullet$ is unsubstituted or where preceded by "halo" is substituted only with one or more halogens, and is independently selected from $C_1$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —$R^\bullet$, -(halo$R^\bullet$), —OH, —$OR^\bullet$, —O(halo$R^\bullet$), —CN, —C(O)OH, —C(O)O$R^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —$C(O)R^\dagger$, —$C(O)OR^\dagger$, —$C(O)C(O)R^\dagger$, —$C(O)CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ is independently halogen, —$R^\bullet$, -(halo$R^\bullet$), —OH, —$OR^\bullet$, —O(halo$R^\bullet$), —CN, —C(O)OH, —C(O)O$R^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure

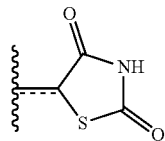

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

It is also appreciated that certain compounds described herein can be present as an equilibrium of tautomers. For example, ketones with an α-hydrogen can exist in an equilibrium of the keto form and the enol form.

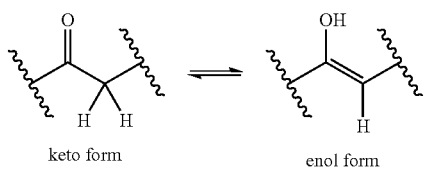

keto form          enol form

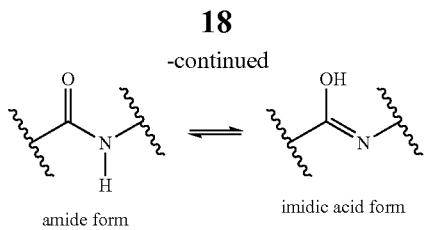

amide form          imidic acid form

Likewise, amides with an N-hydrogen can exist in an equilibrium of the amide form and the imidic acid form. As another example, pyrazoles can exist in two tautomeric forms, N$^1$-unsubstituted, 3-A$^3$ and N$^1$-unsubstituted, 5-A$^3$ as shown below.

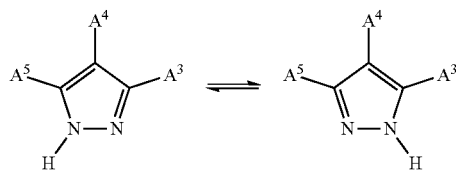

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

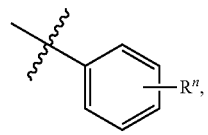

which is understood to be equivalent to a formula:

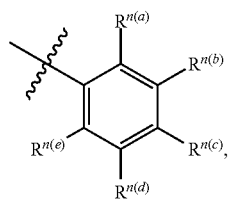

wherein n is typically an integer. That is, R$^n$ is understood to represent five independent substituents, R$^{n(a)}$, R$^{n(b)}$, R$^{n(c)}$, R$^{n(d)}$, R$^{n(e)}$. By "independent substituents," it is meant that each R substituent can be independently defined. For example, if in one instance R$^{n(a)}$ is halogen, then R$^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental Volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B—F, C-D, C-E, and C—F are considered disclosed. Likewise, any subset or combination of these is also disclosed. Thus, for example, the sub-group of A-E, B—F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Degradable Polymers

In one aspect, disclosed are degradable polymers comprising: (a) a biodegradable polymer backbone; (b) at least one nitric oxide linker moiety pendant from the polymer backbone; and (c) at least one nitric oxide molecule covalently bonded to the nitric oxide linker moiety. Without wishing to be bound by theory, a degradable polymer refers to a polymer that can be broken in a biological or non-biological environment in response to a stimulus. Examples of stimuli include, but are not limited to, heat, light, copper ions, and free thiols.

In one aspect, disclosed are polymers comprising: (a) a biodegradable polymer backbone; and (b) at least one nitric oxide linker moiety pendant from the polymer backbone.

In a further aspect, the degradable polymer is hyperbranched. In a still further aspect, the polymer is hyperbranched. Without wishing to be bound by theory, a hyperbranched polymer refers to a polymer having a densely branched structure that is imperfectly branched or irregular. In various aspects, a hyperbranched polymer has a higher functional group density per molecular unit than a straight-chain polymer or a conventional branched polymer. In various further aspects, a hyperbranched polymer that has been elaborated to several generations has an internal space. These characteristics make hyperbranched polymers attractive for a variety of applications including, but not limited to, surfactants, gelling agents, drug delivery systems, and polymeric absorbents.

1. Biodegradable Polymer Backbones

In one aspect, disclosed are degradable polymers comprising a biodegradable polymer backbone.

In a further aspect, the polymer backbone is a polyester backbone.

In a further aspect, the polymer backbone comprises at least one polyester residue.

In a further aspect, the polymer backbone comprises at least one residue having a structure represented by a formula selected from:

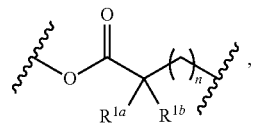

wherein each occurrence of n is independently selected from 0, 1, 2, 3, or 4; wherein each of $R^{1a}$ and $R^{1b}$ is independently selected from —OH, C1-C4 alkyl, C1-C4 hydroxyalkyl, and —$(CH_2)_n$OC(O)L, provided that at least one of $R^{1a}$ and $R^{1b}$ is —$(CH_2)_n$OC(O)L; and wherein L is the nitric oxide linker moiety.

In a further aspect, the polymer backbone comprises at least one residue having a structure represented by a formula selected from:

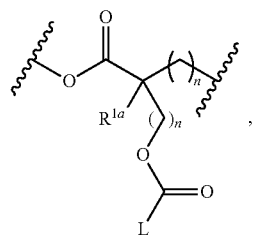

wherein each occurrence of n is independently selected from 0, 1, 2, 3, or 4; wherein $R^{1a}$ is selected from —OH, C1-C4 alkyl, C1-C4 hydroxyalkyl, and —(CH$_2$)$_n$OC(O)L; and wherein L is the nitric oxide linker moiety.

In a further aspect, the polymer backbone comprises at least one residue having a structure represented by a formula selected from:

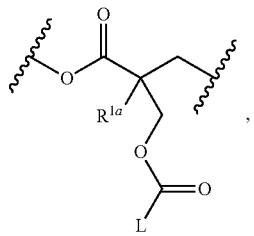

wherein $R^{1a}$ is selected from —OH, C1-C4 alkyl, C1-C4 hydroxyalkyl, and —(CH$_2$)$_n$OC(O)L; and wherein L is the nitric oxide linker moiety.

In a further aspect, the polymer backbone comprises at least one residue having a structure:

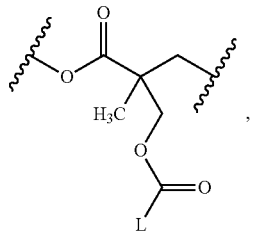

wherein L is the nitric oxide linker moiety.

In a further aspect, the at least one residue is present as a repeating unit.

In a further aspect, each occurrence of n is independently selected from 0, 1, 2, 3, or 4. In a still further aspect, each occurrence of n is independently selected from 0, 1, 2, or 3. In yet a further aspect, each occurrence of n is independently selected from 0, 1, or 2. In an even further aspect, each occurrence of n is independently selected from 0 or 1. In a still further aspect, each occurrence of n is 4. In yet a further aspect, each occurrence of n is 3. In an even further aspect, each occurrence of n is 2. In a still further aspect, each occurrence of n is 1. In an even further aspect, each occurrence of n is 0.

In a further aspect, L is the nitric oxide linker moiety.

a. $R^{1A}$ and $R^{1B}$ Groups

In one aspect, each of $R^{1a}$ and $R^{1b}$ is independently selected from —OH, C1-C4 alkyl, C1-C4 hydroxyalkyl, and —(CH$_2$)$_n$OC(O)L, provided that at least one of $R^{1a}$ and $R^{1b}$ is —(CH$_2$)$_n$OC(O)L.

In a further aspect, $R^{1a}$ is —(CH$_2$)$_n$OC(O)L and $R^{1b}$ is selected from —OH, C1-C4 alkyl, C1-C4 hydroxyalkyl, and —(CH$_2$)$_n$OC(O)L. In a still further aspect, $R^{1a}$ is —(CH$_2$)$_n$OC(O)L and $R^{1b}$ is selected from —OH, methyl, ethyl, n-propyl, i-propyl, —CH$_2$OH, —CH$_2$CH$_2$OH, —CH$_2$CH$_2$CH$_2$OH, —CH(CH$_3$)(CH$_2$OH), and —(CH$_2$)$_n$OC(O)L. In yet a further aspect, $R^{1a}$ is —(CH$_2$)$_n$OC(O)L and $R^{1b}$ is selected from —OH, methyl, ethyl, —CH$_2$OH, —CH$_2$CH$_2$OH, and —(CH$_2$)$_n$OC(O)L. In an even further aspect, $R^{1a}$ is —(CH$_2$)$_n$OC(O)L and $R^{1b}$ is selected from —OH, methyl, —CH$_2$OH, and —(CH$_2$)$_n$OC(O)L.

In a further aspect, $R^{1a}$ is —(CH$_2$)$_n$OC(O)L and $R^{1b}$ is selected from —OH, C1-C4 alkyl, and C1-C4 hydroxyalkyl. In a still further aspect, $R^{1a}$ is —(CH$_2$)$_n$OC(O)L and $R^{1b}$ is selected from —OH, methyl, ethyl, n-propyl, i-propyl, —CH$_2$OH, —CH$_2$CH$_2$OH, —CH$_2$CH$_2$CH$_2$OH, and —CH(CH$_3$)(CH$_2$OH). In yet a further aspect, $R^{1a}$ is —(CH$_2$)$_n$OC(O)L and $R^{1b}$ is selected from —OH, methyl, ethyl, —CH$_2$OH, and —CH$_2$CH$_2$OH. In an even further aspect, $R^{1a}$ is —(CH$_2$)$_n$OC(O)L and $R^{1b}$ is selected from —OH, methyl, and —CH$_2$OH. In a still further aspect, $R^{1a}$ is —(CH$_2$)$_n$OC(O)L and $R^{1b}$ is —OH. In yet a further aspect, $R^{1a}$ is —(CH$_2$)$_n$OC(O)L and $R^{1b}$ is methyl. In an even further aspect, $R^{1a}$ is —(CH$_2$)$_n$OC(O)L and $R^{1b}$ is —CH$_2$OH.

In a further aspect, each of $R^{1a}$ and $R^{1b}$ is —(CH$_2$)$_n$OC(O)L.

2. Nitric Oxide Linker Moieties

In one aspect, disclosed are degradable polymers comprising at least one nitric oxide linker moiety pendant from the polymer backbone.

In a further aspect, the nitric oxide linker moiety comprises a dithiol. In a still further aspect, the nitric oxide linker moiety comprises a diamine. In yet a further aspect, the nitric oxide linker moiety comprises a single amine such as, for example, hexyl amine.

In a further aspect, the nitric oxide linker moiety is present in an amount of no more than about 2.0 μmol/mg. In a still further aspect, the nitric oxide linker moiety is present in an amount of less than about 2.0 μmol/mg. In yet a further aspect, the nitric oxide linker moiety is present in an amount of less than about 1.75 μmol/mg. In an even further aspect, the nitric oxide linker moiety is present in an amount of less than about 1.5 μmol/mg. In a still further aspect, the nitric oxide linker moiety is present in an amount of less than about 1.25 μmol/mg. In yet a further aspect, the nitric oxide linker moiety is present in an amount of less than about 1.0 μmol/mg. In an even further aspect, the nitric oxide linker moiety is present in an amount of about 2.0 μmol/mg.

In a further aspect, the nitric oxide linker moiety is present in an amount of from about 0.1 μmol/mg to about 2.0 μmol/mg. In a still further aspect, the nitric oxide linker moiety is present in an amount of from about 0.5 μmol/mg to about 2.0 μmol/mg. In yet a further aspect, the nitric oxide linker moiety is present in an amount of from about 1.0 μmol/mg to about 2.0 μmol/mg. In an even further aspect, the nitric oxide linker moiety is present in an amount of from about 1.5 μmol/mg to about 2.0 μmol/mg. In a still further aspect, the nitric oxide linker moiety is present in an amount of from about 0.1 μmol/mg to about 1.5 μmol/mg. In yet a further aspect, the nitric oxide linker moiety is present in an amount of from about 0.1 μmol/mg to about 1.0 μmol/mg. In an even further aspect, the nitric oxide linker moiety is present in an amount of from about 0.1 μmol/mg to about 0.5 μmol/mg.

In a further aspect, the nitric oxide linker moiety has a structure represented by a formula:

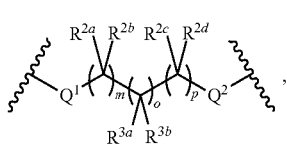

wherein each of m, o, and p is independently selected from 1, 2, 3, and 4; wherein each of $Q^1$ and $Q^2$ is independently selected from S and $NR^4$; wherein each occurrence of $R^4$, when present, is independently selected from hydrogen, C1-C4 alkyl, and a protecting group; and wherein each occurrence of $R^{2a}$, $R^{2b}$, $R^{2c}$, and $R^{2d}$ is independently selected from hydrogen and C1-C4 alkyl; wherein each occurrence of $R^{3a}$ and $R^{3b}$ is independently selected from hydrogen, —$OR^5$, and C1-C4 alkyl; and wherein $R^5$, when present, is selected from hydrogen, C1-C4 alkyl, and an alcohol protecting group.

In a further aspect, the nitric oxide linker moiety has a structure represented by a formula:

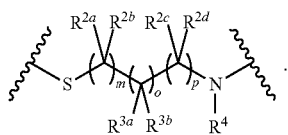

In a further aspect, the nitric oxide linker moiety has a structure represented by a formula:

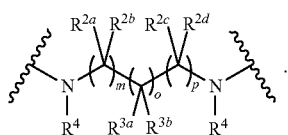

In a further aspect, the nitric oxide linker moiety has a structure represented by a formula:

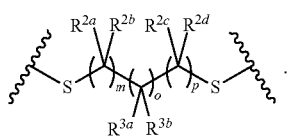

In a further aspect, the nitric oxide linker moiety has a structure selected from:

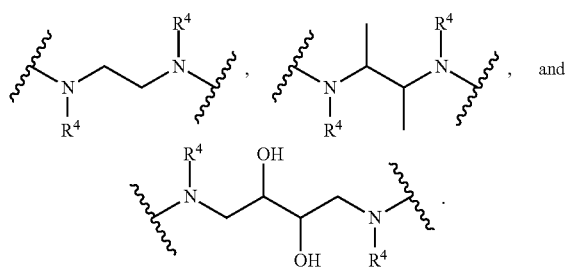

In a further aspect, the nitric oxide linker moiety has a structure selected from:

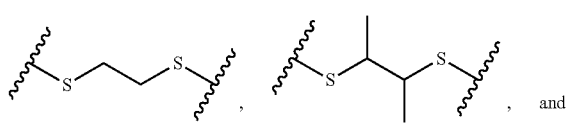

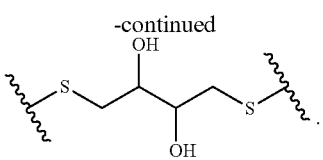

In a further aspect, the nitric oxide linker moiety has a structure represented by a formula:

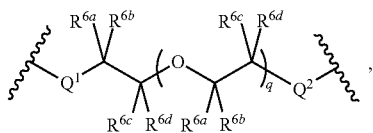

wherein q is selected from 1, 2, 3, and 4; wherein each of $Q^1$ and $Q^2$ is independently selected]from S and $NR^4$; wherein each occurrence of $R^4$, when present, is independently selected from hydrogen, C1-C4 alkyl, and a protecting group; and wherein each occurrence of $R^{6a}$, $R^{6b}$, $R^{6c}$, and $R^{6d}$ is independently selected from hydrogen and C1-C4 alkyl.

In a further aspect, the nitric oxide linker moiety has a structure represented by a formula:

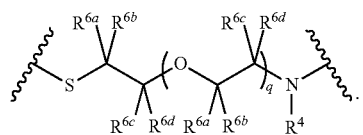

In a further aspect, the nitric oxide linker moiety has a structure represented by a formula:

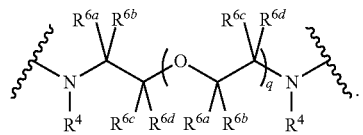

In a further aspect, the nitric oxide linker moiety has a structure represented by a formula:

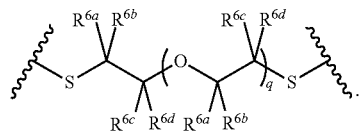

In a further aspect, the nitric oxide linker moiety has a structure represented by a formula:

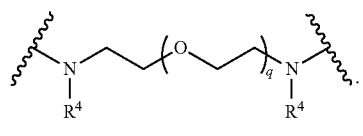

In a further aspect, the nitric oxide linker moiety has a structure represented by a formula:

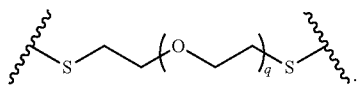

In a further aspect, the nitric oxide linker moiety has a structure represented by a formula:

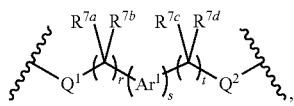

wherein each of r and t is independently selected from 0 and 1; wherein s is selected from 1, 2, and 3; wherein each of $Q^1$ and $Q^2$ is independently selected from S and $NR^4$; wherein each occurrence of $R^4$, when present, is independently selected from hydrogen, C1-C4 alkyl, and a protecting group; wherein each occurrence of $R^{7a}$, $R^{7b}$, $R^{7c}$, and $R^{7d}$ is independently selected from hydrogen and C1-C4 alkyl; and wherein each occurrence of $Ar^1$ is independently selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl.

In a further aspect, the nitric oxide linker moiety has a structure represented by a formula:

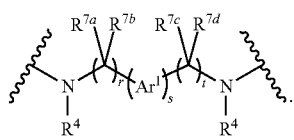

In a further aspect, the nitric oxide linker moiety has a structure represented by a formula:

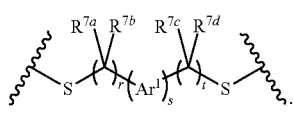

In a further aspect, the nitric oxide linker moiety has a structure represented by a formula:

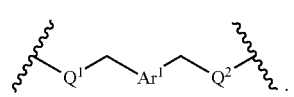

In a further aspect, the nitric oxide linker moiety has a structure represented by a formula:

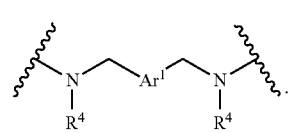

In a further aspect, the nitric oxide linker moiety has a structure represented by a formula:

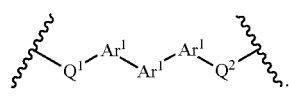

In a further aspect, the nitric oxide linker moiety has a structure represented by a formula:

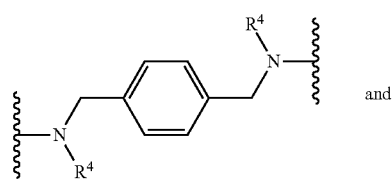

In a further aspect, the nitric oxide linker moiety has a structure represented by a formula:

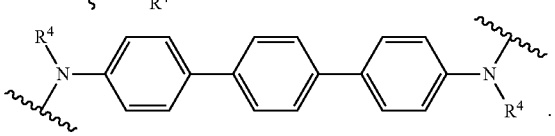

In a further aspect, the nitric oxide linker moiety has a structure selected from:

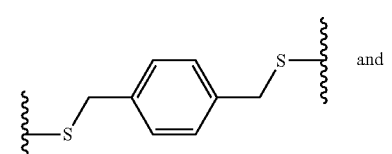

and

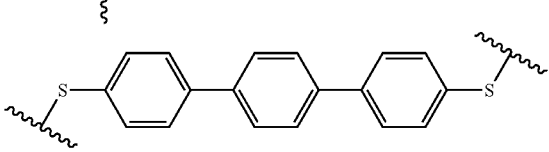

In a further aspect, the nitric oxide linker moiety has a structure selected from:

In a further aspect, the nitric oxide linker moiety has a structure represented by a formula:

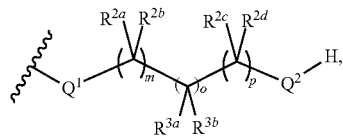

wherein each of m, o, and p is independently selected from 1, 2, 3, and 4; wherein each of $Q^1$ and $Q^2$ is independently selected from S and $NR^4$; wherein each occurrence of $R^4$, when present, is independently selected from hydrogen, C1-C4 alkyl, and a protecting group; wherein each occurrence of $R^{2a}$, $R^{2b}$, $R^{2c}$, and $R^{2d}$ is independently selected from hydrogen and C1-C4 alkyl; wherein each occurrence of $R^{3a}$ and $R^{3b}$ is independently selected from hydrogen, —$OR^5$, and C1-C4 alkyl; and wherein $R^5$ is selected from hydrogen, C1-C4 alkyl, and an alcohol protecting group.

In a further aspect, the nitric oxide linker moiety has a structure represented by a formula:

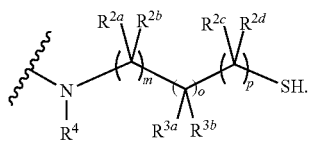

In a further aspect, the nitric oxide linker moiety has a structure represented by a formula:

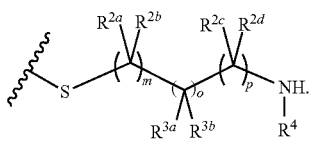

In a further aspect, the nitric oxide linker moiety has a structure represented by a formula:

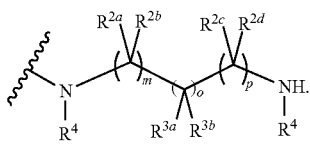

In a further aspect, the nitric oxide linker moiety has a structure represented by a formula:

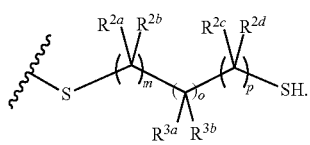

In a further aspect, the nitric oxide linker moiety has a structure selected from:

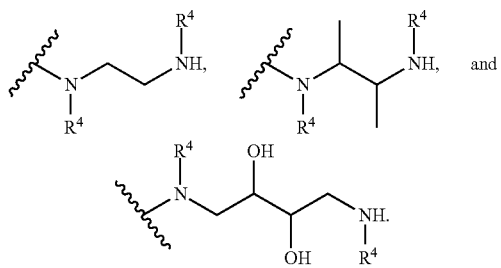

In a further aspect, the nitric oxide linker moiety has a structure selected from:

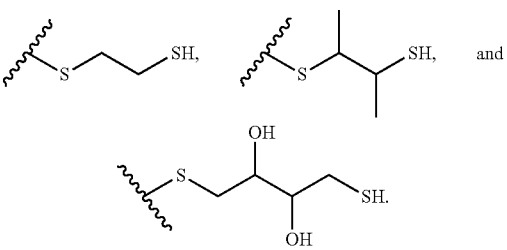

In a further aspect, the nitric oxide linker moiety has a structure represented by a formula:

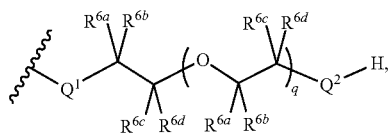

wherein q is selected from 1, 2, 3, and 4; wherein each of $Q^1$ and $Q^2$ is independently selected from S and $NR^4$; wherein each occurrence of $R^4$, when present, is independently selected from hydrogen, C1-C4 alkyl, and a protecting group; and wherein each occurrence of $R^{6a}$, $R^{6b}$, $R^{6c}$, and $R^{6d}$ is independently selected from hydrogen and C1-C4 alkyl.

In a further aspect, the nitric oxide linker moiety has a structure represented by a formula:

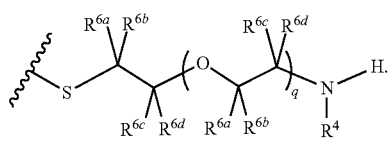

In a further aspect, the nitric oxide linker moiety has a structure represented by a formula:

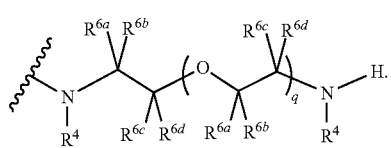

In a further aspect, the nitric oxide linker moiety has a structure represented by a formula:

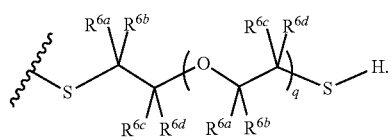

In a further aspect, the nitric oxide linker moiety has a structure represented by a formula:

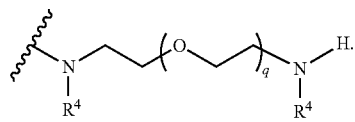

In a further aspect, the nitric oxide linker moiety has a structure represented by a formula:

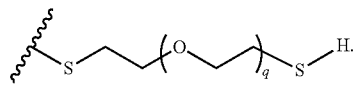

In a further aspect, the nitric oxide linker moiety has a structure represented by a formula:

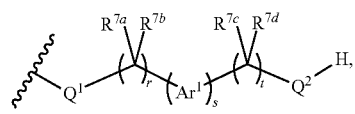

wherein each of r and t is independently selected from 0 and 1; wherein s is selected from 1, 2, and 3; wherein each of $Q^1$ and $Q^2$ is independently selected from S and $NR^4$; wherein each occurrence of $R^4$, when present, is independently selected from hydrogen, C1-C4 alkyl, and a protecting group; wherein each occurrence of $R^{7a}$, $R^{7b}$, $R^{7c}$, and $R^{7d}$ is independently selected from hydrogen and C1-C4 alkyl; and wherein each occurrence of $Ar^1$ is independently selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl.

In a further aspect, the nitric oxide linker moiety has a structure represented by a formula:

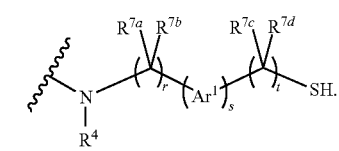

In a further aspect, the nitric oxide linker moiety has a structure represented by a formula:

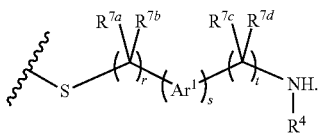

In a further aspect, the nitric oxide linker moiety has a structure represented by a formula:

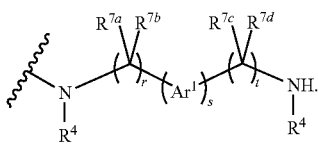

In a further aspect, the nitric oxide linker moiety has a structure represented by a formula:

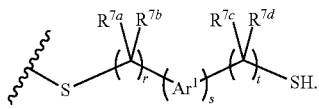

In a further aspect, the nitric oxide linker moiety has a structure represented by a formula:

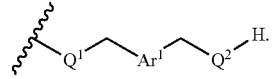

In a further aspect, the nitric oxide linker moiety has a structure represented by a formula:

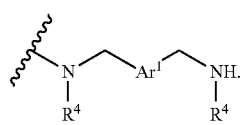

In a further aspect, the nitric oxide linker moiety has a structure represented by a formula:

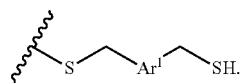

In a further aspect, the nitric oxide linker moiety has a structure represented by a formula:

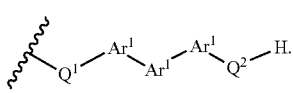

In a further aspect, the nitric oxide linker moiety has a structure represented by a formula:

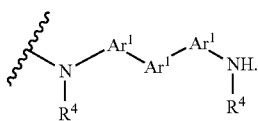

In a further aspect, the nitric oxide linker moiety has a structure represented by a formula:

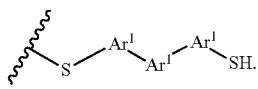

In a further aspect, the nitric oxide linker moiety has a structure selected from:

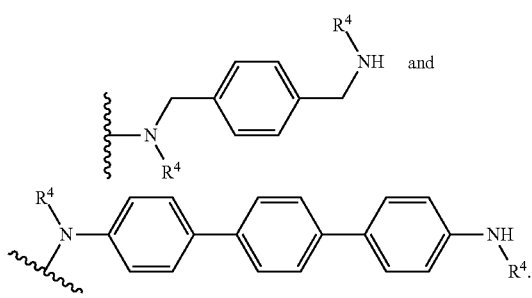

In a further aspect, the nitric oxide linker moiety has a structure selected from:

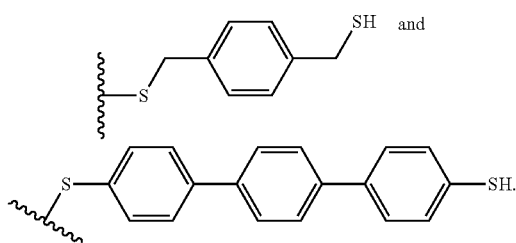

In one aspect, each of m, o, and p is independently selected from 1, 2, 3, and 4. In a further aspect, each of m, o, and p is independently selected from 1, 2, and 3. In a still further aspect, each of m, o, and p is independently selected from 1 and 2. In yet a further aspect, each of m, o, and p is 4. In an even further aspect, each of m, o, and p is 3. In a still further aspect, each of m, o, and p is 2. In yet a further aspect, each of m, o, and p is 1.

In one aspect, q is selected from 1, 2, 3, and 4. In a further aspect, q is selected from 1, 2, and 3. In a still further aspect, q is selected from 1 and 2. In yet a further aspect, q is 4. In an even further aspect, q is 3. In a still further aspect, q is 2. In yet a further aspect, q is 1.

In one aspect, each of r and t is independently selected from 0 and 1. In a still further aspect, each of r and t is 1. In yet a further aspect, each of r and t is 0. In an even further aspect, r is 0 and t is 1. In a still further aspect, r is 1 and t is 0.

In one aspect, s is selected from 1, 2, and 3. In a still further aspect, s is selected from 1 and 2. In yet a further aspect, s is 3. In an even further aspect, s is 2. In a still further aspect, s is 1.

a. $Q^1$ and $Q^2$ Groups

In one aspect, each of $Q^1$ and $Q^2$ is independently selected from S and $NR^4$. In a further aspect, each of $Q^1$ and $Q^2$ is S. In a still further aspect, each of $Q^1$ and $Q^2$ is $NR^4$. In yet a further aspect, $Q^1$ is S and $Q^2$ is $NR^4$. In an even further aspect, $Q^1$ is $NR^4$ and $Q^2$ is S.

b. $R^{2a}$, $R^{2b}$, $R^{2c}$, and $R^{2d}$ Groups

In one aspect, each occurrence of $R^{2a}$, $R^{2b}$, $R^{2c}$, and $R^{2d}$ is independently selected from hydrogen and C1-C4 alkyl. In a further aspect, each occurrence of $R^{2a}$, $R^{2b}$, $R^{2c}$, and $R^{2d}$ is hydrogen.

In a further aspect, each occurrence of $R^{2a}$, $R^{2b}$, $R^{2c}$, and $R^{2d}$ is independently selected from hydrogen, methyl, ethyl, n-propyl, i-propyl, n-butyl, i-butyl, s-butyl, and t-butyl. In a still further aspect, each occurrence of $R^{2a}$, $R^{2b}$, $R^{2c}$, and $R^{2d}$ is independently selected from hydrogen, methyl, ethyl, n-propyl, and i-propyl. In yet a further aspect, each occurrence of $R^{2a}$, $R^{2b}$, $R^{2c}$, and $R^{2d}$ is independently selected from hydrogen, methyl, and ethyl. In an even further aspect, each occurrence of $R^{2a}$, $R^{2b}$, $R^{2c}$, and $R^{2d}$ is independently selected from hydrogen and ethyl. In a still further aspect, each occurrence of $R^{2a}$, $R^{2b}$, $R^{2c}$, and $R^{2d}$ is independently selected from hydrogen and methyl.

c. $R^{3a}$ and $R^{3b}$ Groups

In one aspect, each occurrence of $R^{3a}$ and $R^{3b}$ is independently selected from hydrogen, $-OR^5$, and C1-C4 alkyl. In a further aspect, each occurrence of $R^{3a}$ and $R^{3b}$ is hydrogen.

In a further aspect, each occurrence of $R^{3a}$ and $R^{3b}$ is independently selected from hydrogen, $-OR^5$, methyl, ethyl, n-propyl, i-propyl, n-butyl, i-butyl, s-butyl, and t-butyl. In a still further aspect, each occurrence of $R^{3a}$ and $R^{3b}$ is independently selected from hydrogen, $-OR^5$, methyl, ethyl, n-propyl, and i-propyl. In yet a further aspect, each occurrence of $R^{3a}$ and $R^{3b}$ is independently selected from hydrogen, $-OR^5$, methyl, and ethyl. In an even further aspect, each occurrence of $R^{3a}$ and $R^{3b}$ is independently selected from hydrogen, $-OR^5$, and ethyl. In a still further aspect, each occurrence of $R^{3a}$ and $R^{3b}$ is independently selected from hydrogen, $-OR^5$, and methyl.

In a further aspect, each occurrence of $R^{3a}$ and $R^{3b}$ is independently selected from hydrogen, methyl, ethyl, n-propyl, i-propyl, n-butyl, i-butyl, s-butyl, and t-butyl. In a still further aspect, each occurrence of $R^{3a}$ and $R^{3b}$ is independently selected from hydrogen, methyl, ethyl, n-propyl, and i-propyl. In yet a further aspect, each occurrence of $R^{3a}$ and $R^{3b}$ is independently selected from hydrogen, methyl, and ethyl. In an even further aspect, each occurrence of $R^{3a}$ and $R^{3b}$ is independently selected from hydrogen and ethyl. In a still further aspect, each occurrence of $R^{3a}$ and $R^{3b}$ is independently selected from hydrogen and methyl.

d. $R^4$ Groups

In one aspect, each occurrence of $R^4$, when present, is independently selected from hydrogen, C1-C4 alkyl, and a protecting group. Examples of protecting groups include, but are not limited to, carbobenyloxy, p-methoxybenzyl carbonyl, t-butyloxycarbonyl, 9-fluorenylmethyloxycarbonyl, acetyl, benzoyl, benzyl, a carbamate, p-methoxybenzyl, 3,4-dimethoxybenzyl, p-methoxyphenyl, tosyl, trichloromethyl chloroformate, nosyl, and 2-nitrophenylsulphenyl. Thus, in a further aspect, each occurrence of $R^4$, when present, is independently selected from hydrogen and a protecting group. In a still further aspect, each occurrence of $R^4$, when present, is a protecting group. In yet a further aspect, each occurrence of $R^4$, when present, is hydrogen.

In a further aspect, each occurrence of $R^4$, when present, is independently selected from hydrogen, methyl, ethyl, n-propyl, i-propyl, n-butyl, i-butyl, s-butyl, and t-butyl. In a still further aspect, each occurrence of $R^4$, when present, is independently selected from hydrogen, methyl, ethyl, n-propyl, and i-propyl. In yet a further aspect, each occurrence of $R^4$, when present, is independently selected from hydrogen, methyl, and ethyl. In an even further aspect, each occurrence of $R^4$, when present, is independently selected from hydrogen and ethyl. In a still further aspect, each occurrence of $R^4$, when present, is independently selected from hydrogen and methyl.

e. $R^5$ Groups

In one aspect, $R^5$, when present, is selected from hydrogen, C1-C4 alkyl, and an alcohol protecting group. Examples of alcohol protecting groups include, but are not limited to, acetyl, benzoyl, benzyl, β-methoxyethoxymethyl ether, dimethoxytrityl, methoxymethyl ether, methoxytrityl [(4-methoxyphenyl)diphenylmethyl], p-methyoxybenzyl ether, methylthiomethyl ether, pivaloyl, tetrahydropyranyl, tetrahydrofuran, trityl, trimethylsilyl, t-butyldimethylsilyl, tri-iso-propylsilyloxymethyl, triisopropylsilyl, methyl ether, and ethoxyethyl ether. Thus, in a further aspect, each occurrence of $R^5$, when present, is independently selected from hydrogen and an alcohol protecting group. In a still further aspect, each occurrence of $R^5$, when present, is an alcohol protecting group. In yet a further aspect, each occurrence of $R^5$, when present, is hydrogen.

In a further aspect, each occurrence of $R^5$, when present, is independently selected from hydrogen, methyl, ethyl, n-propyl, i-propyl, n-butyl, i-butyl, s-butyl, and t-butyl. In a still further aspect, each occurrence of $R^5$, when present, is independently selected from hydrogen, methyl, ethyl, n-propyl, and i-propyl. In yet a further aspect, each occurrence of $R^5$, when present, is independently selected from hydrogen, methyl, and ethyl. In an even further aspect, each occurrence of $R^5$, when present, is independently selected from hydrogen and ethyl. In a still further aspect, each occurrence of $R^5$, when present, is independently selected from hydrogen and methyl.

f. $R^{6a}$, $R^{6b}$, $R^{6c}$, and $R^{6d}$ Groups

In one aspect, each occurrence of $R^{6a}$, $R^{6b}$, $R^{6c}$, and $R^{6d}$ is independently selected from hydrogen and C1-C4 alkyl. In a further aspect, each occurrence of $R^{6a}$, $R^{6b}$, $R^{6c}$, and $R^{6d}$ is hydrogen.

In a further aspect, each occurrence of $R^{6a}$, $R^{6b}$, $R^{6c}$, and $R^{6d}$ is independently selected from hydrogen, methyl, ethyl, n-propyl, i-propyl, n-butyl, i-butyl, s-butyl, and t-butyl. In a still further aspect, each occurrence of $R^{6a}$, $R^{6b}$, $R^{6c}$, and $R^{6d}$ is independently selected from hydrogen, methyl, ethyl, n-propyl, and i-propyl. In yet a further aspect, each occurrence of $R^{6a}$, $R^{6b}$, $R^{6c}$, and $R^{6d}$ is independently selected from hydrogen, methyl, and ethyl. In an even further aspect, each occurrence of $R^{6a}$, $R^{6b}$, $R^{6c}$, and $R^{6d}$ is independently selected from hydrogen and ethyl. In a still further aspect, each occurrence of $R^{6a}$, $R^{6b}$, $R^{6c}$, and $R^{6d}$ is independently selected from hydrogen and methyl.

g. $R^{7a}$, $R^{7b}$, $R^{7c}$, and $R^{7d}$ Groups

In one aspect, each occurrence of $R^{7a}$, $R^{7b}$, $R^{7c}$, and $R^{7d}$ is independently selected from hydrogen and C1-C4 alkyl. In a further aspect, each occurrence of $R^{7a}$, $R^{7b}$, $R^{7c}$, and $R^{7d}$ is hydrogen.

In a further aspect, each occurrence of $R^{7a}$, $R^{7b}$, $R^{7c}$, and $R^{7d}$ is independently selected from hydrogen, methyl, ethyl, n-propyl, i-propyl, n-butyl, i-butyl, s-butyl, and t-butyl. In a still further aspect, each occurrence of $R^{7a}$, $R^{7b}$, $R^{7c}$, and $R^{7d}$ is independently selected from hydrogen, methyl, ethyl, n-propyl, and i-propyl. In yet a further aspect, each occurrence of $R^{7a}$, $R^{7b}$, $R^{7c}$, and $R^{7d}$ is independently selected from hydrogen, methyl, and ethyl. In an even further aspect, each occurrence of $R^{7a}$, $R^{7b}$, $R^{7c}$, and $R^{7d}$ is independently selected from hydrogen and ethyl. In a still further aspect, each occurrence of $R^{7a}$, $R^{7b}$, $R^{7c}$, and $R^{7d}$ is independently selected from hydrogen and methyl.

h. $Ar^1$ Groups

In one aspect, each occurrence of $Ar^1$ is independently selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl.

In a further aspect, each occurrence of $Ar^1$ is independently selected from aryl, five-membered heteroaryl, and six-membered heteroaryl and is substituted with 0-3 non-hydrogen groups independently selected from halogen, —OH, —CN, C1-C4 alkyl, C1-C4 alkoxy, and C1-C4 haloalkyl. In a still further aspect, each occurrence of $Ar^1$ is independently selected from aryl, five-membered heteroaryl, and six-membered heteroaryl and is substituted with 0-2 non-hydrogen groups independently selected from halogen, —OH, —CN, C1-C4 alkyl, C1-C4 alkoxy, and C1-C4 haloalkyl. In yet a further aspect, each occurrence of $Ar^1$ is independently selected from aryl, five-membered heteroaryl, and six-membered heteroaryl and is substituted with 0-1 non-hydrogen groups selected from halogen, —OH, —CN, C1-C4 alkyl, C1-C4 alkoxy, and C1-C4 haloalkyl. In an even further aspect, each occurrence of $Ar^1$ is independently selected from aryl, five-membered heteroaryl, and six-membered heteroaryl and is substituted with a non-hydrogen group selected from halogen, —OH, —CN, C1-C4 alkyl, C1-C4 alkoxy, and C1-C4 haloalkyl. In a still further aspect, each occurrence of $Ar^1$ is independently selected from aryl, five-membered heteroaryl, and six-membered heteroaryl and is unsubstituted.

In a further aspect, each occurrence of $Ar^1$ is aryl substituted with 0-4 non-hydrogen groups independently selected from halogen, —OH, —CN, C1-C4 alkyl, C1-C4 alkoxy, and C1-C4 haloalkyl. In a still further aspect, each occurrence of $Ar^1$ is aryl substituted with 0-3 non-hydrogen groups independently selected from halogen, —OH, —CN, C1-C4 alkyl, C1-C4 alkoxy, and C1-C4 haloalkyl. In yet a further aspect, each occurrence of $Ar^1$ is aryl substituted with 0-2 non-hydrogen groups independently selected from halogen, —OH, —CN, C1-C4 alkyl, C1-C4 alkoxy, and C1-C4 haloalkyl. In an even further aspect, each occurrence of $Ar^1$ is aryl substituted with 0-1 non-hydrogen groups selected from halogen, —OH, —CN, C1-C4 alkyl, C1-C4 alkoxy, and C1-C4 haloalkyl. In a still further aspect, each occurrence of $Ar^1$ is aryl substituted with a non-hydrogen group selected from halogen, —OH, —CN, C1-C4 alkyl, C1-C4 alkoxy, and C1-C4 haloalkyl. In yet a further aspect, each occurrence of $Ar^1$ is unsubstituted aryl.

In a further aspect, each occurrence of $Ar^1$ is phenyl substituted with 0-4 non-hydrogen groups independently selected from halogen, —OH, —CN, C1-C4 alkyl, C1-C4 alkoxy, and C1-C4 haloalkyl. In a still further aspect, each occurrence of $Ar^1$ is phenyl substituted with 0-3 non-hydrogen groups independently selected from halogen, —OH, —CN, C1-C4 alkyl, C1-C4 alkoxy, and C1-C4 haloalkyl. In yet a further aspect, each occurrence of $Ar^1$ is phenyl substituted with 0-2 non-hydrogen groups independently selected from halogen, —OH, —CN, C1-C4 alkyl, C1-C4 alkoxy, and C1-C4 haloalkyl. In an even further aspect, each occurrence of $Ar^1$ is phenyl substituted with 0-1 non-hydrogen groups selected from halogen, —OH, —CN, C1-C4 alkyl, C1-C4 alkoxy, and C1-C4 haloalkyl. In a still further aspect, each occurrence of $Ar^1$ is phenyl substituted with a non-hydrogen group selected from halogen, —OH, —CN, C1-C4 alkyl, C1-C4 alkoxy, and C1-C4 haloalkyl. In yet a further aspect, each occurrence of $Ar^1$ is unsubstituted phenyl.

In a further aspect, each occurrence of $Ar^1$ is independently selected from five-membered heteroaryl and six-membered heteroaryl and is substituted with 0-4 non-hydrogen groups independently selected from halogen, —OH, —CN, C1-C4 alkyl, C1-C4 alkoxy, and C1-C4 haloalkyl. In a still further aspect, each occurrence of $Ar^1$ is independently selected from five-membered heteroaryl and six-membered heteroaryl and is substituted with 0-3 non-hydrogen groups independently selected from halogen, —OH, —CN, C1-C4 alkyl, C1-C4 alkoxy, and C1-C4 haloalkyl. In yet a further aspect, each occurrence of $Ar^1$ is independently selected from five-membered heteroaryl and six-membered heteroaryl and is substituted with 0-2 non-hydrogen groups independently selected from halogen, —OH, —CN, C1-C4 alkyl, C1-C4 alkoxy, and C1-C4 haloalkyl. In an even further aspect, each occurrence of $Ar^1$ is independently selected from five-membered heteroaryl and six-membered heteroaryl and is substituted with 0-1 non-hydrogen groups selected from halogen, —OH, —CN, C1-C4 alkyl, C1-C4 alkoxy, and C1-C4 haloalkyl. In a still further aspect, each occurrence of $Ar^1$ is independently selected from five-membered heteroaryl and six-membered heteroaryl and is substituted with a non-hydrogen group selected from halogen, —OH, —CN, C1-C4 alkyl, C1-C4 alkoxy, and C1-C4 haloalkyl. In yet a further aspect, each occurrence of $Ar^1$ is independently selected from five-membered heteroaryl and six-membered heteroaryl and is unsubstituted.

In a further aspect, each occurrence of $Ar^1$ is five-membered heteroaryl substituted with 0-4 non-hydrogen groups independently selected from halogen, —OH, —CN, C1-C4 alkyl, C1-C4 alkoxy, and C1-C4 haloalkyl. In a still further aspect, each occurrence of $Ar^1$ is five-membered heteroaryl substituted with 0-3 non-hydrogen groups independently selected from halogen, —OH, —CN, C1-C4 alkyl, C1-C4 alkoxy, and C1-C4 haloalkyl. In yet a further aspect, each occurrence of $Ar^1$ is five-membered heteroaryl substituted with 0-2 non-hydrogen groups independently selected from halogen, —OH, —CN, C1-C4 alkyl, C1-C4 alkoxy, and C1-C4 haloalkyl. In an even further aspect, each occurrence of $Ar^1$ is five-membered heteroaryl substituted with 0-1 non-hydrogen groups selected from halogen, —OH, —CN, C1-C4 alkyl, C1-C4 alkoxy, and C1-C4 haloalkyl. In a still further aspect, each occurrence of $Ar^1$ is five-membered heteroaryl substituted with a non-hydrogen group selected from halogen, —OH, —CN, C1-C4 alkyl, C1-C4 alkoxy, and C1-C4 haloalkyl. In yet a further aspect, each occurrence of $Ar^1$ is unsubstituted five-membered heteroaryl.

In a further aspect, each occurrence of $Ar^1$ is six-membered heteroaryl substituted with 0-4 non-hydrogen groups independently selected from halogen, —OH, —CN, C1-C4 alkyl, C1-C4 alkoxy, and C1-C4 haloalkyl. In a still further aspect, each occurrence of $Ar^1$ is six-membered heteroaryl substituted with 0-3 non-hydrogen groups independently selected from halogen, —OH, —CN, C1-C4 alkyl, C1-C4 alkoxy, and C1-C4 haloalkyl. In yet a further aspect, each occurrence of $Ar^1$ is six-membered heteroaryl substituted with 0-2 non-hydrogen groups independently selected from halogen, —OH, —CN, C1-C4 alkyl, C1-C4 alkoxy, and C1-C4 haloalkyl. In an even further aspect, each occurrence of $Ar^1$ is six-membered heteroaryl substituted with 0-1 non-hydrogen groups selected from halogen, —OH, —CN, C1-C4 alkyl, C1-C4 alkoxy, and C1-C4 haloalkyl. In a still further aspect, each occurrence of $Ar^1$ is six-membered heteroaryl substituted with a non-hydrogen group selected from halogen, —OH, —CN, C1-C4 alkyl, C1-C4 alkoxy, and C1-C4 haloalkyl. In yet a further aspect, each occurrence of $Ar^1$ is unsubstituted six-membered heteroaryl.

3. Nitric Oxide Molecules

In one aspect, disclosed are degradable polymers comprising at least one nitric oxide molecule covalently bonded to the nitric oxide linker moiety.

In a further aspect, the nitric oxide linker moiety and nitric oxide together comprise a group selected from a diazeniumdiolate, a nitrosothiol, a nitrosamine, a hydroxyl nitrosamine, a hydroxyl amine, and a hydroxyurea. In a still further aspect, the nitric oxide linker moiety and nitric oxide together comprise a nitrosothiol.

In a further aspect, the nitric oxide linker moiety and nitric oxide together has a structure represented by a formula selected from:

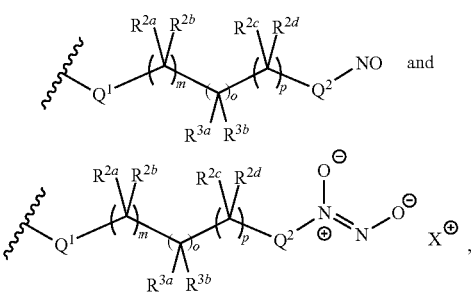

wherein each of m, o, and p is independently selected from 1, 2, 3, and 4; wherein each of $Q^1$ and $Q^2$ is independently selected from S and $NR^4$; wherein each occurrence of $R^4$, when present, is independently selected from hydrogen, C1-C4 alkyl, and a protecting group; and wherein each occurrence of $R^{2a}$, $R^{2b}$, $R^{2c}$, and $R^{2d}$ is independently selected from hydrogen and C1-C4 alkyl; wherein each occurrence of $R^{3a}$ and $R^{3b}$ is independently selected from hydrogen, $—OR^5$, and C1-C4 alkyl; wherein $R^5$, when present, is selected from hydrogen, C1-C4 alkyl, and an alcohol protecting group; and wherein X is an organic soluble cation. Thus, without wishing to be bound by theory X can be, for example, a tetra alkyl ammonium cation.

In a further aspect, the nitric oxide linker moiety and nitric oxide together has a structure represented by a formula:

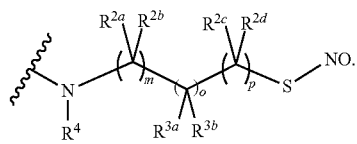

In a further aspect, the nitric oxide linker moiety and nitric oxide together has a structure represented by a formula:

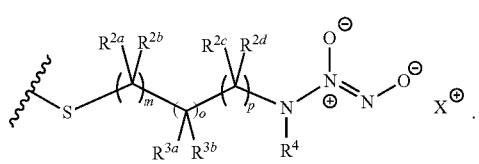

In a further aspect, the nitric oxide linker moiety and nitric oxide together has a structure represented by a formula:

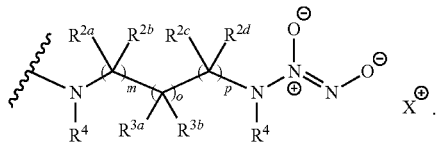

In a further aspect, the nitric oxide linker moiety and nitric oxide together has a structure represented by a formula:

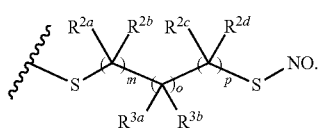

In a further aspect, the nitric oxide linker moiety and nitric oxide together has a structure selected from:

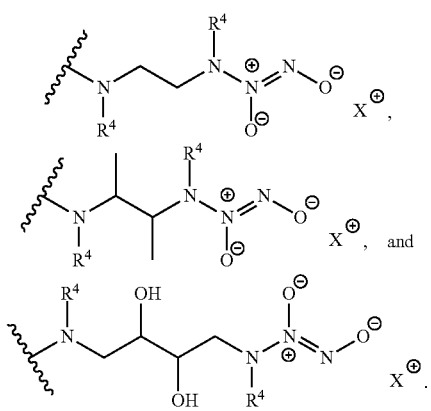

In a further aspect, the nitric oxide linker moiety and nitric oxide together has a structure selected from:

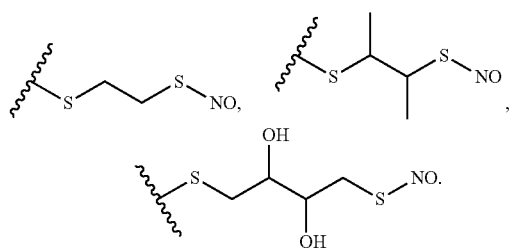

In a further aspect, the nitric oxide linker moiety and nitric oxide together has a structure represented by a formula selected from:

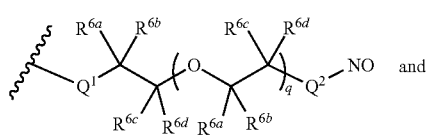

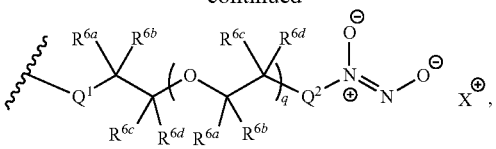

wherein q is selected from 1, 2, 3, and 4; wherein each of $Q^1$ and $Q^2$ is independently selected from S and $NR^4$; wherein each occurrence of $R^4$, when present, is independently selected from hydrogen, C1-C4 alkyl, and a protecting group; and wherein each occurrence of $R^{6a}$, $R^{6b}$, $R^{6c}$, and $R^{6d}$ is independently selected from hydrogen and C1-C4 alkyl.

In a further aspect, the nitric oxide linker moiety and nitric oxide together has a structure represented by a formula:

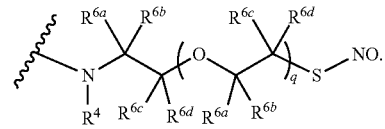

In a further aspect, the nitric oxide linker moiety and nitric oxide together has a structure represented by a formula:

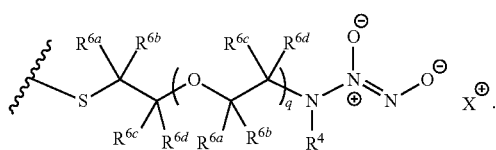

In a further aspect, the nitric oxide linker moiety and nitric oxide together has a structure represented by a formula:

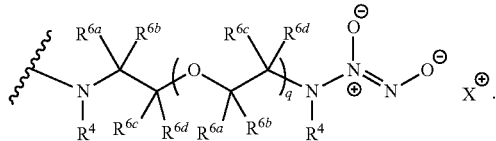

In a further aspect, the nitric oxide linker moiety and nitric oxide together has a structure represented by a formula:

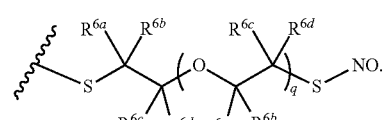

In a further aspect, the nitric oxide linker moiety and nitric oxide together has a structure represented by a formula:

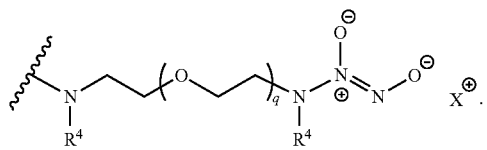

In a further aspect, the nitric oxide linker moiety and nitric oxide together has a structure represented by a formula:

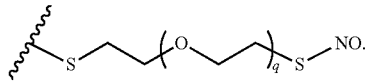

In a further aspect, the nitric oxide linker moiety and nitric oxide together has a structure represented by a formula selected from:

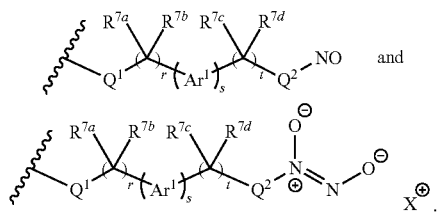

wherein each of r and t is independently selected from 0 and 1; wherein s is selected from 1, 2, and 3; wherein each of $Q^1$ and $Q^2$ is independently selected from S and $NR^4$; wherein each occurrence of $R^4$, when present, is independently selected from hydrogen, C1-C4 alkyl, and a protecting group; wherein each occurrence of $R^{7a}$, $R^{7b}$, $R^{7c}$, and $R^{7d}$ is independently selected from hydrogen and C1-C4 alkyl; and wherein each occurrence of $Ar^1$ is independently selected from aryl, five-membered heteroaryl, and six-membered heteroaryl and is substituted with 0-4 non-hydrogen groups independently selected from halogen, —OH, —CN, C1-C4 alkyl, C1-C4 alkoxy, and C1-C4 haloalkyl.

In a further aspect, the nitric oxide linker moiety and nitric oxide together has a structure represented by a formula:

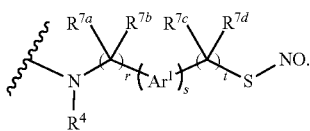

In a further aspect, the nitric oxide linker moiety and nitric oxide together has a structure represented by a formula:

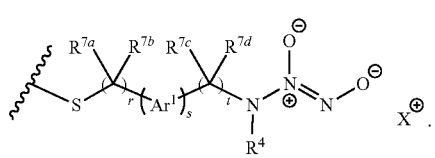

In a further aspect, the nitric oxide linker moiety and nitric oxide together has a structure represented by a formula:

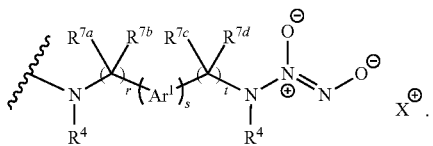

In a further aspect, the nitric oxide linker moiety and nitric oxide together has a structure represented by a formula:

In a further aspect, the nitric oxide linker moiety and nitric oxide together has a structure represented by a formula selected from:

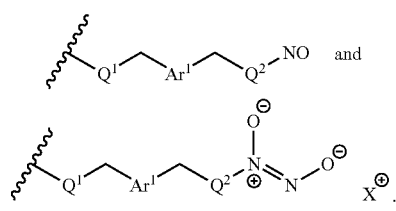

In a further aspect, the nitric oxide linker moiety and nitric oxide together has a structure represented by a formula:

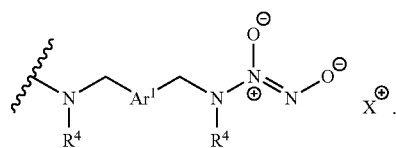

In a further aspect, the nitric oxide linker moiety and nitric oxide together has a structure represented by a formula:

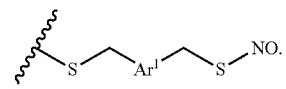

In a further aspect, the nitric oxide linker moiety and nitric oxide together has a structure represented by a formula selected from:

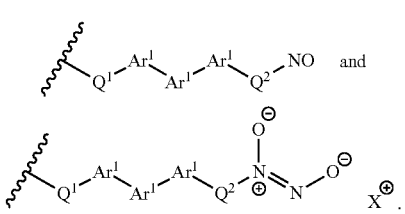

In a further aspect, the nitric oxide linker moiety and nitric oxide together has a structure represented by a formula:

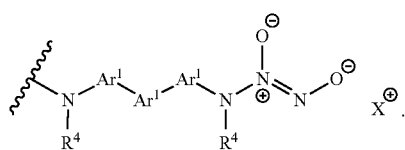

In a further aspect, the nitric oxide linker moiety and nitric oxide together has a structure represented by a formula:

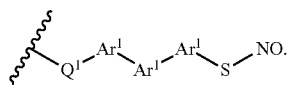

In a further aspect, the nitric oxide linker moiety and nitric oxide together has a structure selected from:

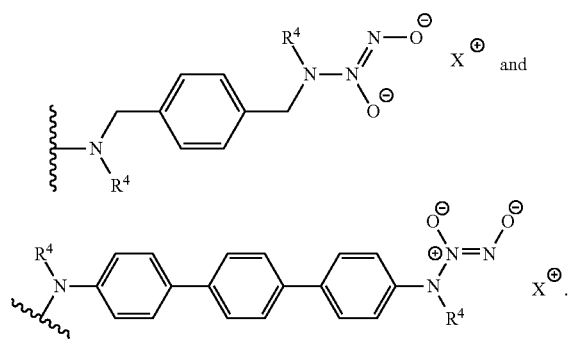

In a further aspect, the nitric oxide linker moiety and nitric oxide together has a structure selected from:

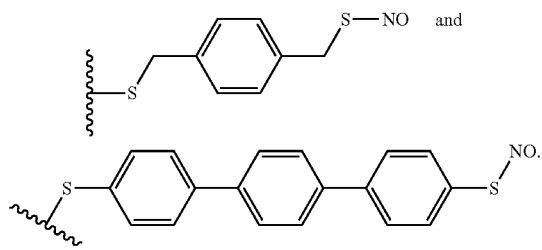

C. Pharmaceutical Compositions

In one aspect, disclosed are pharmaceutical composition comprising a therapeutically effective amount of at least one degradable polymer comprising: (a) a biodegradable polymer backbone; (b) at least one nitric oxide linker moiety pendant from the polymer backbone; and (c) at least one nitric oxide molecule covalently bonded to the nitric oxide linker moiety, or a pharmaceutically acceptable salt thereof, and a pharmaceutically acceptable carrier.

In various aspects, the compounds and compositions of the invention can be administered in pharmaceutical compositions, which are formulated according to the intended method of administration. The compounds and compositions described herein can be formulated in a conventional manner using one or more physiologically acceptable carriers or excipients.

The compounds and compositions featured in the invention can be administered by any standard route of administration. For example, administration can be parenteral, intravenous, subcutaneous, or oral.

In various aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In various aspects, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. In various aspects, the instant compositions are soluble in organic solvents, facilitating application as a dopant for polymer films. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In a further aspect, an effective amount is a therapeutically effective amount. In a still further aspect, an effective amount is a prophylactically effective amount.

In a further aspect, the pharmaceutical composition is administered to a mammal. In a still further aspect, the mammal is a human. In an even further aspect, the human is a patient.

In a further aspect, the pharmaceutical composition is used to deliver nitric oxide to a target. In a still further aspect, the target is a subject. In yet a further aspect, the target is a mammal. In an even further aspect, the mammal is a human.

In a further aspect, the pharmaceutical composition is administered to a subject. In a still further aspect, the subject has been diagnosed with having abnormal cell proliferation, transplantation rejection, thrombosis, restenosis, ischemic injury, a hypertrophic lesion, a keloid, platelet aggregation, or platelet adhesion prior to the administering step. In yet a further aspect, the subject has been diagnosed with a need of wound healing prior to the administering step. In an even further aspect, the subject has had or currently has an intravenous device and/or a glucose biosensor.

In a further aspect, the pharmaceutical composition is used to treat a disorder selected from cancer, a cardiovascular disease, a bacterial infection, a circulatory dysfunction, a gastrointestinal disorder, or a sexually transmitted disease.

It is understood that the disclosed compositions can be prepared from the disclosed compounds. It is also understood that the disclosed compositions can be employed in the disclosed methods of using.

D. Methods of Making a Degradable Polymer

In one aspect, disclosed are methods of making a degradable polymer, the method comprising the step of functionalizing a polymer scaffold with a nitric oxide donor, wherein the polymer scaffold comprises: (a) a biodegradable polymer backbone; and (b) at least one nitric oxide linker moiety pendant from the polymer backbone, thereby making the degradable polymer.

In one aspect, disclosed are methods of making a polymer, the method comprising: (a) reacting a polymer comprising at least one hydroxyl group and acryloyl halide to form a vinyl-functionalized polymer; and (b) reacting the vinyl-functionalized polymer with a dinucleophile to form a polymer scaffold, thereby making the polymer. In one aspect, disclosed are methods of making a polymer, the method comprising: (a) reacting a polymer comprising at least one hydroxyl group and acryloyl halide to form a vinyl-functionalized polymer; and (b) reacting the vinyl-functionalized polymer with a nucleophile to form a polymer scaffold, thereby making the polymer.

In a further aspect, the polymer backbone is a polyester backbone.

In a further aspect, the polymer is hyperbranched.

In a further aspect, the polymer is a polyester. In a still further aspect, the polymer is a bis-MPA polyester.

In a further aspect, the polymer comprises at least one polyester residue.

In a further aspect, the nucleophile is an amine. In a still further aspect, the nucleophile is a dinucleophile.

In a further aspect, the dinucleophile is a dithiol. In a still further aspect, the dinucleophile is a diamine. In yet a further aspect, the dinucleophile comprises a thiol and an amine.

In a further aspect, the dinucleophile is selected from:

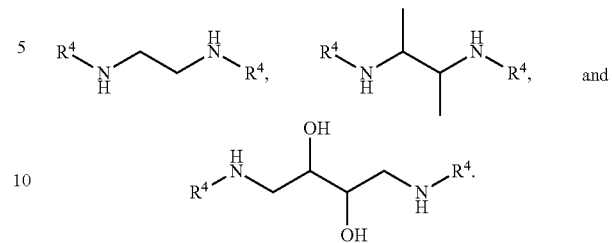

In a further aspect, the dinucleophile is selected from:

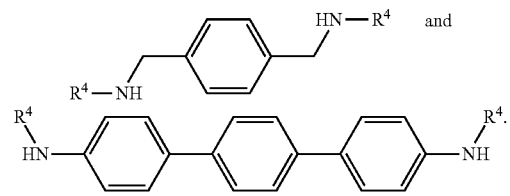

In a further aspect, the dinucleophile has a structure represented by a formula:

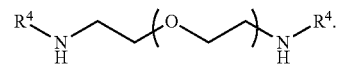

In a further aspect, the dinucleophile is selected from:

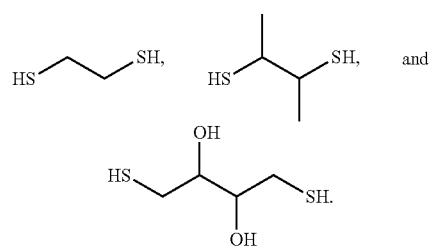

In a further aspect, the dinucleophile is selected from:

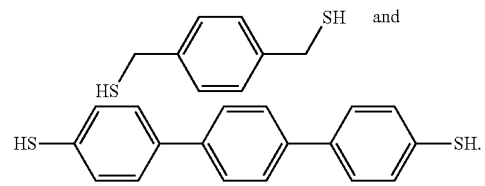

In a further aspect, the dinucleophile has a structure represented by a formula:

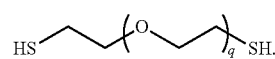

In a further aspect, the polyester scaffold comprises at least one residue selected from:

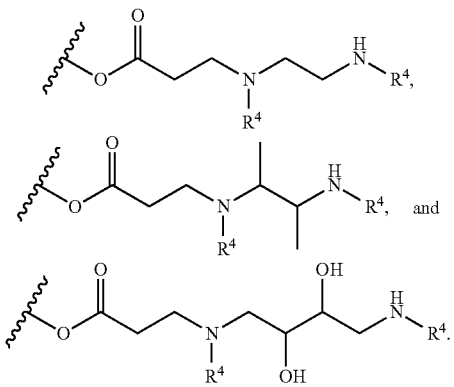

In a further aspect, the polyester scaffold comprises at least one residue selected from:

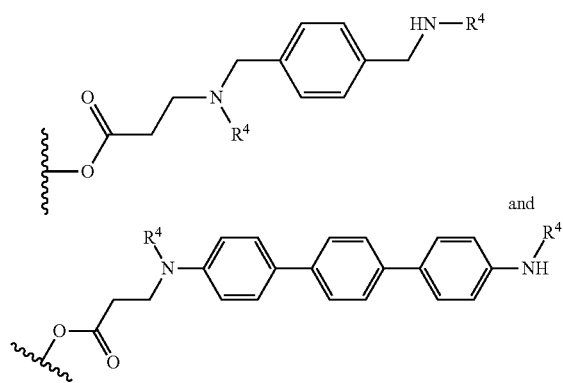

In a further aspect, the polyester scaffold comprises at least one residue having a structure represented by a formula:

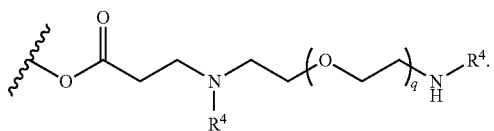

In a further aspect, the polyester scaffold comprises at least one residue selected from:

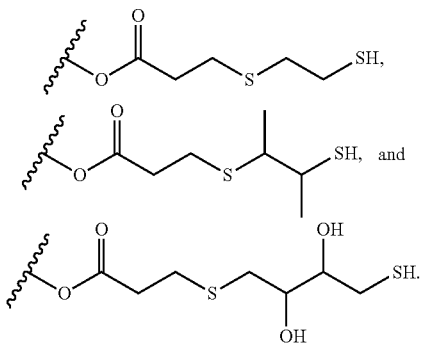

In a further aspect, the polyester scaffold comprises at least one residue selected from:

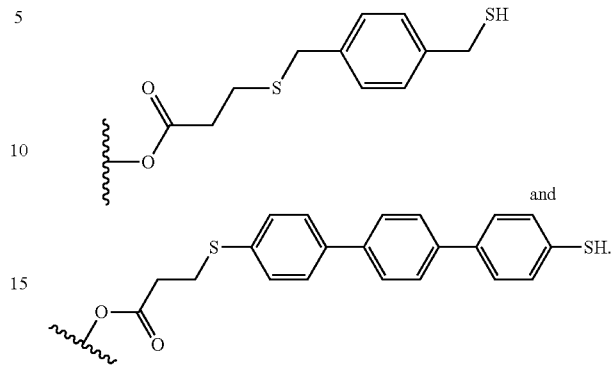

In a further aspect, the polyester scaffold comprises at least one residue having a structure represented by a formula:

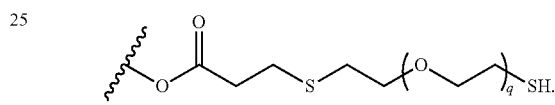

In a further aspect, the method further comprises the step of reacting a compound comprising at least one hydroxyl group with a repeating unit comprising at least one carboxylate group and at least one hydroxyl group, thereby making the polymer comprising at least one hydroxyl group.

In a further aspect, the compound comprising at least one hydroxyl group is selected from trimethylolpropane, di-trimethylolpropane, 2,2-bis(hydroxymethyl)propane-1,3-diol, glycerol, 1,3,5-tris(2-hydroxyethyl)cyanuric acid, and ethoxylated tetra(hydroxymethyl)methane.

In a further aspect, the repeating unit has a structure represented by a formula:

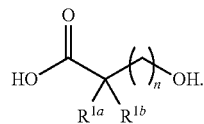

wherein each occurrence of n is independently selected from 0, 1, 2, 3, or 4; wherein $R^{1a}$ is selected from —OH, C1-C4 alkyl, and C1-C4 hydroxyalkyl; and wherein $R^{1b}$ is selected from C1-C4 alkyl and C1-C4 hydroxyalkyl.

In a further aspect, the repeating unit has a structure:

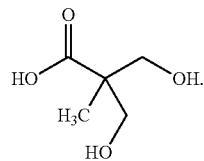

In a further aspect, the molar ratio of the compound comprising at least one hydroxyl group to the repeating unit is of from about 1:9 to about 1:45. In a still further aspect, the molar ratio of the compound comprising at least one hydroxyl group to the repeating unit is of from about 1:9 to about 1:5. In yet a further aspect, the molar ratio of the compound comprising at least one hydroxyl group to the repeating unit is of from about 1:9 to about 1:6. In an even further aspect, the molar ratio of the compound comprising at least one hydroxyl group to the repeating unit is of from about 1:9 to about 1:7. In a still further aspect, the molar ratio of the compound comprising at least one hydroxyl group to the repeating unit is of from about 1:9 to about 1:8. In yet a further aspect, the molar ratio of the compound comprising at least one hydroxyl group to the repeating unit is of from about 1:8 to about 1:45. In an even further aspect, the molar ratio of the compound comprising at least one hydroxyl group to the repeating unit is of from about 1:7 to about 1:45. In a still further aspect, the molar ratio of the compound comprising at least one hydroxyl group to the repeating unit is of from about 1:6 to about 1:45.

In a further aspect, the method further comprises the step of functionalizing a polymer scaffold with a nitric oxide donor, thereby making a degradable polymer. In a still further aspect, reacting is via nitrosation. In yet a further aspect, reacting is via exposure to nitric oxide gas under basic conditions.

E. Methods of Delivering Nitric Oxide to a Target

In one aspect, disclosed are methods of delivering nitric oxide to a target, the method comprising: (a) administering to the target an effective amount of a degradable polymer comprising: (i) a biodegradable polymer backbone; (ii) at least one nitric oxide linker moiety pendant from the polymer backbone; and (iii) at least one nitric oxide molecule covalently bonded to the nitric oxide linker moiety; and (b) exposing the degradable polymer to at least one of heat, light, copper, a free thiol, and/or a proton source, thereby delivering nitric oxide to the target.

In a further aspect, the target is a subject. In a still further aspect, the subject is a mammal. In yet a further aspect, the mammal is a human.

In a further aspect, the subject has been diagnosed with having abnormal cell proliferation, transplantation rejection, thrombosis, restenosis, ischemic injury, a hypertrophic lesion, a keloid, platelet aggregation, or platelet adhesion prior to the administering step. In a still further aspect, the subject has been diagnosed with a need of wound healing prior to the administering step. In yet a further aspect, the subject has had or currently has an intravenous device and/or a glucose biosensor.

In a further aspect, the effective amount is a therapeutically effective amount. In a still further aspect, the effective amount is a prophylactically effective amount.

In a further aspect, the degradable polymer is exposed to at least one of heat, light, copper, and/or a free thiol. In a still further aspect, the degradable polymer is exposed to a proton source.

F. Methods for the Treatment of a Disorder

In one aspect, disclosed are methods for the treatment of a disorder in a subject, the method comprising the step of administering to the subject an effective amount of a degradable polymer comprising: (a) a biodegradable polymer backbone; (b) at least one nitric oxide linker moiety pendant from the polymer backbone; and (c) at least one nitric oxide molecule covalently bonded to the nitric oxide linker moiety.

In a further aspect, the disorder is selected from cancer, a cardiovascular disease, a bacterial infection, a circulatory dysfunction, a gastrointestinal disorder, or a sexually transmitted disease.

In a further aspect, the subject has been diagnosed with a need for treatment of the disorder prior to the administering step.

In a further aspect, the method further comprises the step of identifying a subject in need of treatment of the disorder.

G. Articles

In one aspect, the invention relates to articles comprising the disclosed compositions. In a further aspect, the present invention contemplates the use of the disclosed compositions in the manufacture of certain items such as articles.

1. Medical Devices

In one aspect, disclosed are medical devices comprising a nitric oxide-releasing polymeric film, wherein the polymer film comprises an effective amount of at least one polymer comprising: (a) a polymer backbone; (b) at least one nitric oxide linker moiety pendant from the polymer backbone; and (c) at least one nitric oxide molecule covalently bonded to the nitric oxide linker moiety.

In a further aspect, the medical device comprises at least one surface coated with the polymeric film.

In a further aspect, the polymer is a degradable polymer. In a still further aspect, the polymer backbone is a biodegradable polymer backbone.

In a further aspect, the polymer is hyperbranched.

In a further aspect, the medical device is selected from an arterial stent, a guide wire, a catheter, a trocar needle, a bone anchor, a bone screw, a protective plating, a hip or joint replacement, an electrical lead, a biosensor, a probe, a surgical drape, a wound dressing, and a bandage. In a still further aspect, the medical device is a biosensor. In yet a further aspect, the biosensor is a glucose biosensor.

H. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. General Experimental

Diethylene triamine pentaacetic acid (DTPA), 5,5'-dithio-bis(2-nitrobenzoic acid) (DTNB), sodium acetate, 2,2-bis (hydroxymethyl)propionic acid (bis-MPA), 2-ethyl-2-(hydroxymethyl)-1,3-propanediol (TMP), 1,2-ethanedithiol (ET), 2,3-butanedithiol (BT), dithiothreitol (DTT), and p-toluenesulfonic acid (p-TSA) were purchased from the Aldrich Chemical Company (Milwaukee, Wis.). Water was purified using a Millipore Milli-Q UV Gradient A10 System (Bethlehem, Pa.) to a final resistivity of 18.2 MΩ·cm and total organic content of ≤6 ppb. Common laboratory salts and solvents were purchased from Fisher Scientific (Pittsburgh, Pa.). Unless noted otherwise, all materials were used as received without further purification.

Proton nuclear magnetic resonance ($^1$H NMR) spectra were recorded on a 400 MHz Bruker instrument. Quantitative carbon nuclear magnetic resonance ($^{13}$C NMR) was performed on a 600 MHz Bruker instrument following a previously reported method (E. Malmstrom, M. Johansson and A. Hult, *Macromolecules*, 1995, 28, 1698-1703). Gel permeation chromatography (GPC) measurements were carried out in tetrahydrofuran (THF) against polystyrene standards using a Waters 2695 system. Elemental analysis was performed on an inductively coupled plasma (ICP) optical emission spectrometer (Prodigy High Dispersion ICP-OES, Teledyne Leeman Labs). The standard addition of a copper reference standard (TraceCERT®, Sigma-Aldrich) and emission intensity at 324.75 nm were utilized to determine the concentration of free copper ion in PBS buffer. Hydrodynamic size and polydispersity index (PDI) were measured by dynamic light scattering (DLS) using a Malvern Zeta Nano-ZS (Westborough, Mass.).

2. Chemistry Experimental a. Synthesis of Hyperbranched Polyesters

Hyperbranched polyesters were prepared according to Malmstrom et al. (E. Malmstrom, M. Johansson and A. Hult, *Macromolecules*, 1995, 28, 1698-1703). Briefly, bis-MPA (5 mmol), TMP (0.555 mmol), and p-TSA (0.02 mmol) were mixed in a three-neck round bottom flask and stirred for 4 h at 140° C. to prepare second generation hyperbranched polyesters (G2-HP). For the synthesis of third generation hyperbranched polyesters (G3-HP), 6.67 mmol bis-MPA and 0.027 mmol p-TSA were subsequently added to this reaction mixture and stirred for an additional 4 h at 140° C. Synthesis of the fourth generation hyperbranched polyesters (G4-HP) was achieved by adding 13.30 mmol bis-MPA and 0.054 mmol p-TSA to the G3-HP reaction mixture after the prior reaction went to completion, followed by stirring for 4 h at 140° C. Nitrogen was continuously flowed through the reaction flask to remove water. After reaction completion, acetone was added to the mixture to dissolve the polyesters, and insoluble reactants were removed via filtration. The crude polyesters were then precipitated from acetone by the addition of hexane. This solid was dried under vacuum overnight at room temperature and stored in acetone after resuspension. The $^1$H NMR data of the hyperbranched polyesters for each generation consisted of the following peaks (400 MHz, acetone-d6, δ): 1.1-1.4 (CH$_3$C), 3.68 (CH$_2$OH), and 4.10-4.3 (CH$_2$OCO).

b. Synthesis of acrylate-Modified Hyperbranched Polyesters

Hyperbranched polyesters (500 mg of G2, G3, or G4) and triethylamine (TEA; 692 µL) were dissolved in 5 mL acetone, followed by the dropwise addition of an acryloyl chloride (AC) solution (0.4 mL AC in 0.6 mL acetone) over a 5-min period. The reaction mixture was stirred for 1 h at room temperature. Precipitate byproducts were removed via filtration. The residual solvent, acryloyl chloride, and TEA in the filtrate were then removed under vacuum at room temperature. $^1$H NMR data of acrylate-modified hyperbranched polyesters consisted of the following peaks (400 MHz, CD$_2$Cl$_2$, δ): 1.1-1.4 (CH$_3$C), 3.68 (CH$_2$OH), 4.1-4.3 (CH$_2$OCO), 5.84 and 6.27 (CH$_2$=CH), 6.07 (CH$_2$=CH).

c. Synthesis of 1,2-ethylenedithiol-, 2,3-butanedithiol-, and dithiothreitol-Modified Hyperbranched Polyesters The acrylate-modified G2-hyperbranched polyesters (200 mg) were dissolved in 2 mL acetone, followed by the addition of TEA (40 µL) and either 1,2-ethylenedithiol (ET; 815 µL) or 2,3-butanedithiol (BT; 1316 µL). Excess ET or BT (20:1 molar ratio compared to acrylate double bonds) was used to minimize crosslinking of the thiol groups. After stirring at room temperature for 18 h, the product was precipitated in hexane and washed with methanol to remove residual ET or BT. The resulting ET or BT thiol-modified hyperbranched polyesters (G2-HP-ET and G2-HP-BT) were collected by centrifugation and dried under vacuum at room temperature for 2 h. $^1$H NMR data of G2-HP-ET consisted of the following peaks (400 MHz, CD$_2$Cl$_2$, δ): 1.1-1.4 (CH$_3$C), 2.6-2.9 (SCH$_2$CH$_2$SH), (SCH$_2$CH$_2$SH), (COCH$_2$CH$_2$SCH$_2$), and (COCH$_2$CH$_2$SCH$_2$), 3.65 (CH$_2$OH), and 4.10-4.3 (CH$_2$OCO). $^1$H NMR data of G2-HP-BT consisted of the following peaks (400 MHz, CD$_2$Cl$_2$, δ): 1.1-1.4 (CH$_3$C), (SCHCH$_3$) and (CH$_3$CHSH), 2.6 (COCH$_2$CH$_2$SCHCH$_3$), 2.85 (COCH$_2$CH$_2$SCHCH$_3$), 2.95 (SCHCH$_3$CHCH$_3$SH), 3.2 (SCHCH$_3$CHCH$_3$SH), 3.65 (CH$_2$OH), and 4.1-4.3 (CH$_2$OCO).

Dithiothreitol-modified hyperbranched polyesters (G2-HP-DTT, G3-HP-DTT, and G4-HP-DTT) were synthesized using a similar procedure. Dithiothreitol (DTT) (1648 mg) and TEA (40 µL) were mixed with either G2, G3, or G4 hyperbranched polyesters (200 mg) in 2 mL acetone. The resulting thiol-modified polyesters were precipitated in water and collected via centrifugation. The residual solvent was removed under vacuum at room temperature. $^1$H NMR data of the DTT-modified hyperbranched polyesters consisted of the following peaks. G2-HP-DTT (400 MHz, CD$_2$Cl$_2$, δ): 1.1-1.4 (CH$_3$C), 2.6-2.9 (COCH$_2$CH$_2$S), (COCH$_2$CH$_2$S), (SCH$_2$CH(OH)), and (CH(OH)CH$_2$SH), 3.65 (CH$_2$OH), 3.70 (SCH$_2$CH(OH)CH(OH)) and (CHCH(OH)CH$_2$SH), 4.10-4.3 (CH$_2$OCO). G3-HP-DTT (400 MHz, CD$_2$Cl$_2$, δ): 1.1-1.4 (CH$_3$C), 2.6-2.9 (COCH$_2$CH$_2$S), (COCH$_2$CH$_2$S), (SCH$_2$CH(OH)), and (CH(OH)CH$_2$SH), 3.65 (CH$_2$OH), 3.70 (SCH$_2$CH(OH)CH(OH)) and (CHCH(OH)CH$_2$SH), 4.10-4.3 (CH$_2$OCO). G4-HP-DTT (400 MHz, CD$_2$Cl$_2$, δ): 1.1-1.4 (CH$_3$C), 2.6-2.9 (COCH$_2$CH$_2$S), (COCH$_2$CH$_2$S), (SCH$_2$CH(OH)), and (CH(OH)CH$_2$SH), 3.65 (CH$_2$OH), 3.70 (SCH$_2$CH(OH)CH(OH)) and (CHCH(OH)CH$_2$SH), 4.1-4.3 (CH$_2$OCO).

d. Nitrosation of thiol-Modified Hyperbranched Polyesters

The thiol-modified hyperbranched polyesters (10 mg) were dissolved in acetone (1 mL) and 5 M hydrochloric acid (100 µL). An aqueous solution (100 µL) containing sodium nitrite (6.9 mg) and diethylenetriamine pentaacetic acid (DTPA; 500 µM) was then added dropwise to this solution over a 1-min period. After stirring for 1 h at 0° C. (i.e., ice bath) in the dark, the solvent was removed under vacuum. Acetone was used to dissolve the resulting nitrosated polyesters (e.g., G2-HP-ET/NO). The solution was filtered to remove residual salt and then stored at −20° C. in the dark until use.

3. Ellman's Assay for Thiol Quantification of Thiol-Modified Hyperbranched Polyesters The free thiol content was quantified using a modified Ellman's assay (G. Gabor and A. Vincze, *Anal. Chim. Acta*, 1977, 92, 429-431; Y. Lu, A. Shah, R. A. Hunter, R. J. Soto and M. H. Schoenfisch, *Acta Biomater.*, 2015, 12, 62-69). A solution of 2 mM 5,5'-dithio-bis(2-nitrobenzoic acid) (DTNB) in 50 mM sodium acetate was prepared and refrigerated until use. Samples of each polymer were dissolved in dimethyl sulfoxide (DMSO), treated with 50 µL of a 2 mM DTNB solution, and then incubated for 5 min at room temperature. The optical density of the solution was measured at 414 nm. Thiol content was calculated using N-acetyl cysteine standards.

4. Characterization of No Release from S-nitrosothiol-Modified Hyperbranched Polyesters S-Nitrosothiol-functionalized hyperbranched polyesters were added to 30 mL deoxygenated 500 µM DTPA-supplemented phosphate buffered saline (PBS) or regular (DTPA-free) PBS at 37° C. Nitrogen was bubbled through this solution at a flow rate of 70 mL min$^{-1}$ to carry the liberated NO to a Sievers chemiluminescence nitric oxide analyzer (Boulder, Colo.). Additional nitrogen flow was supplied to the flask to match the collection rate of the instrument at 200 mL min$^{-1}$. The real-time NO-release profiles triggered by copper (0.2 mg mL$^{-1}$ CuBr$_2$), heat (37° C., shielded from light), or light (37° C., 200 W, 15 cm above the reaction flask) were recorded until the observed NO levels decreased below 10 ppb mg$^{-1}$ polyesters (P. N. Coneski and M. H. Schoenfisch, *Chem. Soc. Rev.*, 2012, 41, 3753-3758; E. M. Hetrick and M. H. Schoenfisch, *Annu. Rev. Anal. Chem.*, 2009, 2, 409-433).

5. Synthesis of Second Generation thiol-Modified Hyperbranched Polyesters

Figure 2:
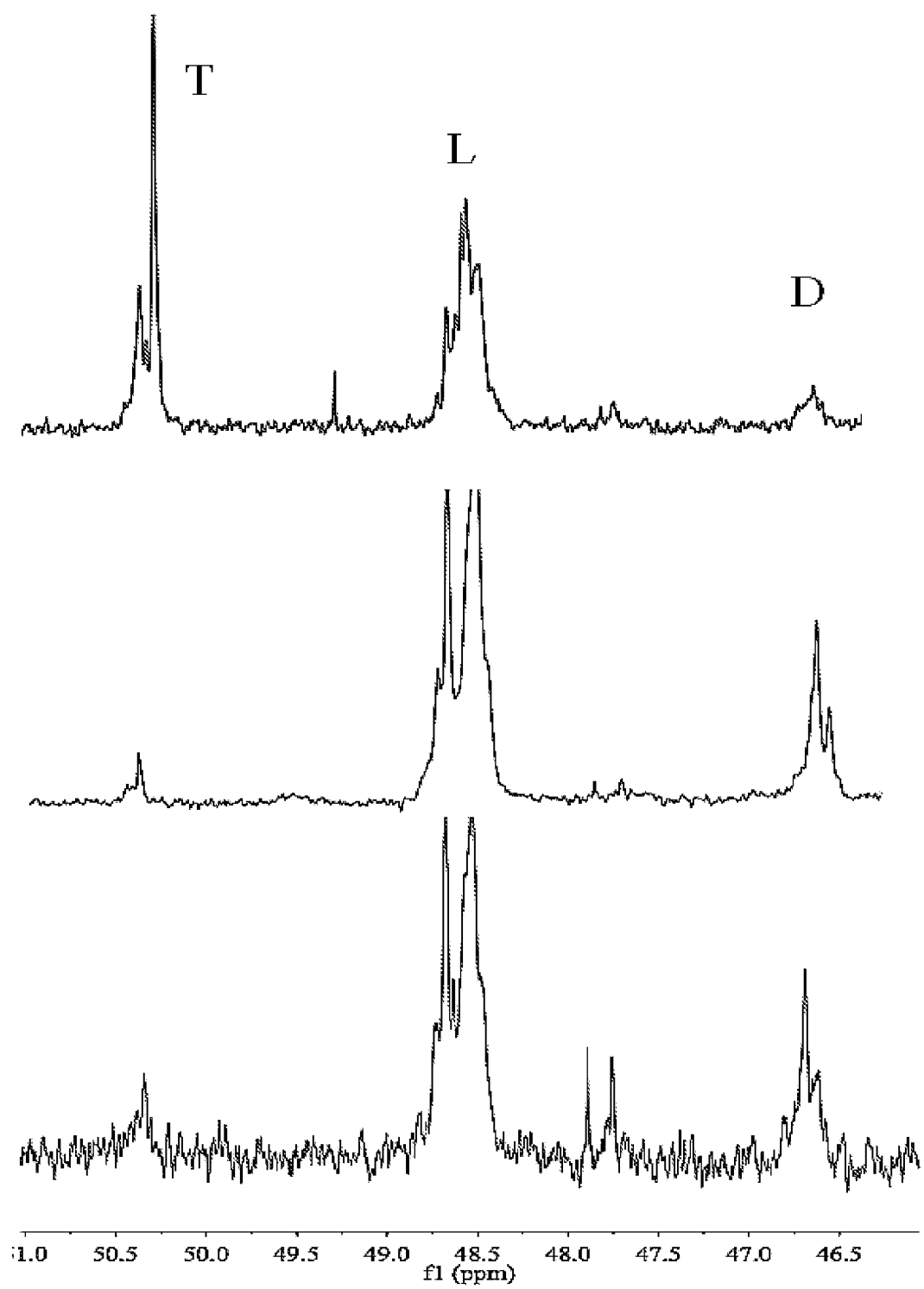
FIG. 2 shows representative $^{13}$C-NMR spectra of hyperbranched polyesters G2-HP (top), G3-HP (middle), and G4-HP (bottom).
Figure 3:
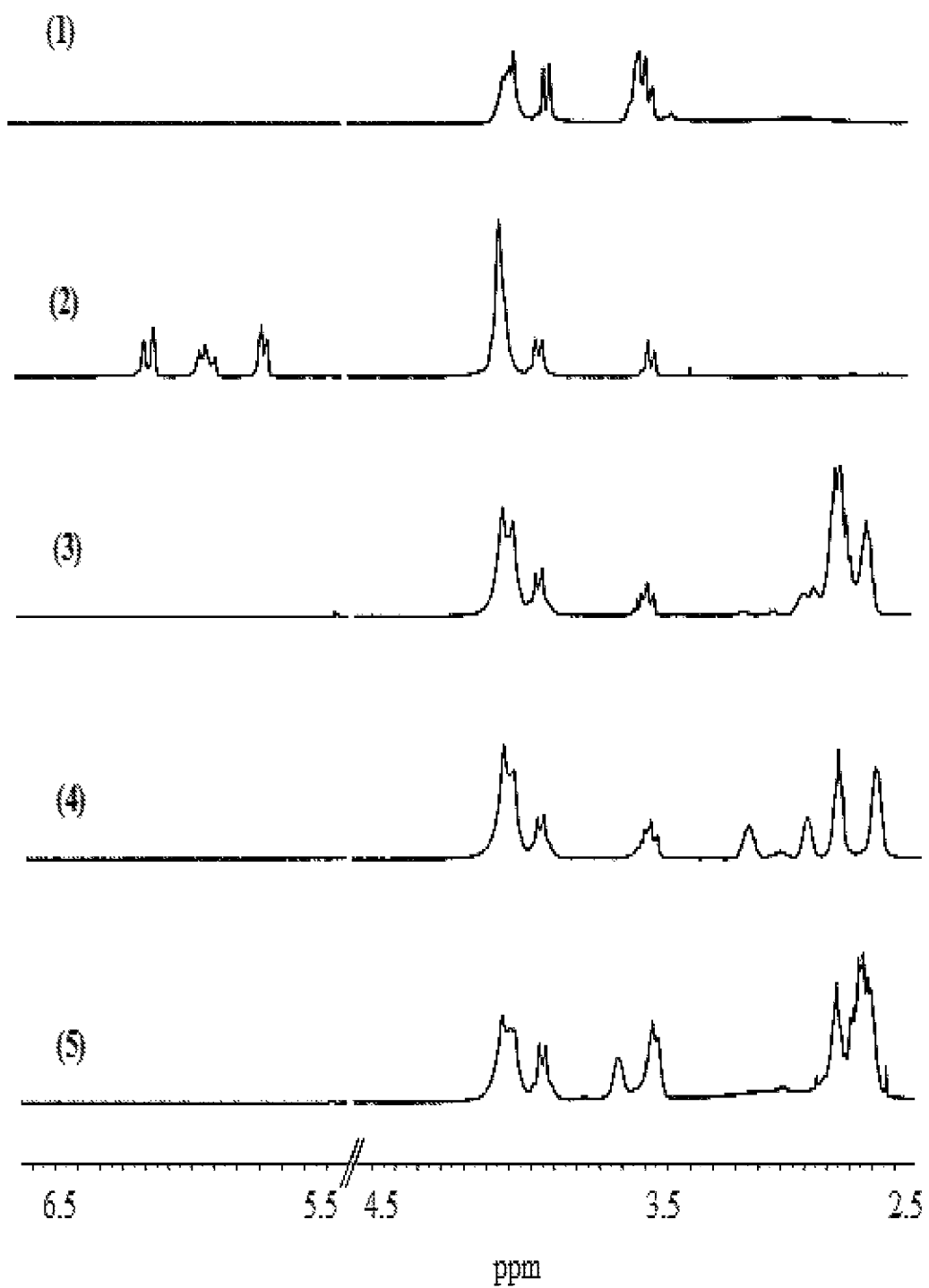
FIG. 3 shows representative $^1$H NMR spectra for G2-HP (1), acrylate-HP (2); 1,2-ethanedithiol (ET)-HP (3), 2,3-butanedithiol (BT)-HP (4), and dithiothreitol (DTT)-modified G2-HP (5).

Hyperbranched polyesters (HP) composed of bis-MPA were synthesized as described by Malmstrom et al. *Macromolecules*, 1995, 28, 1698-1703. The core molecule 2-ethyl-2-(hydroxymethyl)-1,3-propanediol (TMP) was reacted with bis-MPA at a molar ratio of 1:9 to yield second generation hyperbranched polyesters (G2-HP). Nuclear magnetic resonance (NMR) data confirmed the branching structure and the chemical composition of the polyesters. A typical hyperbranched polymer consists of three different structural units—dendritic (D), linear (L), and terminal (T) (FIG. 1). $^{13}$C NMR spectra (FIG. 2) and a simple calculation (see Equation 1 below) indicated that the degree of branching was ~0.44, corroborating a previous report (E. agar and M. igon, *Progress in Polymer Science*, 2011, 36, 53-88). By integrating the distinct $^1$H NMR resonance at 3.65 ppm (—CH$_2$OH) versus 4.10-4.30 ppm (—CH$_2$O) (FIG. 3, (1)), it was determined that ~8 HP hydroxyl groups on the G2-HP scaffold were available for subsequent chemical modification.

$$DB = \frac{\sum D + \sum T}{\sum D + \sum T + \sum L}. \quad \text{EQUATION 1}$$

Scheme 1. Synthesis of A) acrylate-; B) 1,2-ethanedithiol (ET)-; C) 2,3-butanedithiol (BT)-; D) dithiothreitol (DTT)-modified G2-HP.

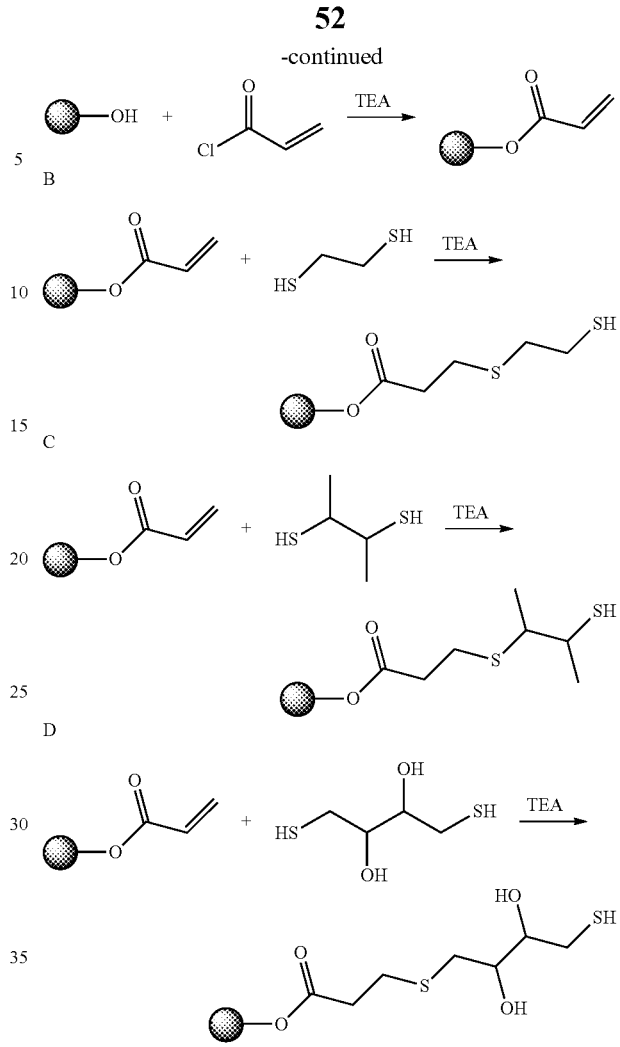

The exterior hydroxyl groups were next functionalized with acryloyl chloride to introduce alkene groups to the scaffold (Scheme 1A). Resonances for the alkene protons were split into three distinct peaks at 5.84, 6.07, and 6.27 ppm (FIG. 3, (2)) (H. Zhang, A. Patel, A. K. Gaharwar, S. M. Mihaila, G. Iviglia, S. Mukundan, H. Bae, H. Yang and A. Khademhosseini, *Biomacromolecules*, 2013, 14, 1299-1310). The resonance observed at 3.65 ppm corresponded to the methylene protons adjacent to unreacted peripheral hydroxyl groups and was integrated against the alkene resonances (5.84-6.27 ppm) to determine the molar ratio of hydroxyl groups to alkene bonds. The reaction efficiency of G2-HP with acryloyl chloride was roughly 70±7% with an average of 6 unsaturated double bonds per macromolecule. Subsequent reaction of the unsaturated double bonds with 1,2-ethanedithiol (ET), 2,3-butanedithiol (BT), or dithiothreitol (DTT) yielded either two primary (G2-HP-ET and G2-HP-DTT) or one secondary (G2-HP-BT) thiol-modified polyester(s) (Scheme 1B-D). All of the unsaturated double bonds were modified with thiols upon the completion of this reaction, as evidenced by the disappearance of the alkene proton resonances at 5.84, 6.07, and 6.27 ppm (FIGS. 3, (3), (4), and (5)). Dithiol addition was also confirmed by the appearance of peaks at 2.5 to 3 ppm, representing protons on the saturated double bonds and thiol groups (FIGS. 3, (3), (4), and (5)).).

TABLE 1

| Polyesters[a] | $M_n$ Theoretical[b] (g mol$^{-1}$) | $M_n$ Experimental[c] (g mol$^{-1}$) | PDI |
|---|---|---|---|
| G2-HP | 1179 | 1700 ± 180 | 1.32 ± 0.02 |
| G2-HP-ET | 2783 | 3510 ± 220 | 1.31 ± 0.04 |
| G2-HP-BT | 2867 | 4970 ± 940 | 1.33 ± 0.02 |
| G2-HP-DTT | 2986 | 2530 ± 570 | 1.39 ± 0.13 |

[a] n ≥ 3 separate syntheses;
[b] Theoretical molar mass of thiol-modified G2-HP derived from the experimental molar mass of G2-HP and ~6 dithiols modification for each polyesters.
[c] Molecular weight determined by GPC analysis.

Gel permeation chromatography (GPC) was used to determine the molecular weight (MW) of the hyperbranched polyesters. The similarity between the experimental molecular weight of G2-HP-DTT and the theoretical molar mass indicated negligible crosslinking of the DTT thiols during the reaction (Table 1). This result is most likely due to the reducing capacity of DTT (W. W. Cleland, *Biochem.*, 1964, 3, 480-482). A larger experimental molar mass was noted for both the G2-HP-ET and G2-HP-BT scaffolds relative to theoretical values, which may be attributed to crosslinking and/or inter-molecular bridging of the dithiols during the reaction (H. Nakamoto and J. C. A. Bardwell, *Biochimica et Biophysica Acta (BBA) Molecular Cell Research*, 2004, 1694, 111-119). To determine the extent of crosslinking, G2-HP-BT and G2-HP-ET were reacted with the reducing agent DTT overnight (~16 h), respectively. A slight decrease in molar mass was observed only for G2-HP-BT ($M_n$, 4000±400 g mol$^{-1}$), indicating potential crosslinking due to disulfide bond formation. Regardless, the still greater experimental molar mass for the reduced G2-HP-BT and G2-HP-ET suggests the formation of inter-molecular bridging between two polyester molecules. Although a 20× excess of dithiol relative to the number of double bonds on the hyperbranched polyester scaffolds was present during reaction, similar observations have been reported for thiol addition reactions (N. A. Stasko, T. H. Fischer and M. H. Schoenfisch, *Biomacromolecules*, 2008, 9, 834-841; J. P. Yapor, A. Lutzke, A. Pegalajar-Jurado, B. H. Neufeld, V. B. Damodaran and M. M. Reynolds, *J. Mater. Chem. B*, 2015, 3, 9233-9241; A. Lutzke, A. Pegalajar-Jurado, B. H. Neufeld and M. M. Reynolds, *J. Mater. Chem. B*, 2014, 2, 7449-7458). Despite the undesirable side reactions, the polyester scaffolds synthesis was reproducible and resulted in robust solubility in most organic solvents.

The free thiol content available for subsequent nitrosation and NO storage was determined using the Ellman's assay (Table 2). Each polyester scaffold exhibited large free thiol content (>2 µmol mg$^{-1}$), indicating the potential for large NO payloads compared to the polyesters reported by Yapor et al. *J. Mater. Chem. B*, 2015, 3, 9233-9241 (~0.9 µmol mg$^{-1}$). Of note, the similar thiol availability for each exterior modification also suggested negligible effects from disulfide and inter-molecular bridge bonding.

6. S-nitrosothiol-Modified G2-Hyperbranched Polyesters

Thiol-modified G2-hyperbranched polyesters were nitrosated using sodium nitrite in acidic solutions to produce NO-releasing polyesters (T. Liu, W. Zhang, X. Yang and C. Li, *J. Colloid Interface Sci.*, 2015, 459, 115-122; V. B. Damodaran and M. M. Reynolds, *J. Mater. Chem.*, 2011, 21, 5870-5872; D. A. Riccio, P. N. Coneski, S. P. Nichols, A. D. Broadnax and M. H. Schoenfisch, *ACS Appl. Mater. Interfaces*, 2012, 4, 796-804). Acetone was selected as the solvent to dissolve G2-HP-ET, G2-HP-BT or G2-HP-DTT before adding the nitrosating agent (i.e., NaNO$_2$/HCl). Due to the susceptibility of ester bonds to hydrolysis under acidic condition, GPC was used to characterize the stability of the polyesters during the nitrosation reaction. All of the polyester systems studied retained similar molecular weight and PDI, indicating negligible hydrolysis. In fact, a minor peak representing a greater molecular weight species became apparent over time, upon RSNO decomposition. Without wishing to be bound by theory, this feature may be attributed to polyesters bound by disulfide linkages. Accordingly, the minor hydrolysis of the polyesters may be the result of using an aprotic solvent (i.e., acetone) and low reaction temperatures (0° C.). Previous reports have also demonstrated that polyesters were resistant to acidic degradation during nitrosation, albeit at a low hydrochloric acid concentration (T. Liu, W. Zhang, X. Yang and C. Li, *J. Colloid Interface Sci.*, 2015, 459, 115-122; V. B. Damodaran and M. M. Reynolds, *J. Mater. Chem.*, 2011, 21, 5870-5872).

Figures 4A, 4B:
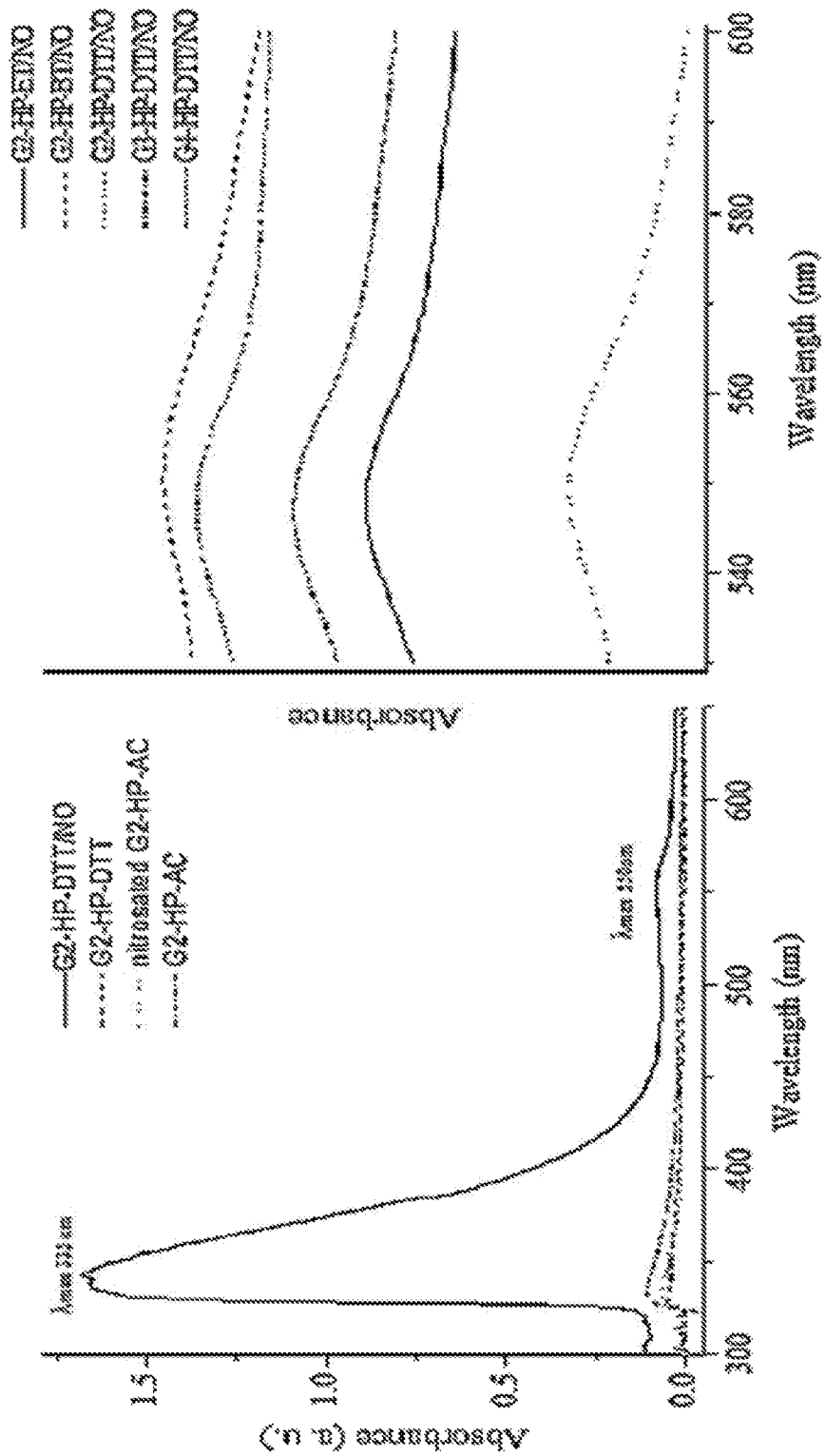
FIG. 4A and FIG. 4B show representative UV-vis spectra of S-nitrosothiol-modified hyperbranched polyesters measured in acetone (0.1 mg/mL). Specifically, a comparison between G2-HP-DTT and G2-HP-AC (4A) and characteristic S-nitrosothiol bands (4B) are shown.

The formation of S-nitrosothiol on the polyesters (G2-HP-ET/NO, G2-HP-BT/NO, and G2-HP-DTT/NO) was confirmed by UV-vis absorption spectroscopy. The peaks at ~340 nm (intense) and ~550 nm (broad) correspond to the S-nitrosothiol $n_O$-$\pi^*$ and $n_N$-$\pi^*$ transitions, respectively (FIG. 4A and FIG. 4B) (A. B. Seabra, D. Martins, M. M. S. G. Simoes, R. da Silva, M. Brocchi and M. G. de Oliveira, *Artif. Organs*, 2010, 34, E204-E214; A. Lutzke, A. Pegalajar-Jurado, B. H. Neufeld and M. M. Reynolds, *J. Mater. Chem. B*, 2014, 2, 7449-7458; D. L. H. Williams, *Acc. Chem. Res.*, 1999, 32, 869-876). Indeed, the red color of the nitrosated polyesters (associated with the peak at ~550 nm) clearly affirm formation of the NO donor (FIG. 4B). Moreover, hydroxyl groups may react with nitrosating reagents to form alkyl nitrites (D. L. H. Williams, *Nitrosation reactions and the chemistry of nitric oxide*, Elsevier, 2004). To investigate the potential reactivity of unmodified hydroxyl groups associated with the polyester, G2-HP-AC (the intermediate prior to thiol modification) was nitrosated following the same protocol. As shown in FIG. 4A, the absorption peaks typically associated with alkyl nitrite formation (in the 300-400 nm region) were not present for either G2-HP-DTT/NO or nitrosated G2-HP-AC. These results confirm that the S-nitrosothiol moiety is the primary functional group introduced by the nitrosation process (D. L. H. Williams, *Nitrosation reactions and the chemistry of nitric oxide*, Elsevier, 2004).

Figure 5A:
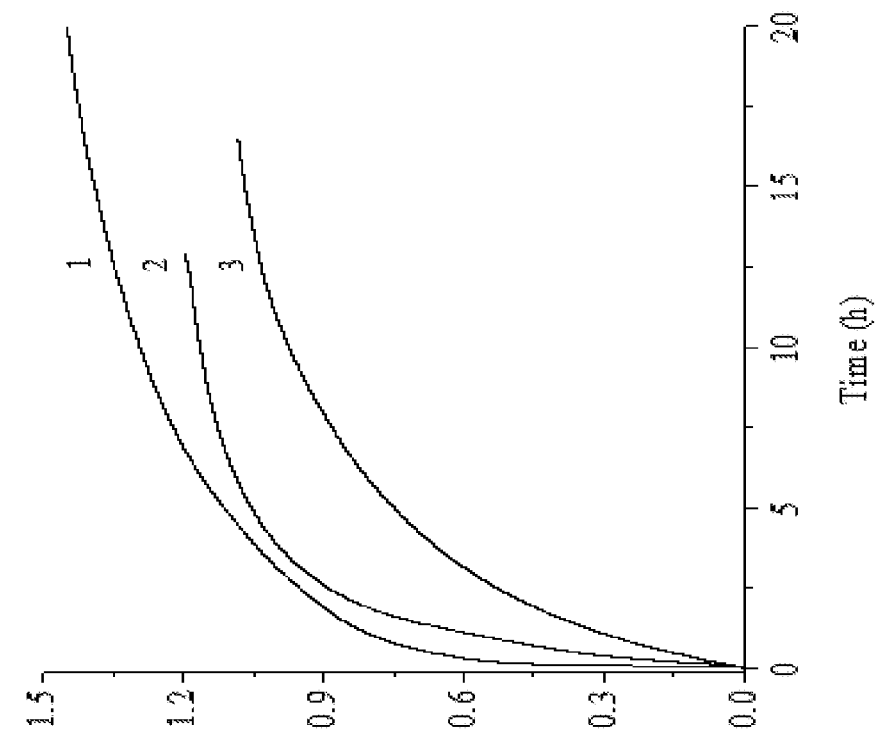
FIG. 5A and FIG. 5B show representative images illustrating total nitric oxide release from G2-HP-ET/NO (1), G2-HP-BT/NO (2), and G2-HP-DTT/NO (3) in either 0.2 mg/mL $CuBr_2$ solution (37° C., pH 7.4) (5A) or DTPA-supplemented PBS solution shielded from light (37° C., pH 7.4) (5B).
Figure 5B:
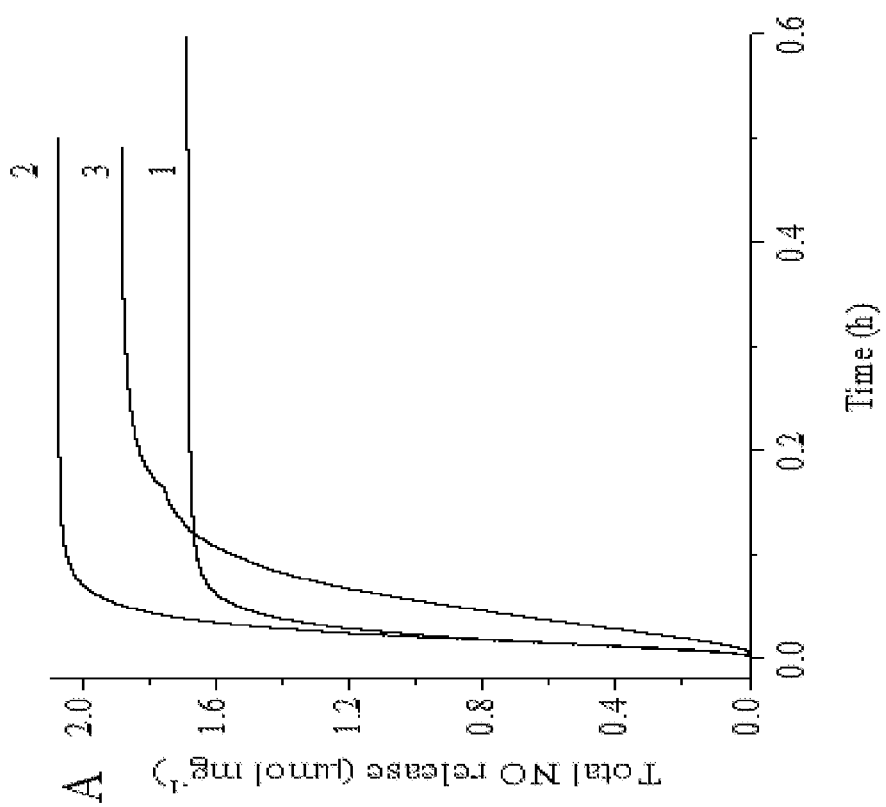

The total NO storage for each S-nitrosothiol modification was measured in a copper bromide (0.2 mg mL$^{-1}$, 37° C., pH 7.4) supplemented phosphate buffered saline (PBS) solution under dark conditions. Although blood and tissue contain only trace levels of copper ions (Cu$^{2+}$) (T. V. O'Halloran and V. C. Culotta, *J. Biol. Chem.*, 2000, 275, 25057-25060), the rapid NO release triggered by S-nitrosothiol (RSNO) reaction with Cu$^{2+}$ is helpful in assessing total NO payloads (FIG. 5A). As shown in Table 2, similar nitrosation efficiencies (~70%) were observed regardless of exterior modification. The total NO storage for each scaffold was ~2 µmol mg$^{-1}$ and directly correlated with the high free thiol content measured for the thiol-modified G2-HP systems (Table 2). Indeed, these levels are significantly greater than the previously reported NO-releasing polyester-based materials (~0.45 µmol mg$^{-1}$) (J. P. Yapor, A. Lutzke, A. Pegalajar-Jurado, B. H. Neufeld, V. B. Damodaran and M. M. Reynolds, *J. Mater. Chem. B*, 2015, 3, 9233-9241).

TABLE 2

| Polyesters[a] | Thiol content[b] ($\mu$mol mg$^{-1}$) | t[NO][c] ($\mu$mol mg$^{-1}$) | Nitrosation efficiency[d] (%) |
|---|---|---|---|
| G2-HP-ET | 1.96 ± 0.04 | 1.60 ± 0.27 | 81.8 ± 13.7 |
| G2-HP-BT | 2.38 ± 0.07 | 1.97 ± 0.41 | 82.8 ± 17.2 |
| G2-HP-DTT | 2.20 ± 0.17 | 1.84 ± 0.21 | 83.6 ± 9.5 |

[a]n ≥ 3 separate syntheses;
[b]Thiol content determined by Ellman's assay;
[c]NO-release totals measured in 0.2 mg mL$^{-1}$ CuBr$_2$-supplemented PBS solution.
[d]Nitrosation efficiency calculated from dividing NO totals by thiol content.

The NO-release properties of the hyperbranched polyesters were initially evaluated in PBS solution (37° C., pH 7.4) without the presence of a copper chelator (e.g., DTPA). Regardless of the S-nitrosothiol modification, each scaffold exhibited rapid NO-release kinetics and comparable NO-release half-lives (~5 min) under light irradiation (Table 3). Similar NO-release kinetics ($t_{1/2}$<10 min) were still observed for each scaffold modification in the absence of light. This rapid NO release was attributed to copper and more specifically, copper ion-mediated S-nitrosothiol breakdown. The relatively high levels of copper present in untreated PBS (21.5 ppm $Cu^{2+}$ as measured via inductively coupled plasma-optical emission spectrometry) oxidized residual thiolate ions, resulting in $Cu^+$-mediated RSNO decomposition (D. L. H. Williams, *Acc. Chem. Res.*, 1999, 32, 869-876).

TABLE 3[a]

| | | G2-HP-ET/NO | | G2-HP-BT/NO | | G2-HP-DTT/NO | |
|---|---|---|---|---|---|---|---|
| DTPA | Light | t[NO][b] ($\mu$mol/mg) | $t_{1/2}$[c] (min) | t[NO][b] ($\mu$mol/mg) | $t_{1/2}$[c] (min) | t[NO][b] ($\mu$mol/mg) | $t_{1/2}$[c] (min) |
| Yes | No | 1.40 ± 0.17 | 84 ± 24 | 0.99 ± 0.20 | 190 ± 46 | 1.47 ± 0.24 | 53 ± 28 |
| Yes | Yes | 1.55 ± 0.22 | 36 ± 16 | 1.14 ± 0.24 | 75 ± 19 | 1.43 ± 0.10 | 42 ± 12 |
| No | No | 1.40 ± 0.15 | 5 ± 2 | 1.90 ± 0.29 | 10 ± 2 | 1.73 ± 0.17 | 7 ± 2 |
| No | Yes | 1.65 ± 0.10 | 5 ± 2 | 1.79 ± 0.12 | 5 ± 3 | 1.69 ± 0.24 | 6 ± 3 |

[a]n ≥ 3 separate syntheses;
[b]Total NO storage per milligram polyesters;
[c]Half-life of NO release.

As a result of significantly lower basal $Cu^{2+}$ levels in the human body, RSNO decomposition under physiological condition will likely be restricted to a thermal RSNO-breakdown mechanism (T. V. O'Halloran and V. C. Culotta, *J. Biol. Chem.*, 2000, 275, 25057-25060; M. Valko, H. Morris and M. T. D. Cronin, *Curr. Med. Chem.*, 2005, 12, 1161-1208). To better understand such behavior, NO release from the polyesters was evaluated in the absence of light and copper by supplementing the PBS with 500 $\mu$M diethylene triamine pentaacetic acid (DTPA). Secondary RSNO G2-HP-BT/NO polyesters exhibited both significantly lower NO-release totals and extended NO-release kinetics compared to both primary RSNOs (either G2-HP-ET/NO or G2-HP-DTT/NO; Table 3). Previous studies have demonstrated that methyl groups of secondary thiols act as electron-donating groups, enhancing the stability of the corresponding RSNOs compared to their primary thiol counterparts (e.g., ET and DTT) (B. Roy, A. Du Moulinet d'Hardemare and M. Fontecave, *J. Org. Chem.*, 1994, 59, 7019-7026). As thermal RSNO decomposition results in homolytic cleavage of the S—N bond (yielding thiyl and NO radicals) (D. L. H. Williams, *Acc. Chem. Res.*, 1999, 32, 869-876), increased stability from the secondary thiol (BT) may facilitate the recombination of this geminate radical pair and slow the NO donor breakdown (FIG. 2B) (S. M. Shishido and M. G. Oliveira, *Photochem. Photobiol.*, 2000, 71, 273-280). On the other hand, the more compact structure of primary thiol polyesters scaffold (e.g., G2-HP-ET) should enhance RSNO stability (N. A. Stasko, T. H. Fischer and M. H. Schoenfisch, *Biomacromolecules*, 2008, 9, 834-841; Y. Lu, A. Shah, R. A. Hunter, R. J. Soto and M. H. Schoenfisch, *Acta Biomater.*, 2015, 12, 62-69). Indeed, a slight increase in half-life was observed for G2-HP-ET/NO (~84 min) compared to G2-HP-DTT/NO (~54 min), corroborating this concept. However, the electron-donating effect of the secondary thiol was found to be more significant in enhancing RSNO stability compared to the compact structure, as evidenced by the extended NO-release kinetics of G2-HP-BT/NO system.

The photolysis mechanism of S-nitrosothiol breakdown was also studied in PBS supplemented with DTPA using a broad-spectrum white light source at a power of 200 W (15 cm above the reaction flask). As expected, light triggered more rapid RSNO decomposition and NO release than thermal decomposition alone for each S-nitrosothiol system, corroborating previous reports of similar behavior for S-nitrosothiol-modified macromolecular scaffolds (N. A. Stasko, T. H. Fischer and M. H. Schoenfisch, *Biomacromolecules*, 2008, 9, 834-841; Y. Lu, A. Shah, R. A. Hunter, R. J. Soto and M. H. Schoenfisch, *Acta Biomater.*, 2015, 12, 62-69; D. A. Riccio, J. L. Nugent and M. H. Schoenfisch, *Chem. Mater.*, 2011, 23, 1727-1735). Despite the more rapid NO release, the secondary RSNO scaffold (G2-HP-BT/NO) still exhibited the slowest NO release, again attributed to enhanced RSNO stability due to favorable electron donating from the methyl groups adjacent to the S-nitrosothiol. Of note, both primary RSNO scaffolds (G2-HP-ET/NO and G2-HP-DTT/NO) were characterized by accelerated RSNO decomposition with light, resulting in similar NO-release kinetics ($t_{1/2}$~40 min) (N. A. Stasko, T. H. Fischer and M. H. Schoenfisch, *Biomacromolecules*, 2008, 9, 834-841). In DTPA-supplemented PBS, evaluation of the NO-release characteristics of the G2-HP scaffolds with the different thiol modifications (i.e., ET, BT, and DTT) demonstrated that both the electron-donating groups of secondary thiols and the compact structure of primary thiols enhanced RSNO stability under thermal decomposition conditions, while the NO release under light was only prolonged using NO donors with secondary thiol structures.

7. Higher Generation S-nitrosothiol-Modified Hyperbranched Polyesters

Larger molecular weight (i.e., higher generation) hyperbranched polyesters modified with S-nitrosothiol NO donors were also synthesized to evaluate the effect of polyesters generation (i.e., size) on NO-release properties. Specifically, G3 and G4-HP were synthesized using TMP to bis-MPA ratios of 1:21 and 1:45, respectively. The theoretical number of hydroxyl groups available for subsequent chemical modification for these polyesters was determined using $^1$H NMR to be ~18 for G3-HP and ~40 for G4-HP. The $^{13}$C NMR data (FIG. 2) indicated a decrease in the degree of branching for the G3-HP (~0.25) and G4-HP (~0.22) scaffolds compared to G2-HP (~0.44). Without wishing to be bound by theory, the altered branching may be the result of increased reaction mixture viscosity at higher generations, thus hindering molecule diffusion during the one-pot reaction and reducing linear unit reactivity relative to dendritic units (E. agar and M. igon, *Progress in Polymer Science*, 2011, 36, 53-88).

Figure 6A:
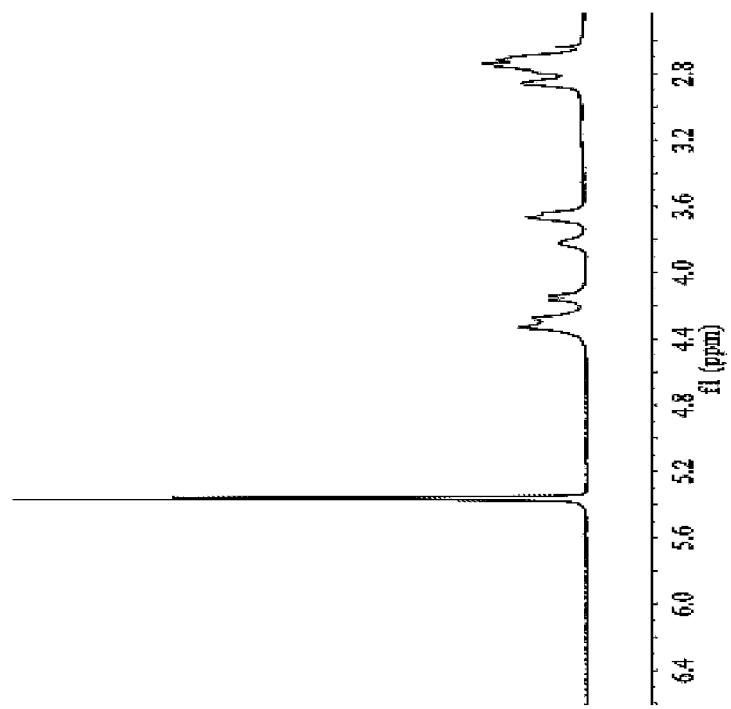
FIG. 6A and FIG. 6B show representative $^1$H NMR spectra of G3-HP-DTT (6A) and G4-HP-DTT (6B).
Figure 6B:
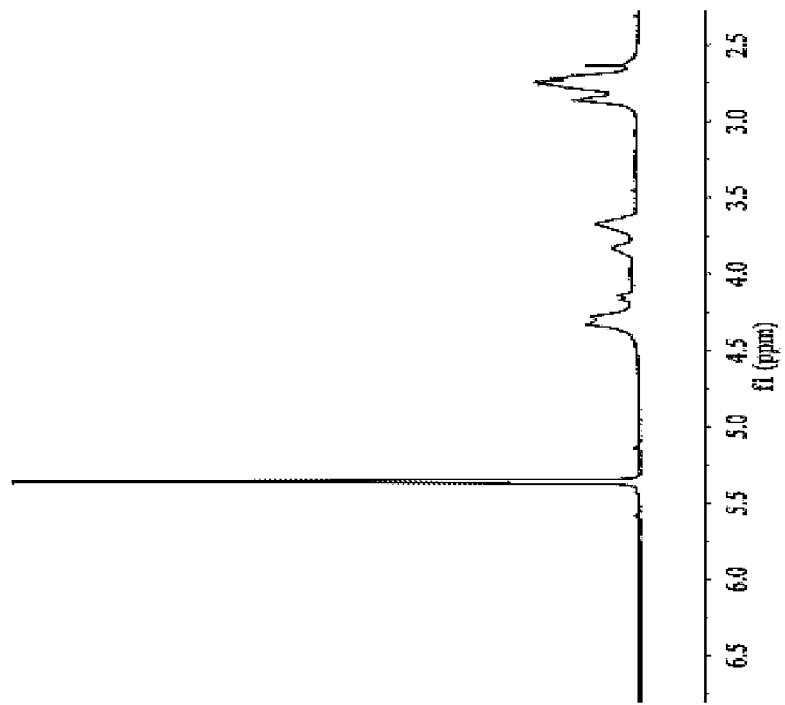
Figure 7:
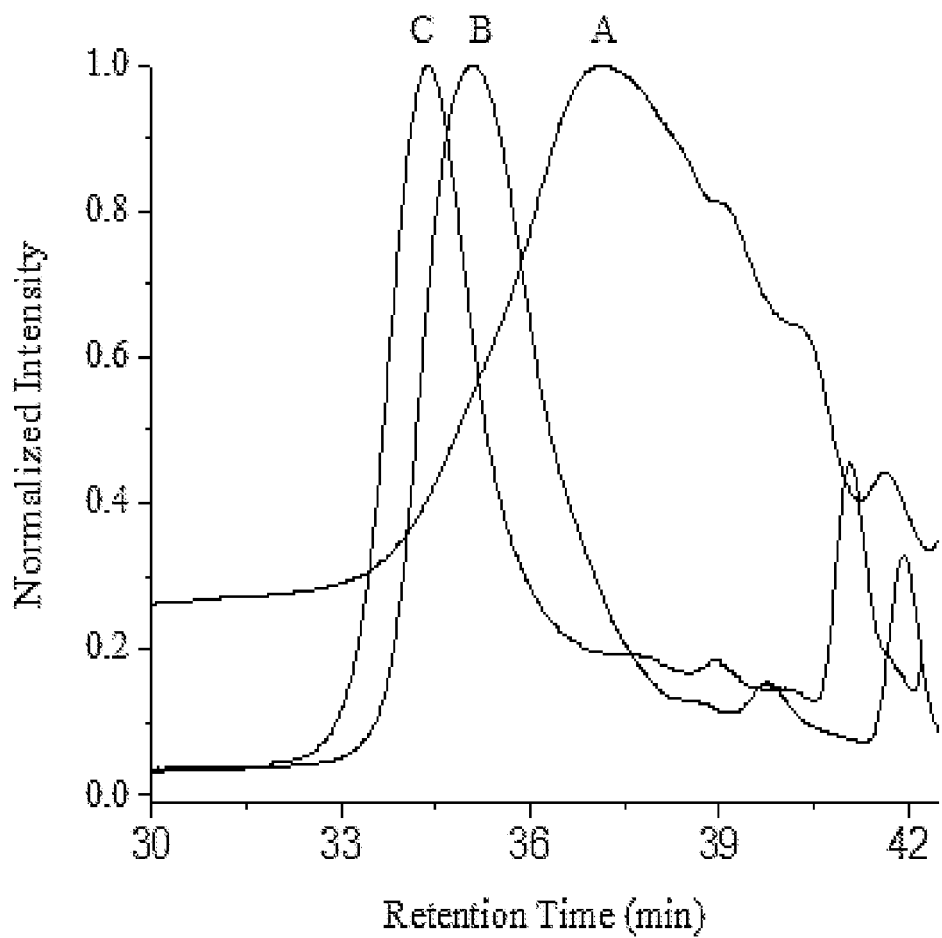
FIG. 7 shows representative GPC chromatograms of G2-HP-DTT (A), G3-HP-DTT (B), and G4-HP-DTT (C).
Figure 8D:
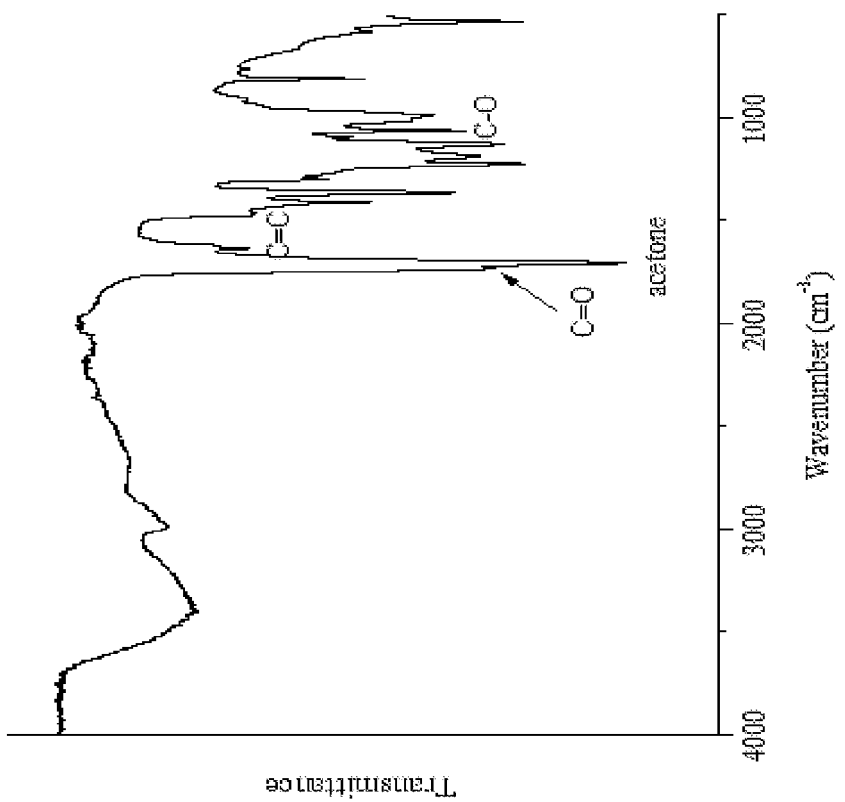
Figure 8C:
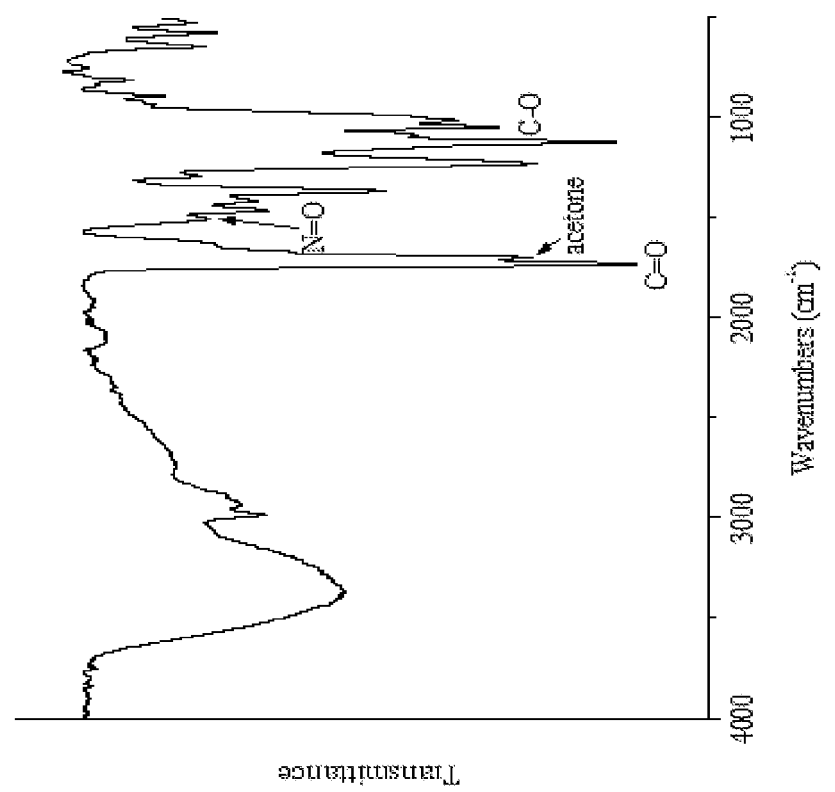

The subsequent acryloyl chloride conversion efficiency was found to be 56±6 and 66±8% for G3-HP and G4-HP, respectively, corresponding to an average of ~10 and 28 double bonds per scaffold. The G3-HP and G4-HP polyesters were then modified with DTT. As expected, any evidence of remaining double bonds was lost following this reaction (FIG. 6A and FIG. 6B), again conveying successful DTT modification. Greater molecular weights were measured by GPC for both the unmodified and DTT-modified scaffolds with each increase in scaffold generation (Table 4). While similar theoretical and experimental molecular weights were determined for the G2-HP and G3-HP scaffolds, the experimental MW for G4-HP was significantly lower than the theoretical value. Indeed, such error is the result of linear polystyrene-based GPC calibration standards, which inherently underestimates the molecular weights of the more globular-like hyperbranched polyesters (X. Zhai, S. Peleshanko, N. S. Klimenko, K. L. Genson, D. Vaknin, M. Y. Vortman, V. V. Shevchenko and V. V. Tsukruk, *Macromolecules*, 2003, 36, 3101-3110). This effect is more pronounced at higher generation or larger molar mass polymers (D. A. Riccio, J. L. Nugent and M. H. Schoenfisch, *Chem. Mater.*, 2011, 23, 1727-1735). Two distinct peaks were observed in the GPC chromatograms for G3-HP-DTT and G4-HP-DTT (FIG. 7) that can be assigned to the modified polyesters (major peak) and unreactive polyether oligomers (minor peak). The unreactive polyether oligomers ($M_n$<2000 g mol$^{-1}$) were expected from side reactions occurring during the one-pot synthesis of hyperbranched polyesters (E. agar and M. igon, *Progress in Polymer Science*, 2011, 36, 53-88). Relative to their unmodified counterparts, the G3-HP-DTT and G4-HP-DTT were characterized as having lower PDI values as they lacked the byproduct peak from the molecular weight analysis. Resolution of these peaks was not observed for G2-HP-DTT because of similar molar mass to the unreactive oligomers. As such, G2-HP and G2-HP-DTT had similar PDI values.

TABLE 4

| Polyesters[a] | $M_n$ Theoretical[b] (g mol$^{-1}$) | $M_n$ Experimental[c] (g mol$^{-1}$) | PDI |
|---|---|---|---|
| G2-HP | 1179 | 1700 ± 180 | 1.32 ± 0.02 |
| G2-HP-DTT | 2986 | 2530 ± 580 | 1.39 ± 0.13 |
| G3-HP | 2573 | 2820 ± 270 | 1.44 ± 0.13 |

TABLE 4-continued

| Polyesters[a] | $M_n$ Theoretical[b] (g mol$^{-1}$) | $M_n$ Experimental[c] (g mol$^{-1}$) | PDI |
|---|---|---|---|
| G3-HP-DTT | 4950 | 4430 ± 260 | 1.28 ± 0.12 |
| G4-HP | 5359 | 3570 ± 420 | 1.56 ± 0.11 |
| G4-HP-DTT | 9525 | 6240 ± 980 | 1.12 ± 0.00 |

[a]n ≥ 3 separate syntheses.
[b]Theoretical molar mass of thiol-modified HP derived from the experimental molar mass of HP and corresponding amount of dithiols modification for each polyesters.
[c]Molecular weight determined by GPC.

TABLE 5

| Polyesters[a] | Thiol content[b] (µmol mg$^{-1}$) | t[NO][c] (µmol mg$^{-1}$) | Nitrosation efficiency[d] (%) |
|---|---|---|---|
| G2-HP-DTT | 2.20 ± 0.17 | 1.84 ± 0.21 | 83.6 ± 9.5 |
| G3-HP-DTT | 1.85 ± 0.16 | 1.48 ± 0.29 | 79.8 ± 15.6 |
| G4-HP-DTT | 2.15 ± 0.13 | 1.84 ± 0.16 | 85.5 ± 7.8 |

[a]n ≥ 3 separate syntheses;
[b]Thiol content determined by Ellman's assay;
[c]NO-release total amounts measured in 0.2 mg mL$^{-1}$ CuBr$_2$-supplemented PBS solution.
[d]Nitrosation efficiency calculated from dividing NO totals by thiol content.

Although G2-HP-DTT and G4-HP-DTT exhibited similar thiol content, the thiol levels for the G3-HP-DTT scaffold was noticeably less (Table 5). This decrease is attributed to lower acryloyl chloride modification efficiency. The success of S-nitrosothiol functional group addition was again examined by UV-vis spectroscopy (FIG. 4B). The appearance of a characteristic absorption band at ~550 nm confirmed S-nitrosothiol formation. G3-HP-AC (the intermediate prior to thiol incorporation) was also nitrosated to rule out potential alkyl nitrite formation. The UV-vis absorption spectra for G3-HP-AC and nitrosated G3-HP-AC were again nearly identical, showing no evidence of alkyl nitrite formation (data not shown). FTIR spectroscopy indicated an additional peak at 1520 cm$^{-1}$ for G3-HP-DTT/NO that was absent for G3-HP-DTT. This peak is attributed to the S—N═O stretching vibration (FIG. 8A-D; a droplet of highly concentrated polyesters acetone solution was added onto the ATR-FTIR stage, and the spectra were collected via ATR mode) (T. Liu, W. Zhang, X. Yang and C. Li, *J. Colloid Interface Sci.*, 2015, 459, 115-122; P. N. Coneski, K. S. Rao and M. H. Schoenfisch, *Biomacromolecules*, 2010, 11, 3208-3215). Furthermore, the sharp but weak peak at 2550 cm$^{-1}$ resulting from S—H stretching, was no longer observed after nitrosation. In contrast, no differences were observed between nitrosated G3-HP-AC and G3-HP-AC, demonstrating that the hydroxyl groups are not reactive under the nitrosation conditions employed. The preservation of peaks at 3400 cm$^{-1}$ for both G3-HP-DTT/NO and nitrosated G3-HP-AC (i.e., hydroxyl groups of polyesters) further supports this.

TABLE 6[a]

| DTPA | Light | G2-HP-DTT/NO t[NO][b] (μmol/mg) | G2-HP-DTT/NO $t_{1/2}$[c] (min) | G3-HP-DTT/NO t[NO][b] (μmol/mg) | G3-HP-DTT/NO $t_{1/2}$[c] (min) | G4-HP-DTT/NO t[NO][b] (μmol/mg) | G4-HP-DTT/NO $t_{1/2}$[c] (min) |
|---|---|---|---|---|---|---|---|
| Yes | No | 1.47 ± 0.24 | 56 ± 24 | 1.26 ± 0.39 | 70 ± 29 | 1.53 ± 0.04 | 171 ± 56 |
| Yes | Yes | 1.43 ± 0.10 | 42 ± 12 | 1.05 ± 0.20 | 42 ± 15 | 1.43 ± 0.10 | 132 ± 35 |
| No | No | 1.73 ± 0.17 | 7 ± 2 | 1.47 ± 0.32 | 4 ± 2 | 1.83 ± 0.18 | 7 ± 3 |
| No | Yes | 1.69 ± 0.24 | 6 ± 3 | 1.50 ± 0.42 | 3 ± 1 | 1.90 ± 0.22 | 9 ± 3 |

[a] n ≥ 3 separate syntheses;
[b] Total NO storage per milligram polyesters;
[c] Half-life of NO release.

Lastly, the NO-release properties of the HP-DTT/NO polyesters were evaluated as a function of scaffold size (Table 5, Table 6). As might be expected based on the smaller thiol levels, G3-HP-DTT/NO exhibited slightly lower NO payloads relative to G4-HP-DTT/NO. Nevertheless, the nitrosation efficiency (capacity to form NO donors) was similar regardless of scaffold size. In PBS without a copper chelator, the NO-release kinetics were similar regardless of size, with light irradiation having little effect on NO release ($t_{1/2}$<10 min). However, the NO-release kinetics were highly dependent on polyester generation in DTPA-supplemented PBS. In the absence of light irradiation, larger sizes led to longer NO-release for the three sizes investigated (i.e., G2, G3, and G4). In this manner, the extended NO-release kinetics for the G3-HP-DTT/NO and G4-HP-DTT/NO scaffolds were attributed to differences in the RSNO microenvironment between the generations. As illustrated below (see Table 7), the polyester suspensions exhibited similar hydrodynamic (DLS) sizes regardless of generation. The inherent greater density of RSNO donors (number of RSNO groups per hydrodynamic radius) for G4-HP-DTT/NO cultivated the recombination of geminate radical pairs (i.e., cage effect) (T. Liu, W. Zhang, X. Yang and C. Li, *J. Colloid Interface Sci.*, 2015, 459, 115-122; S. M. Shishido and M. G. Oliveira, *Photochem. Photobiol.*, 2000, 71, 273-280), thus slowing NO release. The faster NO release was observed for the lowest RSNO density system (i.e., G2-HP-DTT/NO). Light irradiation mitigated these differences, particularly for the G2-HP-DTT/NO and G3-HP-DTT/NO systems, due to the acceleration of RSNO decomposition (N. A. Stasko, T. H. Fischer and M. H. Schoenfisch, *Biomacromolecules*, 2008, 9, 834-841). Of potential importance, G4-HP-DTT/NO polyesters still maintained the longest NO-release duration with light, indicating the importance of RSNO donor stability.

TABLE 7

| Polyesters[a] | Hydrodynamic size (nm)[b] | PDI |
|---|---|---|
| G2-HP-DTT/NO | 1170 ± 160 | 0.12 ± 0.07 |
| G3-HP-DTT/NO | 1050 ± 180 | 0.10 ± 0.07 |
| G4-HP-DTT/NO | 987 ± 150 | 0.09 ± 0.06 |

[a] n ≥ 3 separate syntheses.
[b] As determined by Dynamic Light Scattering. The concentration of NO-releasing scaffold in PBS solution for DLS measurement was the same with for NO analyzer measurement (0.33 mg mL$^{-1}$).

REFERENCES

J. P. Cooke, *Atherosclerosis Suppl.*, 2003, 4, 53-60.
D. D. Rees, R. M. Palmer and S. Moncada, *Proc. Natl. Acad. Sci.*, 1989, 86, 3375-3378.
J.-d. Luo and A. F. Chen, *Acta Pharmacol. Sin.*, 2005, 26, 259-264.
M. R. Schïffer, U. Tantry, S. S. Gross, H. L. Wasserkrug and A. Barbul, *J. Surg. Res.*, 1996, 63, 237-240.
C. Bogdan, *Nat. Immunol.*, 2001, 2, 907-916.
J. MacMicking, Q.-w. Xie and C. Nathan, *Annu. Rev. Immunol.*, 1997, 15, 323-350.
A. W. Carpenter and M. H. Schoenfisch, *Chem. Soc. Rev.*, 2012, 41, 3742-3752.
P. N. Coneski and M. H. Schoenfisch, *Chem. Soc. Rev.*, 2012, 41, 3753-3758.
S. P. Nichols, W. L. Storm, A. Koh and M. H. Schoenfisch, *Adv. Drug Delivery Rev.*, 2012, 64, 1177-1188.
D. A. Riccio and M. H. Schoenfisch, *Chem. Soc. Rev.*, 2012, 41, 3731-3741.
P. N. Coneski and M. H. Schoenfisch, *Poly. Chem.*, 2011, 2, 906-913.
D. Lyn H áWilliams, *Chem. Soc. Rev.*, 1985, 14, 171-196.
H. P. Zhang, G. M. Annich, J. Miskulin, K. Stankiewicz, K. Osterholzer, S. I. Merz, R. H. Bartlett and M. E. Meyerhoff, *J. Am. Chem. Soc.*, 2003, 125, 5015-5024.
Y. Lu, D. L. Slomberg, B. Sun and M. H. Schoenfisch, *Small*, 2013, 9, 2189-2198.
D. L. Slomberg, Y. Lu, A. D. Broadnax, R. A. Hunter, A. W. Carpenter and M. H. Schoenfisch, *ACS Appl. Mater. Interfaces*, 2013, 5, 9322-9329.
Y. Lu, D. L. Slomberg, A. Shah and M. H. Schoenfisch, *Biomacromolecules*, 2013, 14, 3589-3598.
B. Sun, D. L. Slomberg, S. L. Chudasama, Y. Lu and M. H. Schoenfisch, *Biomacromolecules*, 2012, 13, 3343-3354.
Y. Lu, B. Sun, C. Li and M. H. Schoenfisch, *Chem. Mater.*, 2011, 23, 4227-4233.
E. M. Hetrick, J. H. Shin, N. A. Stasko, C. B. Johnson, D. A. Wespe, E. Holmuhamedov and M. H. Schoenfisch, *ACS Nano*, 2008, 2, 235-246.
Z. R. Zhou, G. M. Annich, Y. D. Wu and M. E. Meyerhoff, *Biomacromolecules*, 2006, 7, 2565-2574.
M. C. Frost and M. E. Meyerhoff, *J. Biomed. Mater. Res., Part A*, 2005, 72A, 409-419.
N. A. Stasko, T. H. Fischer and M. H. Schoenfisch, *Biomacromolecules*, 2008, 9, 834-841.
R. J. Soto, L. Yang and M. H. Schoenfisch, *ACS Appl. Mater. Interfaces*, 2016, 8, 2220-2231.
B. V. Worley, D. L. Slomberg and M. H. Schoenfisch, *Bioconjugate Chem.*, 2014, 25, 918-927.
T. Liu, W. Zhang, X. Yang and C. Li, *J. Colloid Interface Sci.*, 2015, 459, 115-122.
P. N. Coneski, K. S. Rao and M. H. Schoenfisch, *Biomacromolecules*, 2010, 11, 3208-3215.
V. B. Damodaran and M. M. Reynolds, *J. Mater. Chem.*, 2011, 21, 5870-5872.

A. B. Seabra, D. Martins, M. M. S. G. Simoes, R. da Silva, M. Brocchi and M. G. de Oliveira, *Artif. Organs,* 2010, 34, E204-E214.

J. P. Yapor, A. Lutzke, A. Pegalajar-Jurado, B. H. Neufeld, V. B. Damodaran and M. M. Reynolds, *J. Mater. Chem. B,* 2015, 3, 9233-9241.

B. I. Voit and A. Lederer, *Chem. Rev.,* 2009, 109, 5924-5973.

Y. L. Xiao, H. Hong, A. Javadi, J. W. Engle, W. J. Xu, Y. A. Yang, Y. Zhang, T. E. Barnhart, W. B. Cai and S. Q. Gong, *Biomaterials,* 2012, 33, 3071-3082.

N. Feliu, M. V. Walter, M. I. Montanez, A. Kunzmann, A. Hult, A. Nystrom, M. Malkoch and B. Fadeel, *Biomaterials,* 2012, 33, 1970-1981.

A. Carlmark, E. Malmstrom and M. Malkoch, *Chem. Soc. Rev.,* 2013, 42, 5858-5879.

E. Malmström, M. Johansson and A. Hult, *Macromolecules,* 1995, 28, 1698-1703.

M. Prabaharan, J. J. Grailer, S. Pilla, D. A. Steeber and S. Q. Gong, *Biomaterials,* 2009, 30, 5757-5766.

X. H. Zeng, Y. N. Zhang and A. M. Nystrom, *Biomacromolecules,* 2012, 13, 3814-3822.

K. Karatasos, *J. Phys. Chem. B,* 2013, 117, 2564-2575.

E. Malmstrom, M. Johansson and A. Hult, *Macromolecules,* 1995, 28, 1698-1703.

G. Gabor and A. Vincze, *Anal. Chim. Acta,* 1977, 92, 429-431.

Y. Lu, A. Shah, R. A. Hunter, R. J. Soto and M. H. Schoenfisch, *Acta Biomater.,* 2015, 12, 62-69.

E. M. Hetrick and M. H. Schoenfisch, *Annu. Rev. Anal. Chem.,* 2009, 2, 409-433.

E. agar and M. igon, *Progress in Polymer Science,* 2011, 36, 53-88.

H. Zhang, A. Patel, A. K. Gaharwar, S. M. Mihaila, G. Iviglia, S. Mukundan, H. Bae, H. Yang and A. Khademhosseini, *Biomacromolecules,* 2013, 14, 1299-1310.

W. W. Cleland, *Biochem.,* 1964, 3, 480-482.

H. Nakamoto and J. C. A. Bardwell, *Biochimica et Biophysica Acta (BBA)-Molecular Cell Research,* 2004, 1694, 111-119.

A. Lutzke, A. Pegalajar-Jurado, B. H. Neufeld and M. M. Reynolds, *J. Mater. Chem. B,* 2014, 2, 7449-7458.

D. A. Riccio, P. N. Coneski, S. P. Nichols, A. D. Broadnax and M. H. Schoenfisch, *ACS Appl. Mater. Interfaces,* 2012, 4, 796-804.

D. L. H. Williams, *Acc. Chem. Res.,* 1999, 32, 869-876.

D. L. H. Williams, *Nitrosation reactions and the chemistry of nitric oxide,* Elsevier, 2004.

T. V. O'Halloran and V. C. Culotta, *J. Biol. Chem.,* 2000, 275, 25057-25060.

M. Valko, H. Morris and M. T. D. Cronin, *Curr. Med. Chem.,* 2005, 12, 1161-1208.

B. Roy, A. Du Moulinet d'Hardemare and M. Fontecave, *J. Org. Chem.,* 1994, 59, 7019-7026.

S. M. Shishido and M. G. Oliveira, *Photochem. Photobiol.,* 2000, 71, 273-280.

D. A. Riccio, J. L. Nugent and M. H. Schoenfisch, *Chem. Mater.,* 2011, 23, 1727-1735.

X. Zhai, S. Peleshanko, N. S. Klimenko, K. L. Genson, D. Vaknin, M. Y. Vortman, V. V. Shevchenko and V. V. Tsukruk, *Macromolecules,* 2003, 36, 3101-3110.

X. Zhang, S. Mansouri, D. Mbeh, L. H. Yahia, E. Sacher and T. Veres, *Langmuir,* 2012, 28, 12879-12885.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A degradable polymer having a biodegradable polymer backbone comprising at least one residue having a structure represented by a formula

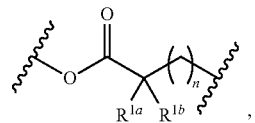

wherein each occurrence of n is independently selected from 0, 1, 2, 3, and 4;

wherein each of $R^{1a}$ and $R^{1b}$ is independently selected from —OH, $C_1$-$C_4$ alkyl, $C_1$-$C_4$ hydroxyalkyl, and —$(CH_2)_nOC(O)L$, provided that at least one of $R^{1a}$ and $R^{1b}$ is —$(CH_2)_nOC(O)L$; and wherein L is a nitric oxide linker moiety pendant from the polymer backbone that has at least one covalently bonded nitric oxide functionality.

2. The polymer of claim 1, wherein the polymer backbone comprises at least one residue having a structure represented by a formula

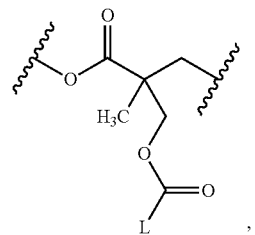

wherein L is the nitric oxide linker moiety.

3. The polymer of claim 1, wherein the nitric oxide linker moiety has a structure represented by a formula

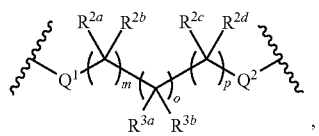

wherein each of m, o, and p is independently selected from 1, 2, 3, and 4;

wherein each of $Q^1$ and $Q^2$ is independently selected from S and $NR^4$;

wherein each occurrence of $R^4$, when present, is independently selected from hydrogen, $C_1$-$C_4$ alkyl, and a protecting group; and wherein each occurrence of $R^{2a}$, $R^{2b}$, $R^{2c}$, and $R^{2d}$ is independently selected from hydrogen and $C_1$-$C_4$ alkyl;

wherein each occurrence of $R^{3a}$ and $R^{3b}$ is independently selected from hydrogen, —$OR^5$, and $C_1$-$C_4$ alkyl; and wherein $R^5$, when present, is selected from hydrogen, $C_1$-$C_4$ alkyl, and an alcohol protecting group.

4. The polymer of claim 3, wherein the nitric oxide linker moiety has a structure selected from

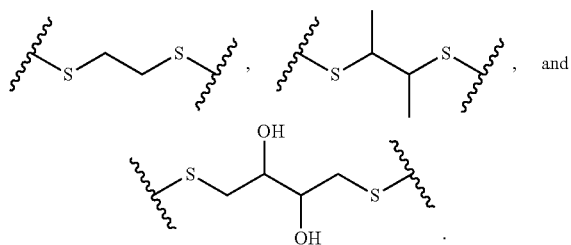

5. The polymer of claim 1, wherein the nitric oxide linker moiety has a structure represented by a formula

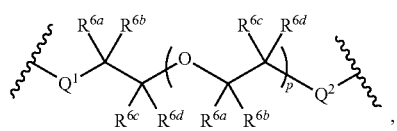

wherein q is selected from 1, 2, 3, and 4;
wherein each of $Q^1$ and $Q^2$ is independently selected from S and $NR^4$;
  wherein each occurrence of $R^4$, when present, is independently selected from hydrogen, $C_1$-$C_4$ alkyl, and a protecting group; and
wherein each occurrence of $R^{6a}$, $R^{6b}$, $R^{6c}$, and $R^{6d}$ is independently selected from hydrogen and $C_1$-$C_4$ alkyl.

6. The polymer of claim 5, wherein the nitric oxide linker moiety has a structure represented by a formula

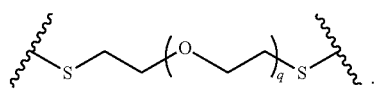

wherein q is selected from 1, 2, 3, and 4.

7. The polymer of claim 1, wherein the nitric oxide linker moiety has a structure represented by a formula

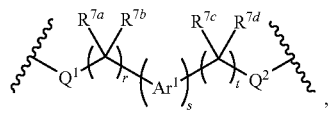

wherein each of r and t is independently selected from 0 and 1;
wherein s is selected from 1, 2, and 3;
wherein each of $Q^1$ and $Q^2$ is independently selected from S and $NR^4$;
  wherein each occurrence of $R^4$, when present, is independently selected from hydrogen, $C_1$-$C_4$ alkyl, and a protecting group;

wherein each occurrence of $R^{7a}$, $R^{7b}$, $R^{7c}$, and $R^{7d}$ is independently selected from hydrogen and $C_1$-$C_4$ alkyl; and
wherein each occurrence of $Ar^1$ is independently selected from aryl, five-membered heteroaryl, and six-membered heteroaryl and is substituted with 0 to 4 non-hydrogen groups independently selected from halogen, —OH, —CN, $C_1$-$C_4$ alkyl, $C_1$-$C_4$ alkoxy, and $C_1$-$C_4$ haloalkyl.

8. The polymer of claim 7, wherein the nitric oxide linker moiety has a structure selected from

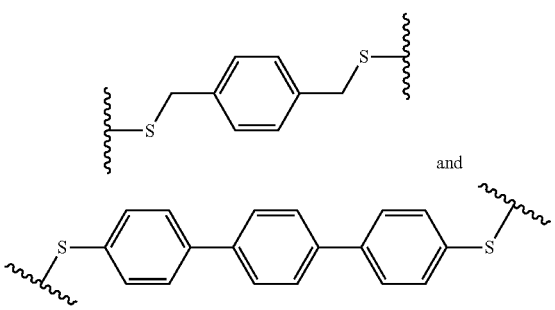

9. The polymer of claim 1, wherein the nitric oxide linker moiety and nitric oxide together comprise a nitrosothiol.

10. A pharmaceutical composition comprising a therapeutically effective amount of at least one degradable polymer of claim 1, or a pharmaceutically acceptable salt thereof, and a pharmaceutically acceptable carrier.

11. The polymer of claim 1, wherein the nitric oxide linker moiety comprises a dithiol.

12. The polymer of claim 1, wherein the nitric oxide linker moiety has a structure selected from

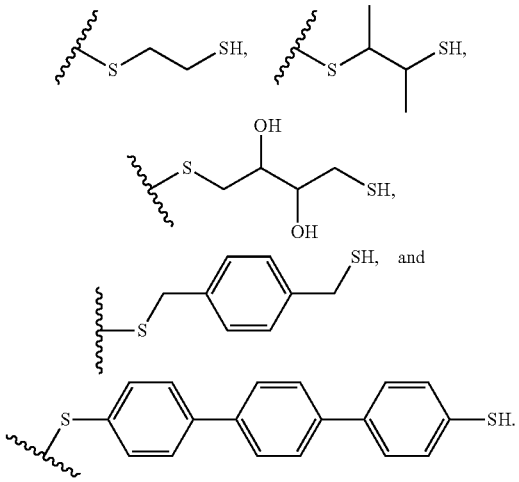

* * * * *

UNITED STATES PATENT AND TRADEMARK OFFICE
CERTIFICATE OF CORRECTION

| | |
|---|---|
| PATENT NO. | : 11,186,681 B2 |
| APPLICATION NO. | : 16/339299 |
| DATED | : November 30, 2021 |
| INVENTOR(S) | : Mark Schoenfisch, Lei Yang and Yuan Lu |

It is certified that error appears in the above-identified patent and that said Letters Patent is hereby corrected as shown below:

In the Specification

Column 1, Lines 14-17, please replace:
"This invention was made with government support under Grant No. DE025207 awarded by the National Institutes of Health (NIH). The government has certain rights in the invention."

With:
-- "This invention was made with government support under Grant Numbers DE025207 and DK108318 awarded by the National Institutes of Health. The government has certain rights in the invention." --

Signed and Sealed this
Twenty-seventh Day of December, 2022

Katherine Kelly Vidal
*Director of the United States Patent and Trademark Office*